United States Patent
Edmunds et al.

(10) Patent No.: US 10,125,139 B2
(45) Date of Patent: Nov. 13, 2018

(54) PESTICIDALLY ACTIVE POLYCYCLIC DERIVATIVES WITH SULFUR SUBSTITUTED FIVE-MEMBERED RING HETEROCYCLES

(71) Applicant: Syngenta Participations AG, Basel (CH)

(72) Inventors: Andrew Edmunds, Stein (CH); Roger Graham Hall, Stein (CH); Michel Muehlebach, Stein (CH); Daniel Emery, Stein (CH); Pierre Joseph Marcel Jung, Stein (CH); Long Lu, Shanghai (CN); Yaming Wu, Shanghai (CN); Ruifang Chen, Shanghai (CN)

(73) Assignees: SYNGENTA CROP PROTECTION AG, Basel (CH); SYNGENTA (CHINA) INVESTMENT CO. LTD., Shanghai (CN)

( * ) Notice: Subject to any disclaimer, the term of this patent is extended or adjusted under 35 U.S.C. 154(b) by 0 days.

(21) Appl. No.: 15/568,817

(22) PCT Filed: Apr. 18, 2016

(86) PCT No.: PCT/EP2016/058534
§ 371 (c)(1),
(2) Date: Oct. 24, 2017

(87) PCT Pub. No.: WO2016/169886
PCT Pub. Date: Oct. 27, 2016

(65) Prior Publication Data
US 2018/0099970 A1    Apr. 12, 2018

(30) Foreign Application Priority Data

Apr. 24, 2015 (WO) ............... PCT/CN2015/007330

(51) Int. Cl.
C07D 487/04 (2006.01)
A01N 43/90 (2006.01)
C07D 471/04 (2006.01)

(52) U.S. Cl.
CPC ........... C07D 487/04 (2013.01); A01N 43/90 (2013.01); C07D 471/04 (2013.01)

(58) Field of Classification Search
CPC ..... C07D 487/04; C07D 471/04; A01N 43/90
See application file for complete search history.

(56) References Cited

U.S. PATENT DOCUMENTS 9,120,792 B2    9/2015 Nokura

FOREIGN PATENT DOCUMENTS

| CN | 104334552 A | 2/2015 | |
|---|---|---|---|
| EP | 2857396 A4 | 10/2015 | |
| WO | 2014/142292 A1 | 9/2014 | |
| WO | 2015/000715 A1 | 1/2015 | |
| WO | WO-2016039444 A1 * | 3/2016 | ............. A01N 43/90 |

OTHER PUBLICATIONS

WO-2016039444-A1, ProQuest English Machine Translation p. 1-77.*
International Search Report and Written Opinion for PCT/CN2015/077330, dated Jan. 27, 2016.
International Search Report and Written Opinion for PCT/EP2016/058534, dated Aug. 19, 2016.

* cited by examiner

*Primary Examiner* — John M Mauro
(74) *Attorney, Agent, or Firm* — Dinsmore & Shohl LLP; Toni-Junell Herbert

(57) ABSTRACT

Polycyclic derivatives of formula (I) wherein the substituents are as defined in claim 1, and the agrochemically acceptable salts, stereoisomers, enantiomers, tautomers and N-oxides of those compounds, can be used as insecticides and can be prepared in a manner known per se.

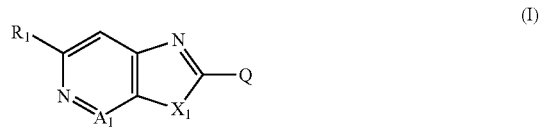

(I)

13 Claims, No Drawings

PESTICIDALLY ACTIVE POLYCYCLIC DERIVATIVES WITH SULFUR SUBSTITUTED FIVE-MEMBERED RING HETEROCYCLES

RELATED APPLICATION INFORMATION

This application is a 371 of International Application No. PCT/EP2016/058534, filed 18 Apr. 2016, which claims priority to PCT/CN2015/077330, filed 24 Apr. 2015, the contents of which are incorporated herein by reference herein.

The present invention relates to pesticidally active, in particular insecticidally active polycyclic derivatives containing sulfur substituents, to compositions comprising those compounds, and to their use for controlling animal pests, including arthropods and in particular insects or representatives of the order Acarina.

Heterocyclic compounds with pesticidal action are known and described, for example, in WO 2012/086848, WO 2013/018928, WO 2013/180193, WO 2014/142292 and WO 2015/000715. There have now been found novel pesticidally active polycyclic ring derivatives with sulfur containing five-membered ring-substituted heterocyles.

The present invention accordingly relates to compounds of formula I,

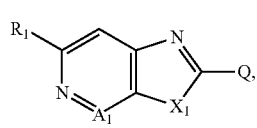

(I)

wherein $A_1$ is methine, nitrogen or the N-oxide;

$R_1$ is hydrogen, halogen, cyano, $C_1$-$C_6$haloalkyl, or $C_1$-$C_6$haloalkyl substituted by one or two substituents selected from the group consisting of hydroxyl, methoxy and cyano; or $R_1$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl; or $R_1$ is $C_3$-$C_6$cycloalkyl which can be mono- or polysubstituted by substituents selected from the group consisting of halogen, cyano and $C_1$-$C_4$alkyl;

$X_1$ is nitrogen substituted with $R_2$, wherein $R_2$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl; or $X_1$ is oxygen or sulfur;

Q is a group Qa or Qb;

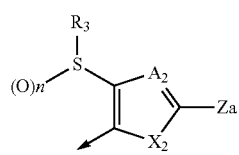

Qa

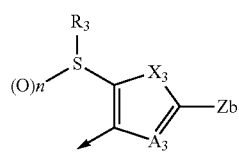

Qb wherein the arrow represents the point of attachment to formula I, and wherein Za and Zb, independently from each other, are phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Za and Zb, independently from each other, are a five- to ten-membered monocyclic or fused bicyclic ring system linked via a carbon atom to the ring which contains the 5-membered heterocycle, said ring system can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Za and Zb are, independently from each other, a five- to six-membered, aromatic, partially saturated or fully saturated ring system linked via a nitrogen atom to the ring which contains the 5-membered heterocycle, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulfur, with the proviso that said ring system cannot contain more than one oxygen atom and more than one sulfur atom; or Za and Zb, independently from each other, are $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl; or Za and Zb, independently from each other, are $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Za and Zb, independently from each other, are $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Za and Zb, independently from each other, are $C_1$-$C_6$alkyl, or $C_1$-$C_6$alkyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl;

$A_2$ is $CR_4$ or nitrogen;
$A_3$ is $CR_5$ or nitrogen;
$R_3$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_3$ is $C_3$-$C_6$cycloalkyl-$C_1$-$C_4$alkyl mono- or polysubstituted by substituents selected from the group consisting of halogen, cyano and $C_1$-$C_4$alkyl; or
$R_3$ is $C_2$-$C_6$alkenyl, $C_2$-$C_6$haloalkenyl or $C_2$-$C_6$alkynyl;
$R_4$ is hydrogen, halogen, or $C_1$-$C_4$alkyl;
$R_5$ is hydrogen, halogen, or $C_1$-$C_4$alkyl;
$X_2$ is oxygen or sulfur;
$X_3$ is oxygen or sulfur;
n is 0, 1 or 2;

and agrochemically acceptable salts, stereoisomers, enantiomers, tautomers of the compounds of formula I.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated. $C_1$-di-alkylamino is dimethylamino.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

Haloalkylsulfanyl is for example trifluoromethylsulfanyl, 2,2,2-trifluoroethylsulfanyl, and pentafluoroethylsulfanyl.

Haloalkylsulfinyl is for example trifluoromethylsulfinyl, 2,2,2-trifluoroethylsulfinyl, or pentafluoroethylsulfinyl.

Haloalkylsulfonyl is for example trifluoromethylsulfonyl, 2,2,2-trifluoroethylsulfonyl, and pentafluoroethylsulfonyl.

Cycloalkyl is, for example, cyclopropyl, cyclobutyl, cyclopentyl and cyclohexyl.

In the context of this invention, examples of a five- to six-membered, aromatic, partially saturated or fully saturated ring system that are linked via a nitrogen atom to the 5-membered heterocyclic ring, are for example, pyrazole, pyrrole, pyrrolidine, pyrrolidine-2-one, piperidine, morpholine, imidazole, triazole and pyridine-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

The compounds of formula I according to the invention also include hydrates which may be formed during the salt formation.

According to the present invention, a five- to ten-membered monocyclic or fused bicyclic hetero-ring system which can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms or a three- to ten-membered, monocyclic or fused bicyclic ring system which may be aromatic, partially saturated or fully saturated is, depending of the number of ring members, preferably selected from the group consisting of the following heterocyclic groups:

pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl, pyranyl; quinazolinyl; isoquinolinyl; indolizinyl; isobenzofuranylnaphthyridinyl; quinoxalinyl; cinnolinyl; phthalazinyl; benzothiazolyl; benzoxazolyl; benzotriazolyl; indazolyl; indolyl; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3-yl)-; (1H-pyrazol-4- yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H-imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-(1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-1hiadiazol-4-yl)-; (1,3,4-thiadiazol-5-yl)-; (1H-tetrazol-1-yl)-; (1H-tetrazol-5-yl)-; (2H-tetrazol-5-yl)-; (2-pyridyl)-; (3-pyridyl)-; (4-pyridyl)-; (2-pyrimidinyl)-; (4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; (1,2,4-triazin-3-yl)-; (furazan-3-yl)-; (2-quinolinyl)-; (3-quinolinyl)-; (4-quinolinyl)-; (5-quinolinyl)-; (6-quinolinyl)-; (3-isoquinolinyl)-; (4-isoquinolnyl)-; (2-quinozolinyl)-; (2-quinoxalinyl)-; (5-quinoxalinyl)-; (pyrido[2,3-b]pyrazin-7-yl)-; (benzoxazol-5-yl)-; (benzothiazol-5-yl)-; (benzo[b]thien-2-yl)- and (benzo[1,2,5]oxadiazol-5-yl)-; indolinyl and tetrahydroquinolynyl.

In preferred compounds of formula I, Za and Zb, independently from each other, are selected from the group consisting of J-0 to J-50:

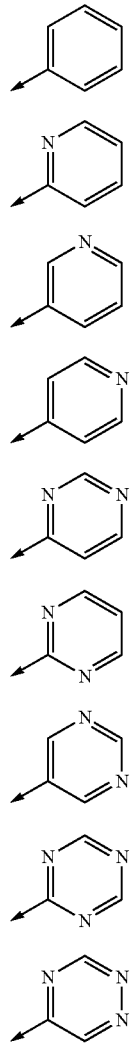

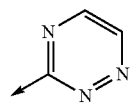

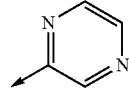

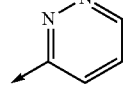

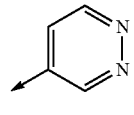

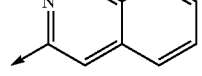

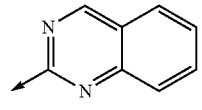

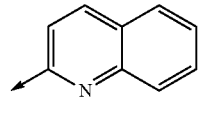

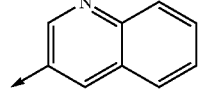

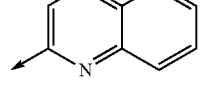

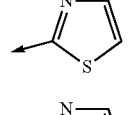

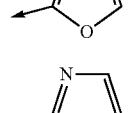

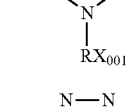

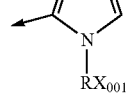

-continued
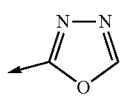 J-11
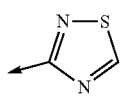 J-12
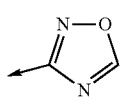 J-13
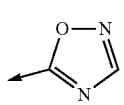 J-14
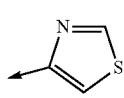 J-15
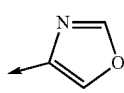 J-16
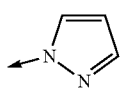 J-17
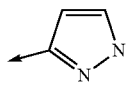 J-18
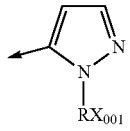 J-19
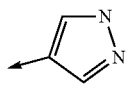 J-20
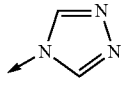 J-21
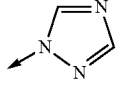 J-22
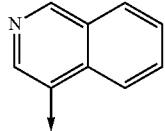 J-23
-continued
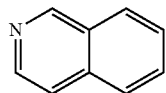 J-24
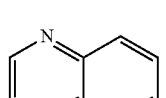 J-25
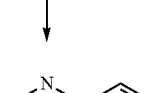 J-26
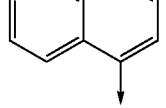 J-27
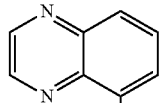 J-28
 J-29
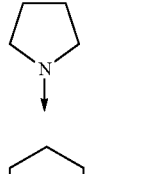 J-30
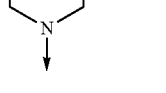 J-31
 J-32
 J-33
 J-34
 J-35
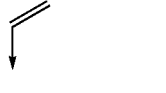 J-36
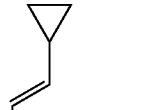 J-37

-continued

J-48

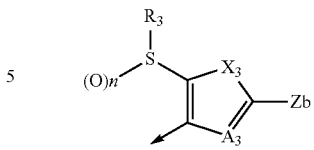

J-49

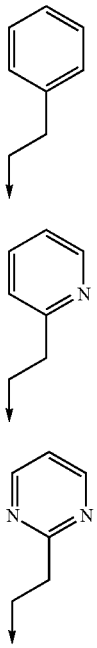

J-50 wherein each group J-0 to J-50 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl. In the substituents J-1 to J-50, $R_{X001}$ is hydrogen or $C_1$-$C_4$alkyl.

Compounds of formula I are preferred,
wherein
$A_1$ is methine, nitrogen or the N-oxide;
$R_1$ is hydrogen, halogen, cyano, $C_1$-$C_6$haloalkyl, or $C_1$-$C_6$haloalkyl substituted by one or two substituents selected from the group consisting of hydroxyl, methoxy and cyano; or
$R_1$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl; or
$R_1$ is $C_3$-$C_6$cycloalkyl which can be mono- or polysubstituted by substituents selected from the group consisting of halogen, cyano and $C_1$-$C_4$alkyl;
$X_1$ is nitrogen substituted with $R_2$, wherein $R_2$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl; or
$X_1$ is oxygen or sulfur;
Q is a group Qa or Qb;

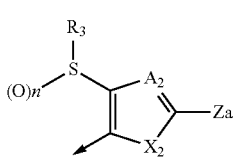

Qa

Qb wherein the arrow represents the point of attachment to formula I, and wherein Za and Zb, independently from each other, are phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O) $C_1$-$C_4$haloalkyl; or Za and Zb, independently from each other, are a five- to ten-membered monocyclic or fused bicyclic ring system linked via a carbon atom to the ring which contains the 5-membered heterocycle, said ring system can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Za and Zb are, independently from each other, a five- to six-membered, aromatic, partially saturated or fully saturated ring system linked via a nitrogen atom to the ring which contains the 5-membered heterocycle, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O) $C_1$-$C_4$haloalkyl; and said ring system contains 1, 2 or 3 heteroatoms selected from the group consisting of nitrogen, oxygen and sulfur, with the proviso that said ring system cannot contain more than one oxygen atom and more than one sulfur atom; or Za and Zb, independently from each other, are $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl; or Za and Zb, independently from each other, are $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Za and Zb, independently from each other, are $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Za and Zb, independently from each other, are $C_1$-$C_6$alkyl, or $C_1$-$C_6$alkyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl;

$A_2$ is $CR_4$ or nitrogen;
$A_3$ is $CR_5$ or nitrogen;
$R_3$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_3$ is $C_3$-$C_6$cycloalkyl-$C_1$-$C_4$alkyl mono- or polysubstituted by substituents selected from the group consisting of halogen, cyano and $C_1$-$C_4$alkyl; or
$R_3$ is $C_2$-$C_6$alkenyl, $C_2$-$C_6$haloalkenyl or $C_2$-$C_6$alkynyl;
$R_4$ is hydrogen, halogen, or $C_1$-$C_4$alkyl;
$R_5$ is hydrogen, halogen, or $C_1$-$C_4$alkyl;
$X_2$ is oxygen or sulfur;
$X_3$ is oxygen or sulfur;
n is 0, 1 or 2;
and agrochemically acceptable salts, stereoisomers, enantiomers, tautomers of the compounds of formula I.

The following embodiments of the invention are preferred:

Embodiment A1

A preferred group of compounds of formula I is represented by the compounds of formula I-1

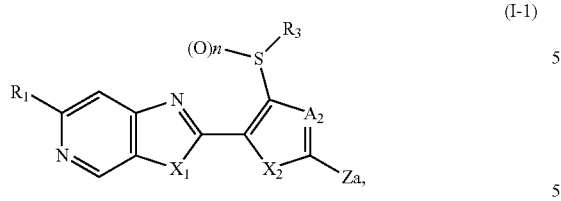

(I-1)

wherein $R_1$, $A_2$, $X_1$, $X_2$, n, and Za are as defined under formula I above; $R_3$ is methyl, ethyl, n-propyl, i-propyl or cyclopropylmethyl; preferably, $X_1$ is N-methyl, oxygen or sulfur.

In said preferred group of compounds of formula I-1, $R_1$ is preferably $C_1$-$C_4$haloalkyl, halogen, $C_1$-$C_4$haloalkylsulfanyl, $C_1$-$C_4$haloalkylsulfinyl, $C_1$-$C_4$haloalkylsulfonyl or $C_1$-$C_4$haloalkoxy; $X_2$ is preferably sulfur; $R_3$ is preferably ethyl; $X_1$ is preferably N-methyl; n is preferably 2, and $A_2$ is nitrogen, methine or C—Cl; In said preferred group of compounds, Za is selected from the group consisting of J-0 to J-50 as mentioned above, where the arrow represents the point of attachment of the heterocycle to the 5-membered heterocycle.

Embodiment A2

Another preferred group of compounds of formula I is represented by the compounds of formula I-1a

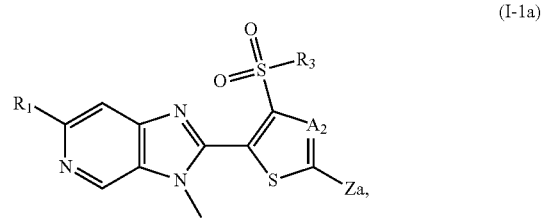

(I-1a)

wherein
$A_2$ is nitrogen, methine, or C—Cl;
$R_3$ is $C_1$-$C_4$alkyl;
$R_1$ is $C_1$-$C_4$haloalkyl, or $C_1$-$C_4$haloalkoxy, $C_1$-$C_4$haloalkylsulfanyl, $C_1$-$C_4$haloalkylsulfinyl or $C_1$-$C_4$haloalkylsulfonyl; Za is selected from the group consisting of

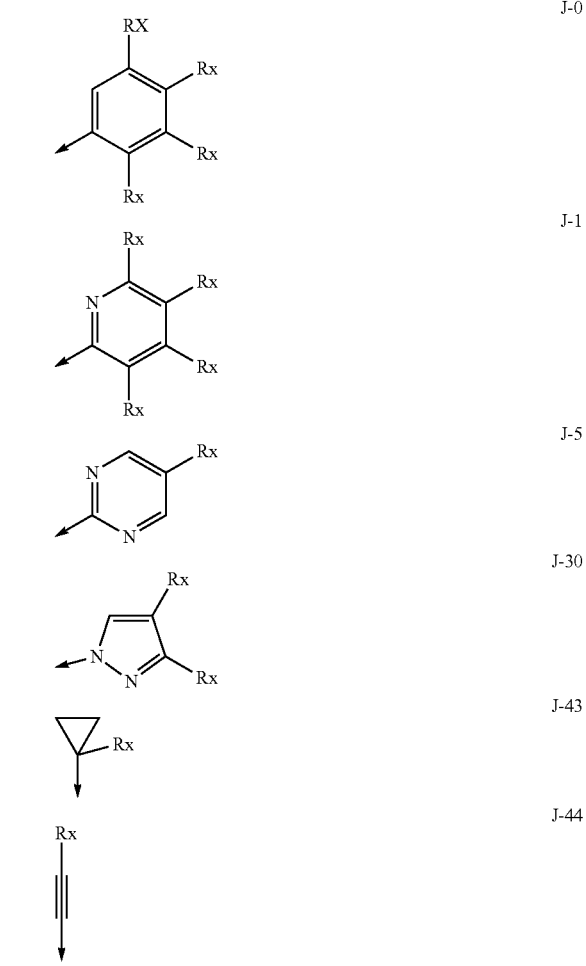

-continued

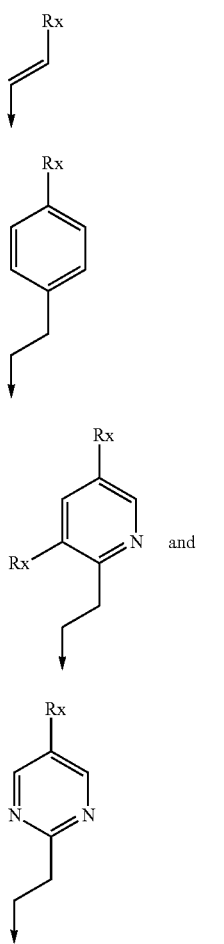

wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; in particular each Rx is, independently from each other, selected from hydrogen, halogen, cyano, $C_1$-$C_4$alkyl and $C_1$-$C_4$haloalkyl.

Embodiment A3

Another preferred group of compounds of formula I is represented by the compounds of formula I-1a2

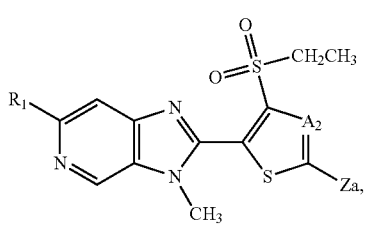

(I-1a2)

wherein
$A_2$ is nitrogen, methine or C—Cl;
$R_1$ is $C_1$-$C_2$haloalkyl, $C_1$-$C_2$haloalkylsulfanyl, $C_1$-$C_2$haloalkylsulfinyl or $C_1$-$C_2$haloalkylsulfonyl, $C_1$-$C_2$haloalkoxy; and Za is selected from the group consisting of

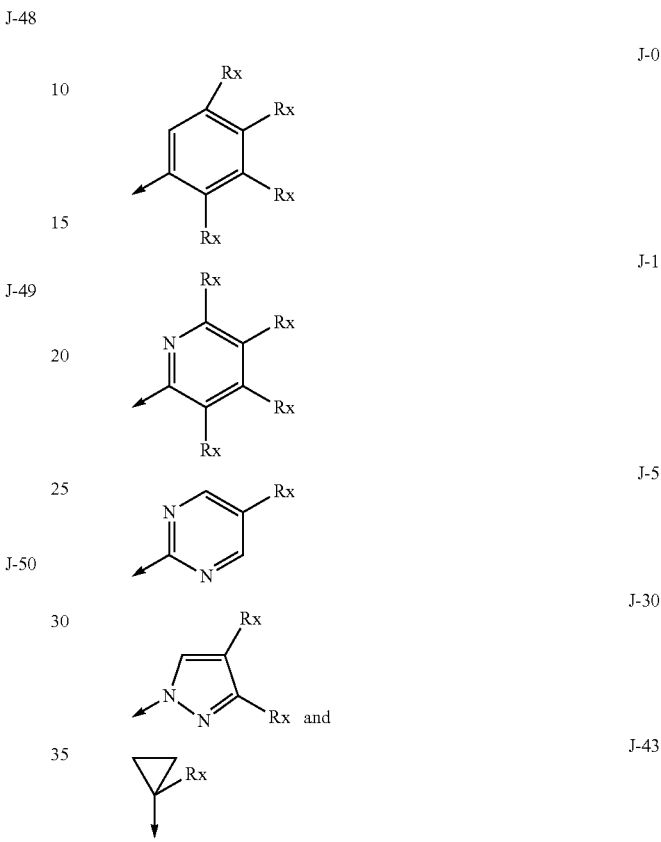

wherein each Rx, independently from each other, is selected from the group consisting of hydrogen, halogen, $C_1$-$C_4$alkyl, cyano and $C_1$-$C_4$haloalkyl.

Embodiment A4

Another preferred compounds of formula I-1a2 are those, in which Za is selected from J-0z1, J-0z2, J0z3, J-1, J-5, J-30 and J-43;

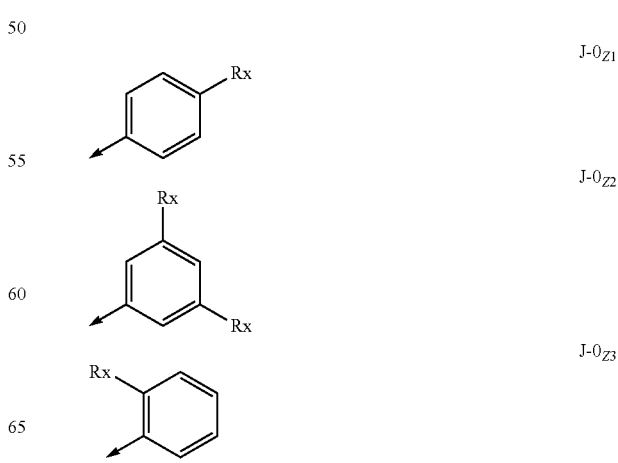

-continued

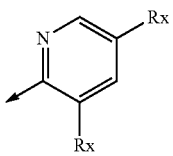
J-1

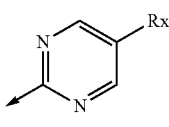
J-5

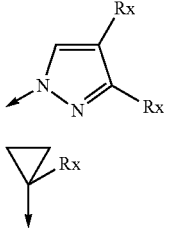
J-30

J-43 wherein each Rx is, independently from each other, is selected from the group consisting of hydrogen, cyano, halogen and $C_1$-$C_4$haloalkyl.

Embodiment A5

Another group of compounds of formula I are represented by the compounds of formula I-1a3;

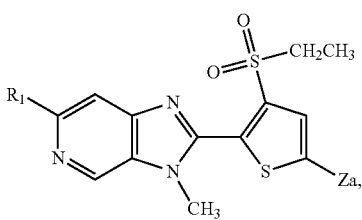
(I-1a3)

wherein Za is as defined under embodiment A4 and $R_1$ is $C_1$-$C_2$haloalkyl, $C_1$-$C_2$haloalkylsulfanyl, $C_1$-$C_2$haloalkylsulfinyl, $C_1$-$C_2$haloalkylsulfonyl or $C_1$-$C_2$haloalkoxy.

Embodiment A6

Another group of compounds of formula I are represented by the compounds of formula I-1a4;

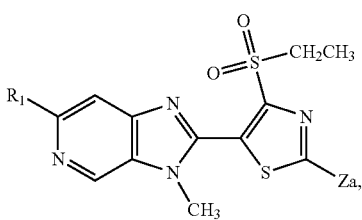
(I-1a4)

wherein Za is as defined under embodiment A4 and $R_1$ is $C_1$-$C_2$haloalkyl, $C_1$-$C_2$haloalkylsulfanyl, $C_1$-$C_2$haloalkylsulfinyl, $C_1$-$C_2$haloalkylsulfonyl or $C_1$-$C_2$haloalkoxy.

Embodiment B1

Another preferred group of compounds of formula I is represented by the compounds of formula I-2

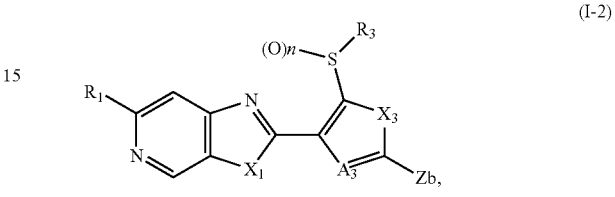
(I-2)

wherein $R_1$, $A_3$, $X_1$, $X_3$, n, and Zb are as defined under formula I above; $R_3$ is methyl, ethyl, n-propyl, i-propyl or cyclopropylmethyl; and $X_1$ is N-methyl, oxygen or sulfur.

Embodiment B2

Another preferred group of compounds of formula I is represented by the compounds of formula I-2a

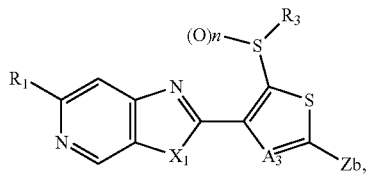
(I-2a)

wherein $A_3$ is nitrogen or methine;

$R_3$ is $C_1$-$C_4$alkyl;

$R_1$ is $C_1$-$C_4$haloalkyl, or $C_1$-$C_4$haloalkoxy, $C_1$-$C_4$haloalkylsulfanyl, $C_1$-$C_4$haloalkylsulfinyl or $C_1$-$C_4$haloalkylsulfonyl; and Zb is selected from the group consisting of

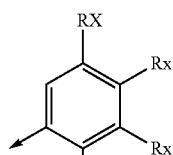
J-0

J-1

-continued

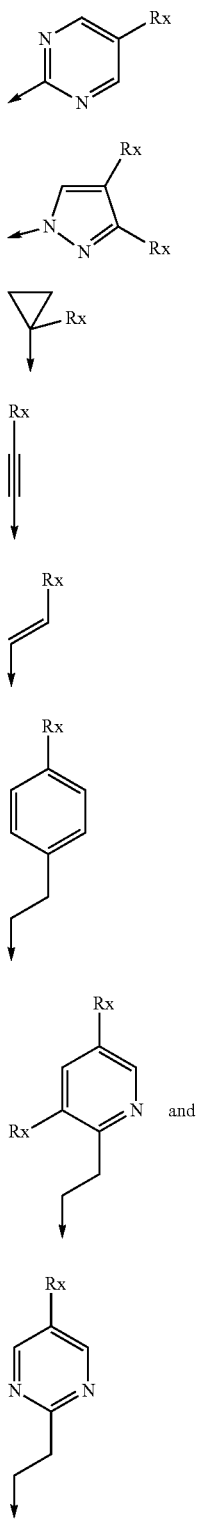

wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; in particular hydrogen, cyano, halogen, $C_1$-$C_4$alkyl, or $C_1$-$C_4$haloalkyl.

Embodiment B3

Another preferred group of compounds of formula I is represented by the compounds of formula I-2a2

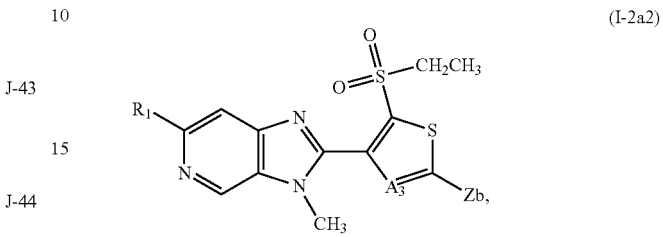

wherein
$A_3$ is nitrogen or methine;
$R_1$ is $C_1$-$C_2$haloalkyl, $C_1$-$C_2$haloalkylsulfanyl, $C_1$-$C_2$haloalkylsulfinyl, $C_1$-$C_2$haloalkylsulfonyl or $C_1$-$C_2$haloalkoxy; and Zb is selected from the group consisting of

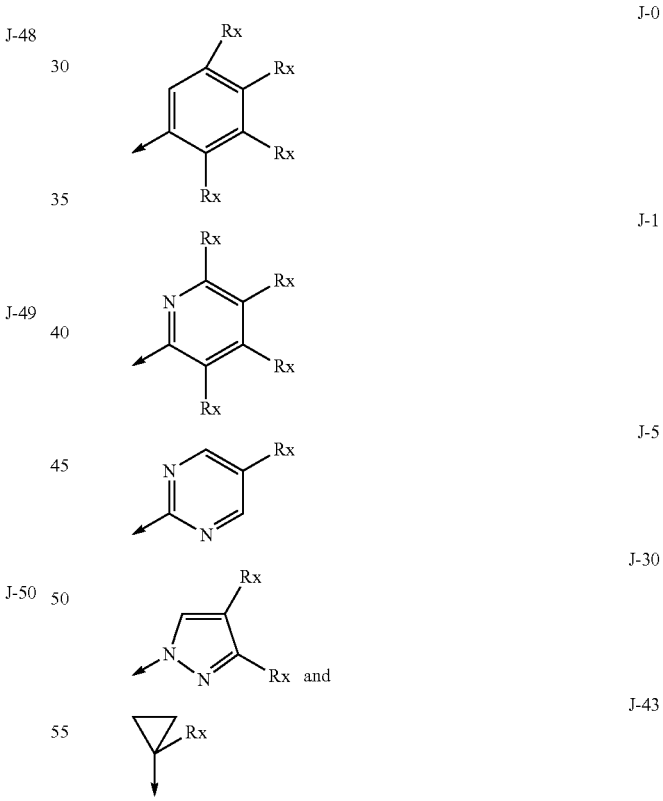

wherein each Rx, independently from each other, is selected from the group consisting of hydrogen, halogen, $C_1$-$C_4$alkyl, cyano and $C_1$-$C_4$haloalkyl.

Embodiment B4

Another preferred compounds of formula I-2a2 are those, in which Zb is selected from J-0z1, J-0z2, J0z3, J-1, J-5, J-30 and J-43;

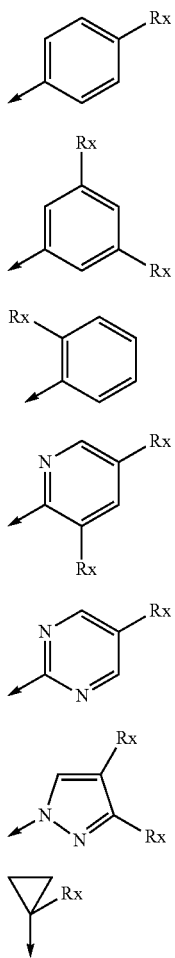

wherein each Rx is, independently from each other, hydrogen, cyano, halogen or $C_1$-$C_4$haloalkyl.

Embodiment B5

Another group of compounds of formula I are represented by the compounds of formula I-2a3;

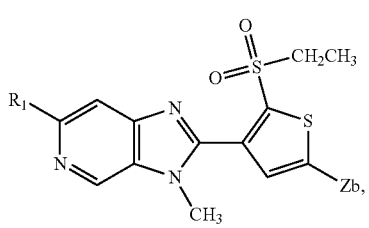

wherein Zb is as defined under embodiment B4 and $R_1$ is $C_1$-$C_2$haloalkyl, $C_1$-$C_2$haloalkylsulfanyl, $C_1$-$C_2$haloalkylsulfinyl, $C_1$-$C_2$haloalkylsulfonyl or $C_1$-$C_2$haloalkoxy.

Embodiment B6

Another group of compounds of formula I are represented by the compounds of formula I-2a4;

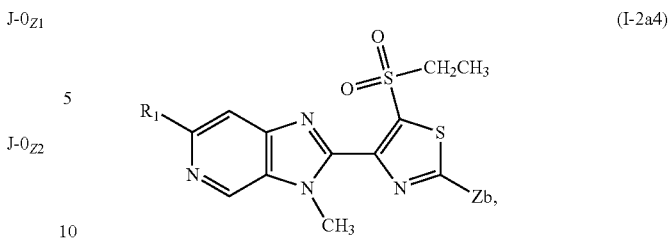

wherein Zb is as defined under embodiment B4 and $R_1$ is $C_1$-$C_2$haloalkyl, $C_1$-$C_2$haloalkylsulfanyl, $C_1$-$C_2$haloalkylsulfinyl, $C_1$-$C_2$haloalkylsulfonyl or $C_1$-$C_2$haloalkoxy.

Embodiment C1

A further preferred group of compounds of formula I is represented by the compounds of formula I-3

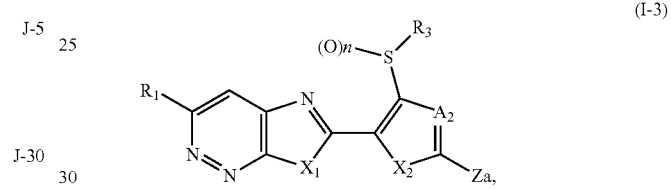

wherein $R_1$, $A_2$, $X_1$, $X_2$, n, and Za are as defined under formula I above; $R_3$ is methyl, ethyl, n-propyl, i-propyl or cyclopropylmethyl; $X_1$ is N-methyl, oxygen or sulfur.

In said preferred group of compounds of formula I-3, $R_1$ is preferably $C_1$-$C_4$haloalkyl, halogen, $C_1$-$C_4$haloalkylsulfanyl, $C_1$-$C_4$haloalkylsulfinyl or $C_1$-$C_4$haloalkylsulfonyl, or $C_1$-$C_4$haloalkoxy; $X_2$ is preferably sulfur; $R_3$ is preferably ethyl; $X_1$ is preferably N-methyl; n is preferably 2, and $A_2$ is nitrogen or methine.

In said preferred group of compounds of formula I-3, Za is preferably selected from the group consisting of J-0 to J-50 as mentioned above (where the arrow represents the point of attachment of the heterocycle to the 5-membered heterocycle).

Embodiment C2

A further preferred group of compounds of formula I is represented by the compounds of formula I-3a

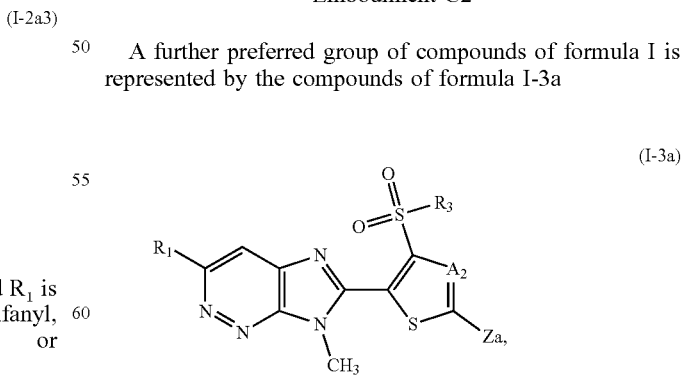

wherein
$A_2$ is nitrogen or methine;
$R_3$ is $C_1$-$C_4$alkyl;

$R_1$ is $C_1$-$C_4$haloalkyl, or $C_1$-$C_4$haloalkoxy, $C_1$-$C_4$haloalkylsulfanyl, $C_1$-$C_4$haloalkylsulfinyl or $C_1$-$C_4$haloalkylsulfonyl; Za is selected from the group consisting of the substituents

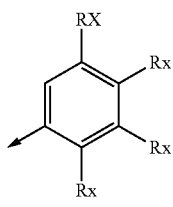

J-0

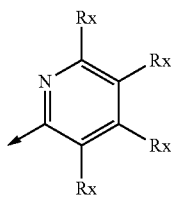

J-1

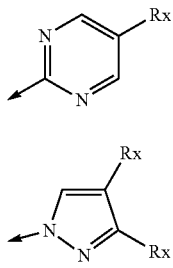

J-5

J-30

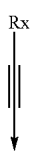

J-43

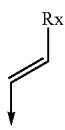

J-44

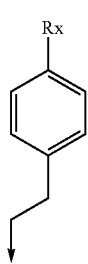

J-46

J-48

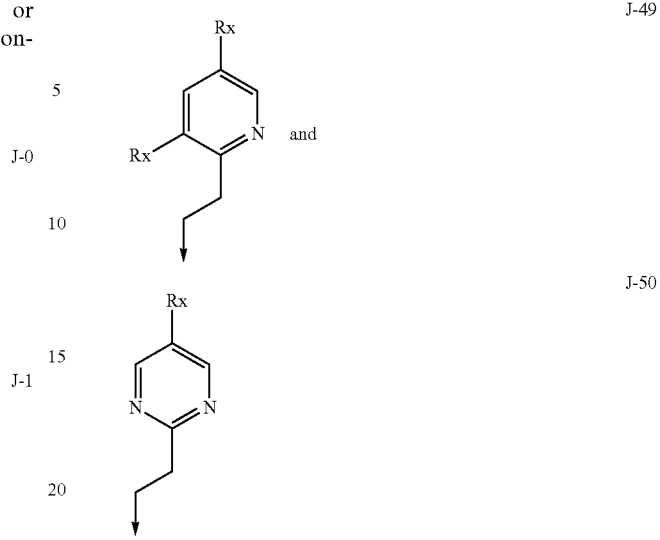

J-49 and

J-50 wherein each Rx is, independently from each other, is selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl, preferably from hydrogen, cyano, halogen, $C_1$-$C_4$alkyl and $C_1$-$C_4$haloalkyl.

Embodiment C3

A further preferred group of compounds of formula I is represented by the compounds of formula I-3a2

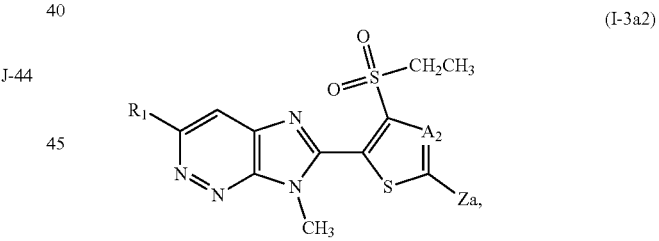
(I-3a2)

wherein
$A_2$ is nitrogen or methine;
$R_1$ is $C_1$-$C_2$haloalkyl, $C_1$-$C_2$haloalkylsulfanyl, $C_1$-$C_2$haloalkylsulfinyl or $C_1$-$C_2$haloalkylsulfonyl, $C_1$-$C_2$haloalkoxy; and Za is selected from the group consisting of

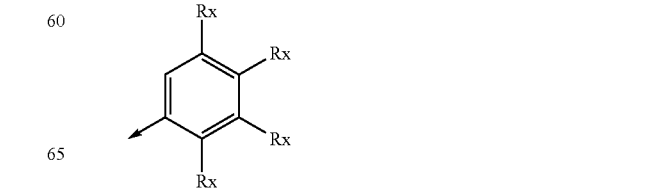

J-0

-continued

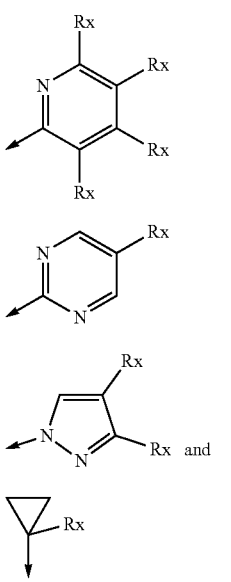

wherein each Rx, independently from each other, is hydrogen, halogen, $C_1$-$C_4$alkyl or $C_1$-$C_4$haloalkyl. In said preferred compounds of formula I-3a2, Rx is, independently from each other, preferably selected from the group consisting of halogen, cyano, hydrogen and $C_1$-$C_4$haloalkyl.

Embodiment C4

Another preferred compounds of formula I-3a2 are those, in which Za is selected from J-0z1, J-0z2, J0z3, J-1, J-5, J-30 and J-43;

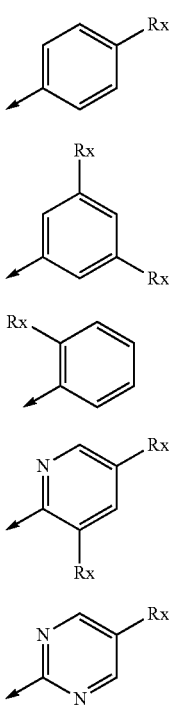

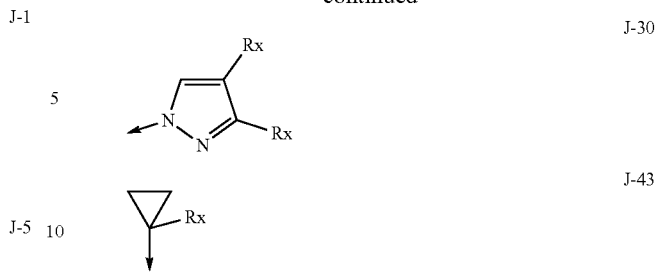

wherein each Rx is, independently from each other, hydrogen, cyano, halogen, or $C_1$-$C_4$haloalkyl.

Embodiment C5

A further preferred group of compounds of formula I is represented by the compounds of formula I-3a3

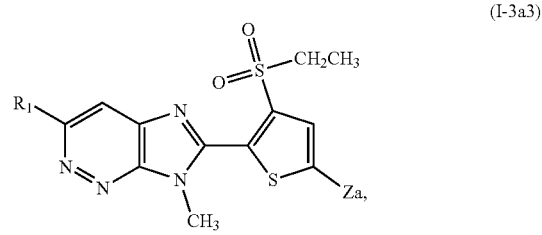

(I-3a3)

wherein Za is as defined under embodiment C4 and $R_1$ is $C_1$-$C_2$haloalkyl, $C_1$-$C_2$haloalkylsulfanyl, $C_1$-$C_2$haloalkylsulfinyl, $C_1$-$C_2$haloalkylsulfonyl or $C_1$-$C_2$haloalkoxy.

Embodiment C6

A further preferred group of compounds of formula I is represented by the compounds of formula I-3a4

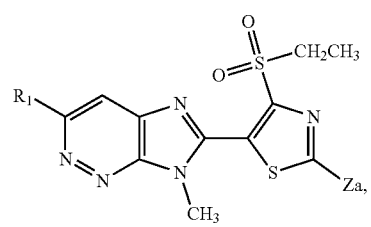

(I-3a4)

wherein Za is as defined under embodiment C4 and $R_1$ is $C_1$-$C_2$haloalkyl, $C_1$-$C_2$haloalkylsulfanyl, $C_1$-$C_2$haloalkylsulfinyl, $C_1$-$C_2$haloalkylsulfonyl or $C_1$-$C_2$haloalkoxy.

Embodiment D1

A preferred group of compounds of formula I is represented by the compounds of formula I-4

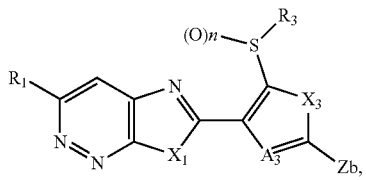

(I-4)

wherein $R_1$, $A_3$, $X_1$, $X_3$, n, and Zb are as defined under formula I above; $R_3$ is methyl, ethyl, n-propyl, i-propyl or cyclopropylmethyl; and $X_1$ is N-methyl, oxygen or sulfur.

Embodiment D2

A further preferred group of compounds of formula I is represented by the compounds of formula I-4a

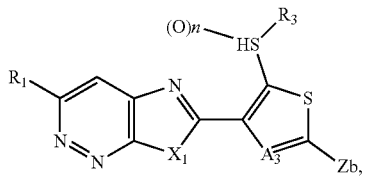

(I-4a)

wherein $A_3$ is nitrogen or methine;

$R_3$ is $C_1$-$C_4$alkyl;

$R_1$ is $C_1$-$C_4$haloalkyl, or $C_1$-$C_4$haloalkoxy, $C_1$-$C_4$haloalkylsulfanyl, $C_1$-$C_4$haloalkylsulfinyl or $C_1$-$C_4$haloalkylsulfonyl; and Zb is selected from the group consisting of

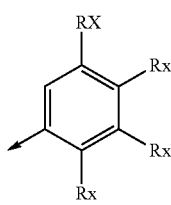

J-0

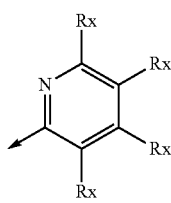

J-1

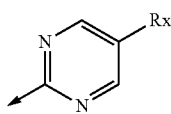

J-5

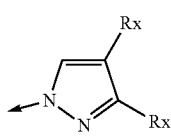

J-30

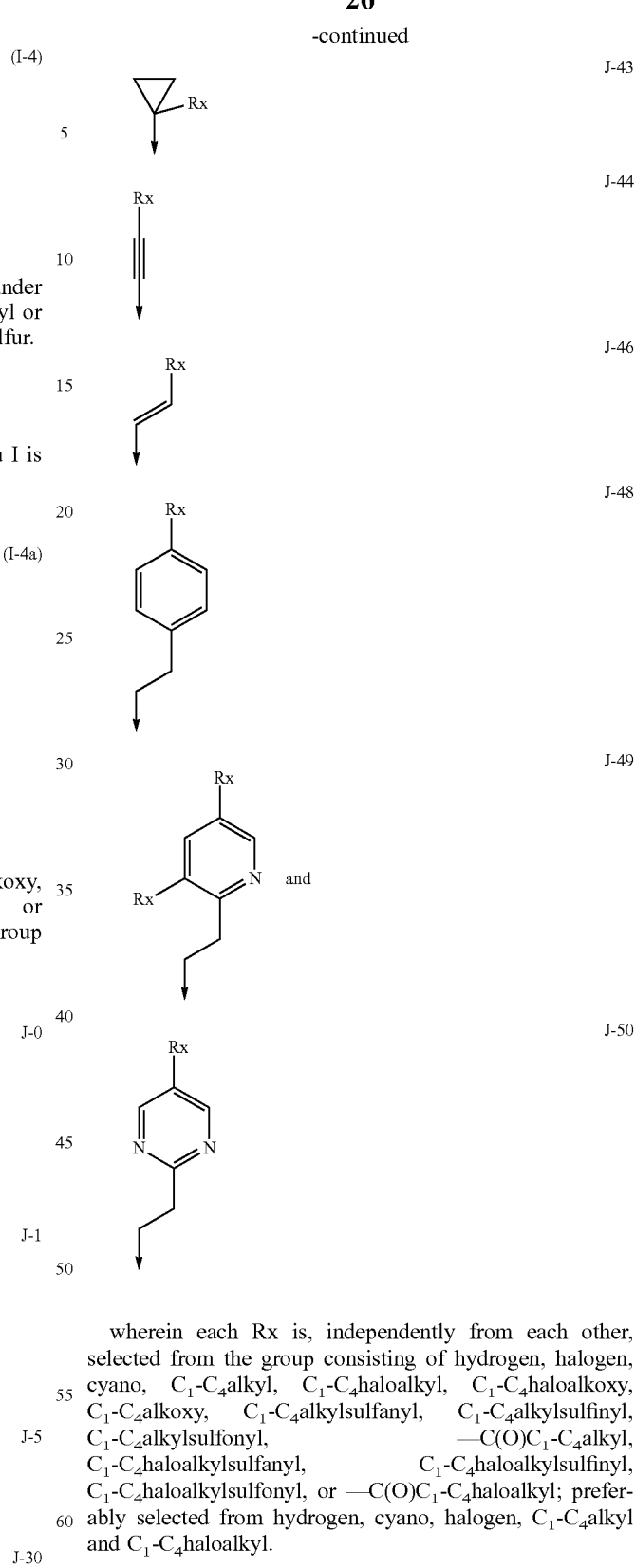

wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl, or —C(O)$C_1$-$C_4$haloalkyl; preferably selected from hydrogen, cyano, halogen, $C_1$-$C_4$alkyl and $C_1$-$C_4$haloalkyl.

Embodiment D3

A further preferred group of compounds of formula I is represented by the compounds of formula I-4a2

(I-4a2)

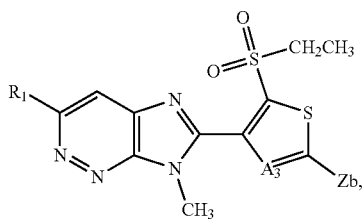

wherein
A₃ is nitrogen or methine;
R₁ is C₁-C₂haloalkyl, C₁-C₂haloalkylsulfanyl, C₁-C₂haloalkylsulfinyl or C₁-C₂haloalkylsulfonyl, C₁-C₂haloalkoxy; and Zb is selected from the group consisting of

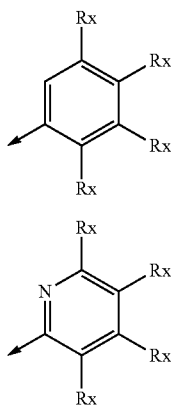 J-0

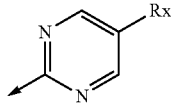 J-1

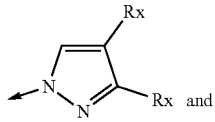 J-5

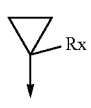 J-30 and

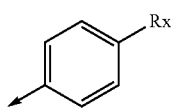 J-43 wherein each Rx, independently from each other, is selected from the group consisting of hydrogen, halogen, C₁-C₄alkyl, cyano and C₁-C₄haloalkyl.

Embodiment D4

Another preferred compounds of formula I-4a2 are those, in which Zb is selected from J-0z1, J-0z2, J0z3, J-1, J-5, J-30 and J-43

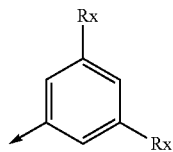 J-0z1

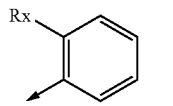 J-0z2

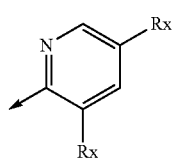 J-0z3

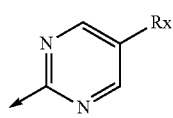 J-1

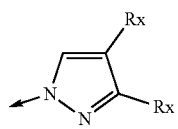 J-5

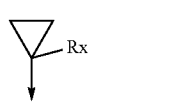 J-30

J-43 wherein each Rx is, independently from each other, is selected from the group consisting of hydrogen, cyano, halogen and C₁-C₄haloalkyl.

Embodiment D5

A further preferred group of compounds of formula I is represented by the compounds of formula I-4a3

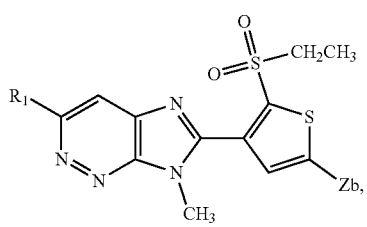 (I-4a3)

wherein Zb is as defined under embodiment D4 and R₁ is C₁-C₂haloalkyl, C₁-C₂haloalkylsulfanyl, C₁-C₂haloalkylsulfinyl, C₁-C₂haloalkylsulfonyl or C₁-C₂haloalkoxy.

Embodiment D6

A further preferred group of compounds of formula I is represented by the compounds of formula I-4a4

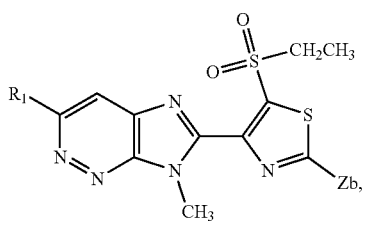

(I-4a4)

wherein Zb is as defined under embodiment D4 and $R_1$ is $C_1$-$C_2$haloalkyl, $C_1$-$C_2$haloalkylsulfanyl, $C_1$-$C_2$haloalkylsulfinyl, $C_1$-$C_2$haloalkylsulfonyl or $C_1$-$C_2$haloalkoxy.

Embodiment E1

In all of the embodiments A1 to A6, B1 to B6, C1 to C6 and D1 to D6, $R_1$ is preferably $C_1$-$C_2$haloalkyl.

Embodiment E2

Especially preferred are compounds of formula I, wherein
$R_1$ is $C_1$-$C_2$haloalkyl;
$A_1$ is methine;
$X_1$ is nitrogen substituted with methyl;
Q is Qa,

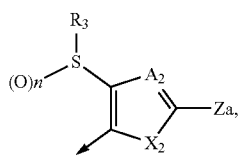

(Qa)

wherein
n is 2;
$R_3$ is ethyl;
$X_2$ is sulfur;
$A_2$ is $CR_4$ or nitrogen; wherein
$R_4$ is hydrogen or halogen; and
Za is halogen, phenyl which can be substituted by $C_1$-$C_4$haloalkyl, or Za is pyrimidine or pyrazolyl which can be substituted by $C_1$-$C_4$haloalkyl.

The process according to the invention for preparing compounds of formula I is carried out by methods known to those skilled in the art, and as described below:

Compounds of formula I, respectively Ia, wherein $A_1$, $R_1$, $X_1$ are as defined in formula I, and Q is a group Qa, can prepared (as shown in scheme 1) by a Suzuki reaction, which involves for example, reacting compounds of formula IIa, wherein $Xb_1$ is a leaving group, for example, chlorine, bromine or iodine, or an aryl- or alkylsulfonate such as trifluoromethanesulfonate with compounds of formula IIIa1, wherein $Y_{b1}$ can be a boron-derived functional group, as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction can be catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water, or of dioxane and water, preferably under an inert atmosphere. The reaction temperature can preferentially range from ambient temperature to the boiling point of the reaction mixture. Such Suzuki reactions are well known to those skilled in the art and have been reviewed, for example J. Orgmet. Chem. 576, 1999, 147-168.

Scheme 1:

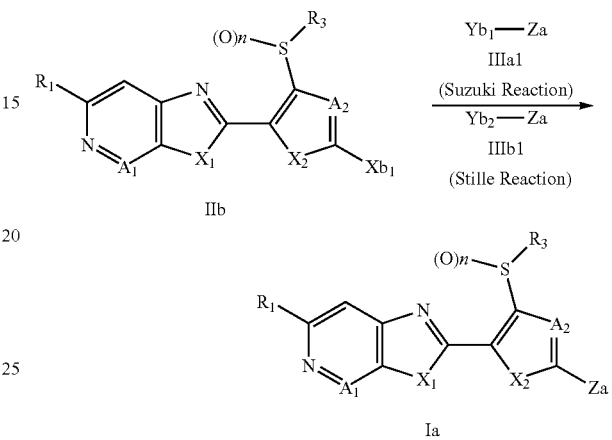

Alternatively compounds of formula Ia can be prepared by a Stille reaction of compounds of formula IIIb1 wherein $Y_{b2}$ is a trialkyl tin derivative, preferably tri-n-butyl tin, with compounds of formula IIa (Scheme 1

Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example J. Org. Chem., 2005, 70, 8601-8604, J. Org. Chem., 2009, 74, 5599-5602, and Angew. Chem. Int. Ed., 2004, 43, 1132-1136. Compounds of formula I, respectively Ib, wherein $A_1$, $R_1$ $X_1$ are as defined in formula I, and Q is a group Qb, can prepared in the same manner (scheme 2) by Suzuki or Stille reactions of compounds of formula IIb, wherein $A_1$, $A_3$, $R_1$, $R_3$, n, $X_1$, and $X_3$ are as defined in formula I, and $Xb_1$ is a leaving group, for example, chlorine, bromine or iodine, or an aryl- or alkylsulfonate such as trifluoromethanesulfonate, with compounds of formula IIIa2 or IIIb2.

Scheme 2:

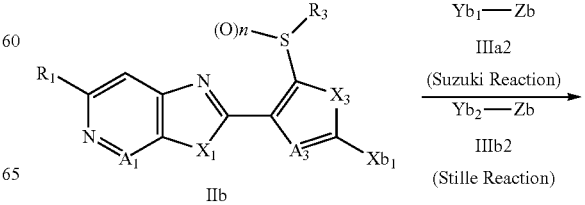

-continued

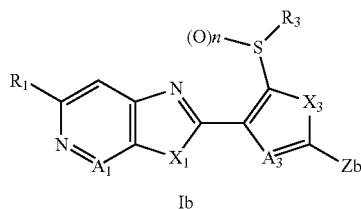

Ib

Compounds of formula I, respectively Iaa, wherein $A_1$, $R_1$, and $X_1$ defined in formula I, and Q is a group Qa and wherein the group Za in Qa is a nitrogen bearing heterocyclic system, can be prepared from compounds of formula IIa, wherein $A_1$, $A_2$, $R_1$, $R_3$, $X_1$, $X_2$ and n are as defined in formula I, and $Xb_1$ is a leaving group such as chlorine, bromine or iodine, or an aryl- or alkylsulfonate such as trifluoromethanesulfonate by reacting the heterocycle Za (which contains an appropriate NH functionality), in the presence of a base, for example an alkaline metal hydride such as sodium hydride, or an alkali metal carbonate, for example cesium or potassium carbonate, optionally in the presence of a copper catalyst, for example copper (I) iodide in an inert solvent such as N-methyl pyrollidione or DMF at temperatures between 30-150° C., optionally in the presence of a diamine ligand, such as N,N'-dimethylethane-1,2-diamine methane. Alternatively compounds of formula Iaa can be prepared from compounds of formula IIa, wherein $A_1$, $A_2$, $R_1$, $R_3$, $X_1$, $X_2$, $Xb_1$ and n are as previously defined, by reaction of the heterocycle Za (which contains a an appropriate NH functionality), in the presence of a base, for example an alkaline metal hydride such as sodium hydride, or an alkali metal carbonate, for example cesium or potassium carbonate, in an appropriate solvent such as N-methyl pyrollidione or DMF at temperatures between 30-150° C. The reaction is illustrated for the heterocycle J-30 in scheme 3, which gives compounds of formula Iaa, wherein $A_1$, $A_2$, $R_1$, $R_3$, $X_1$, $X_2$, n and $R_x$ are as previously defined.

Scheme 3

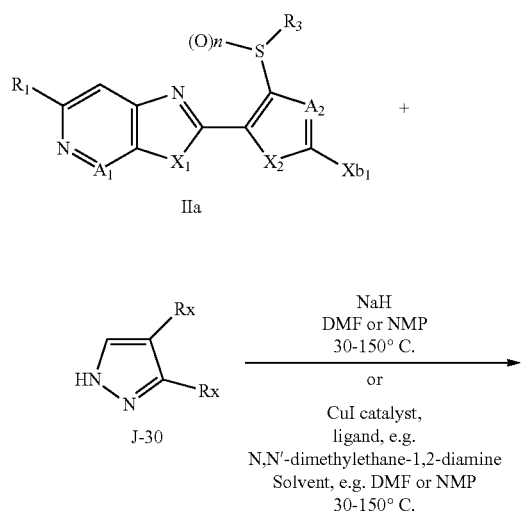

-continued

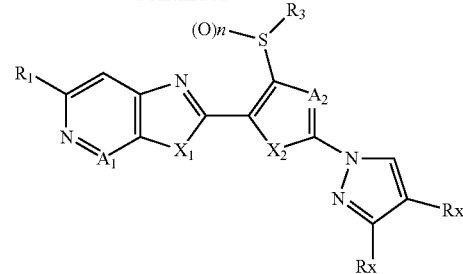

Iaa

In a similar manner, compounds of formula Iab wherein $A_1$, $R_1$, and $X_1$ defined in formula I, and Q is a group Qb and wherein the group Zb in Qb is a nitrogen bearing heterocyclic system, can be prepared from compounds of formula IIb, wherein $A_1$, $A_3$, $R_1$, $R_3$, $X_1$, $X_3$ and n are as defined in formula I, and $Xb_1$ is a leaving group such as chlorine, bromine or iodine, or an aryl- or alkylsulfonate such as trifluoromethanesulfonate by reacting the heterocycle Zb (which contains a an appropriate NH functionality), under the conditions described in scheme 3, and illustrated in scheme 4 for the heterocycle J-30, which gives compounds of formula Iab wherein the substituents $A_1$, $A_3$, $R_1$, $R_3$, $X_1$, $X_3$, Rx, and n are as previously described.

Scheme 4:

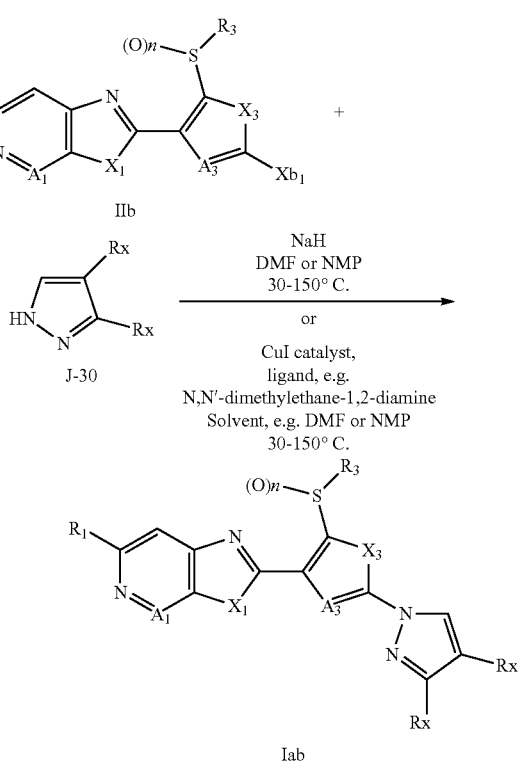

Iab

Compounds of formula I, respectively Ia, can also be prepared (as depicted in scheme 5) by a Suzuki reaction as described above, which involves reacting compounds of formula IVa with compounds of formula Va, wherein $X_{b2}$ can be a halogen, preferentially chlorine, bromine or iodine, or a sulfonate, like for example a trifluoromethanesulfonate and $Y_{b3}$ can be a boron-derived functional group, as for example $B(OH)_2$ or $B(OR_{b2})_2$ wherein $R_{b2}$ can be a $C_1$-$C_4$alkyl group or the two groups $OR_{b2}$ can form together with the boron atom a five membered ring, as for example a pinacol boronic ester. In formula IVa, $A_1$, $A_2$, $X_1$, $X_2$, $R_1$, $R_3$, and n, are as described in formula I.

The reaction can be catalyzed by a palladium based catalyst, for example tetrakis(triphenylphosphine)-palladium, in presence of a base, like sodium carbonate, in a solvent or a solvent mixture, like, for example a mixture of 1,2-dimethoxyethane and water, preferably under inert atmosphere. The reaction temperature can preferentially range ambient temperature to the boiling point of the reaction mixture.

Scheme 6

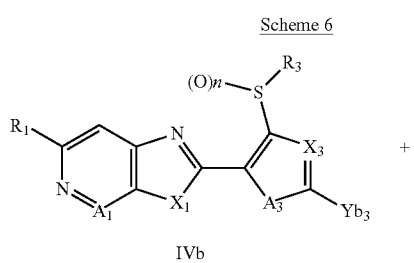

IVb

Scheme 5

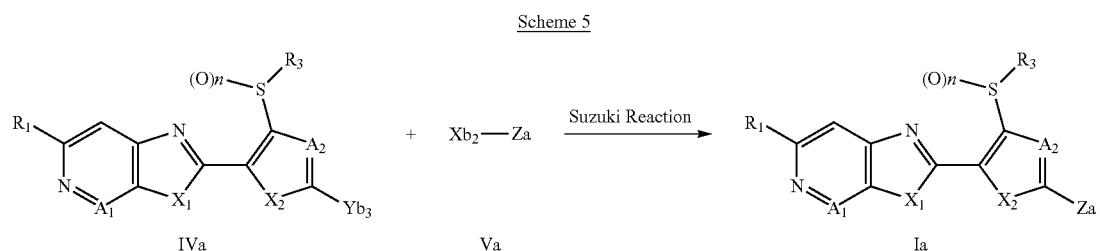

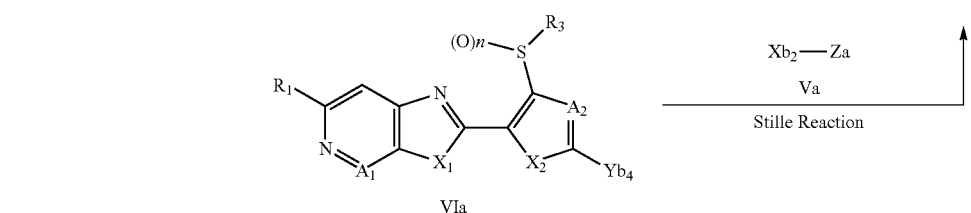

In a similar manner, compounds of formula Ia can be prepared by a Stille coupling (scheme 5) of compounds of formula Va with compounds of formula VIa, wherein $A_1$, $A_2$, $X_1$, $X_2$, $R_1$, $R_3$, and n are as described above, and $Y_{b4}$ is a trialkyl tin derivative, preferably tri-n-butyl tin, under conditions described as in scheme 1.

In a similar fashion (scheme 6), compounds of formula I, respectively Ib, where Q is a group Qb, and Zb, $X_1$, $X_3$, $A_1$, $A_3$, $R_1$, $R_3$ and n are as described in formula I, can be prepared by a Suzuki reaction between a compound of formula IVb, wherein $X_1$, $X_3$, $A_1$, $A_3$, $R_1$, $R_3$ and n are as described in formula I, with compounds of formula Vb, wherein $X_{b2}$ can be a halogen, preferentially chlorine, bromine or iodine, or a sulfonate, like for example a trifluoromethanesulfonate and $Y_{b3}$ can be a boron-derived functional group, as for example $B(OH)_2$ or $B(OR_{b2})_2$ wherein $R_{b2}$ can be a $C_1$-$C_4$alkyl group or the two groups $OR_{b2}$ can form together with the boron atom a five membered ring, as for example a pinacol boronic ester, under conditions described previously. Similarly, compounds of formula I can be prepared by a Stille coupling (Scheme 6) of compounds of formula Vb with compounds of formula VIb, wherein $A_1$, $A_3$, $X_1$, $X_3$, $R_1$, $R_3$, and n are as described above, and $Y_{b4}$ is a trialkyl tin derivative, preferably tri-n-butyl tin, under conditions described as in scheme 1. The reactions are summarized in scheme 6.

-continued

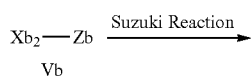

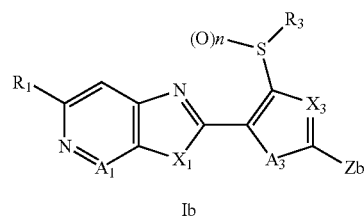

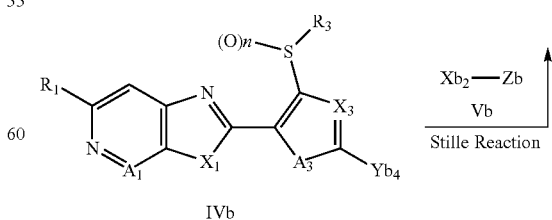

Compounds of formula I can be prepared by reaction of a compound of formula VIIa or VIIb

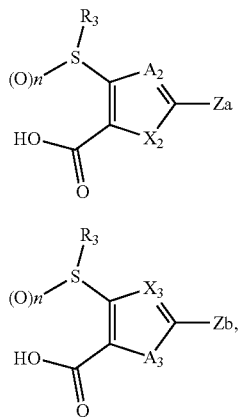

wherein $X_2$, $X_3$, $A_2$, $A_3$, $R_3$, Za, Zb and n are as described under formula I above, with a compound of formula VIII,

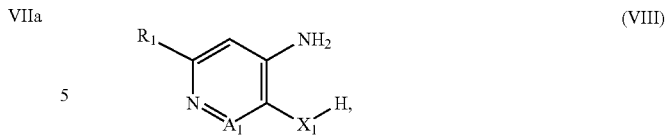

wherein $A_1$ and $R_1$ are as described under formula I above, and $X_1$ is $NR_2$, wherein $R_2$ is hydrogen is as described under formula I above, in the presence of a de-hydrating agent, such as for example polyphosphoric acid at temperature between 150° C. to 250° C., to yield compounds of formula I, wherein the substituents are as described above and under formula I. Such processes are well known and have been described for example in WO 2008/128968, WO 2012/086848, WO 2013/018928, WO 2014/142292 and WO 2006/003440. The process is summarized in scheme 7 for compounds of formula Ia:

Scheme 7

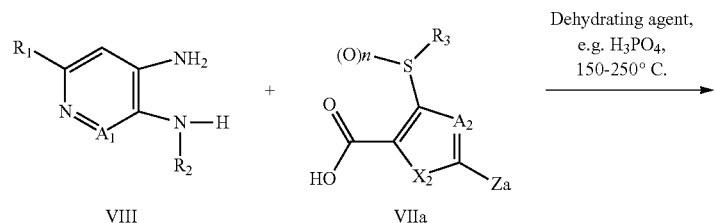

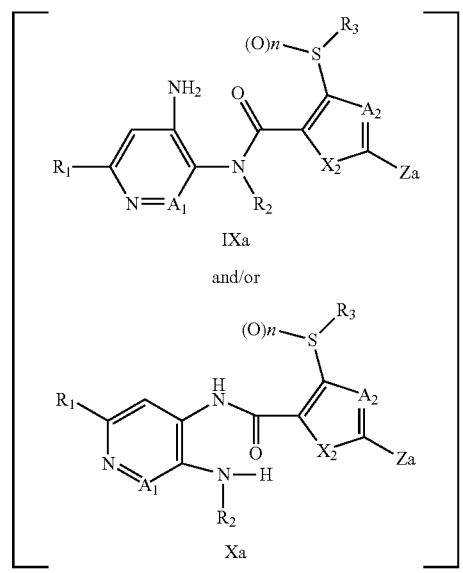

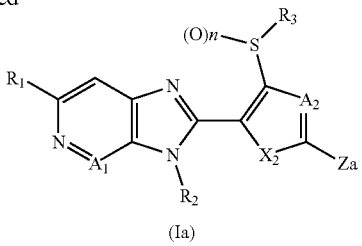

(Ia)

As can be seen in scheme 7, the formation of compounds of formula Ia occurs through the intermediacy of a compound of formula IXa (and/or its position isomer Xa). Intermediates IXa or intermediate Xa may form as a pure entity, or intermediates IXa and Xa may arise as a mixture of regioisomeric acylation products. It is in many cases advantageous to thus prepare compounds of formula (Ia) through such intermediates IXa/Xa, which may be isolated and optionally purified. This is illustrated in a different synthesis for compounds of formula I, respectively Ib, in scheme 8, which in this case involves the intermediates IXb and Xb, and in scheme 9 for compounds of formula Ia via intermediates IXa and Xa.

Scheme 8.

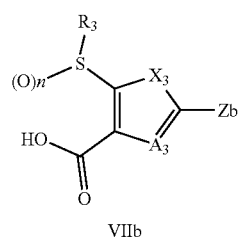

VIIb (COCl)$_2$, inert solvent, e.g. CH$_2$Cl$_2$ room temp, or SOCl$_2$, CH$_2$Cl$_2$ room temp. or DCC, EDC, THF or pyridine, rt-120 deg.

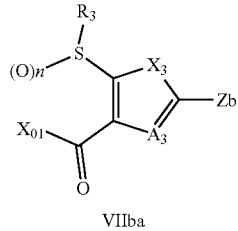

VIIba

VIII optionally in the presence of an additional base, such as triethylamine or pyridine

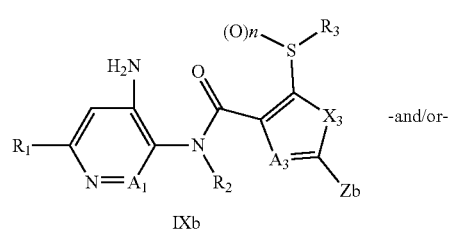

IXb

-and/or-

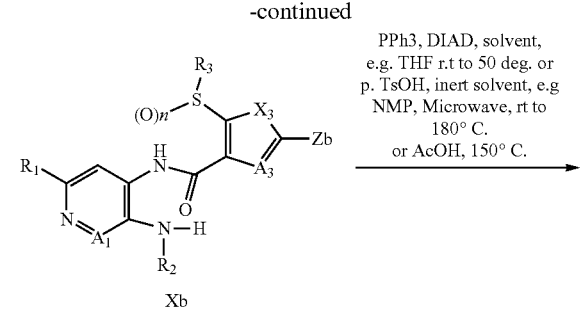

Xb

PPh3, DIAD, solvent, e.g. THF r.t to 50 deg. or p. TsOH, inert solvent, e.g NMP, Microwave, rt to 180° C. or AcOH, 150° C.

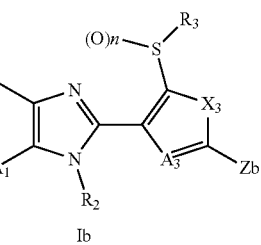

Ib wherein:

X$_{01}$ = Halogen,

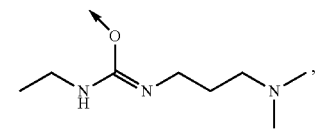

Scheme 9:

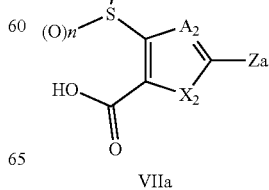

VIIa (COCl)$_2$, inert solvent, e.g. CH$_2$Cl$_2$ room temp, or SOCl$_2$, CH$_2$Cl$_2$ room temp. or DCC, EDC, THF or pyridine, rt-120 deg.

-continued

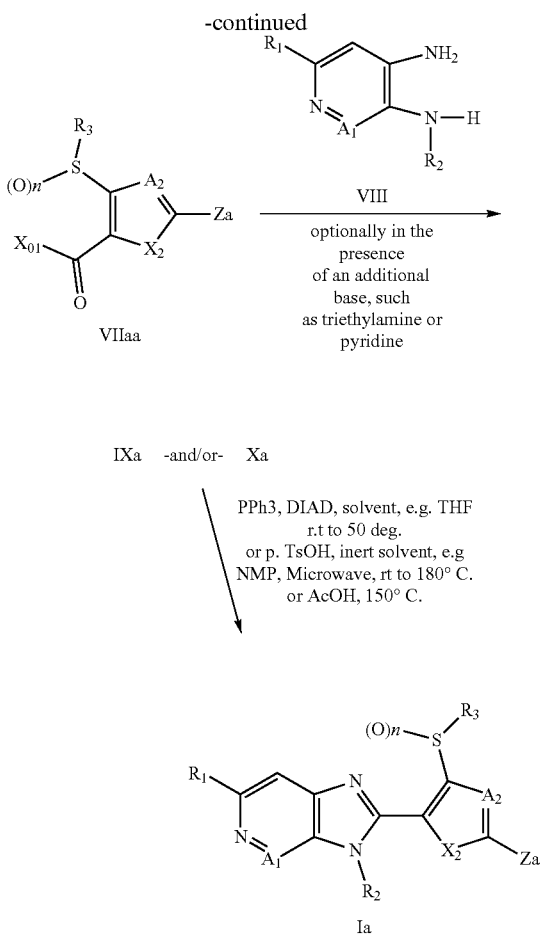

Compounds of the formula IXa and/or Xa and IXb and/or Xb, or a salt thereof, may be prepared (scheme 8 and scheme 9) by;

i) activation of compound of formula VIIa or VIIb, by methods known to those skilled in the art and described in, for example, *Tetrahedron*, 2005, 61 (46), 10827-10852, to form an activated species VIIba or VIIaa, wherein $X_{01}$ is halogen, preferably chlorine. For example, compounds VIIaa or VIIba where $X_{01}$ is halogen, preferably chlorine, are formed by treatment of VIIa or VIIb with, for example, oxalyl chloride $(COCl)_2$ or thionyl chloride $SOCl_2$ in the presence of catalytic quantities of N,N-dimethylformamide (DMF) in inert solvents such as methylene chloride or tetrahydrofurane at temperatures between 20 to 100° C., preferably 25° C. Alternatively, treatment of compounds of formula VIIa or VIIb with, for example, 1-ethyl-3-(3-dimethylaminopropyl)carbodiimide (EDC) or dicyclohexyl carbodiimide (DCC) will generate an activated species VIIaa or VIIba, wherein $X_{01}$ is respectively, in an inert solvent, such as pyridine or tetrahydrofurane, optionally in the presence of a base, such as triethylamine, at temperatures between 25-180° C.; followed by;

ii) treatment of the activated species VIIba or VIIaa with a compound of formula VIII (or a salt thereof), wherein $A_1$ and $R_1$ are as described under formula I above, $X_1$ is $NR_2$, and $R_2$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl, optionally in the presence of a base, such as triethylamine or pyridine, in an inert solvents such as dichloromethane, tetrahydrofurane, dioxane or toluene, at temperatures between 0 and 80° C., to form the compounds of formula IXa and/or Xa and IXb and/or Xb.

Compounds of formula Xa and/or IXa and Xb and/or IXb may further be converted into compounds of formula Ia and Ib (schemes 8 and 9), by dehydration, e.g. by heating the compounds IXa and/or Xa and IXb and/or Xb in the presence of an acid catalyst, such as for example methane sulfonic acid, or para-toluene sulfonic acid (TsOH), in an inert solvent such as N-methyl pyrrolidine at temperatures between 25-180° C., preferably 100-170° C., optionally under microwave conditions, or by heating in acetic acid at temperatures between 100-180° C. Such processes have been described previously, for example, in WO 2010/125985 and WO2015/000715. Compounds of formula VIIa and VIIb are obtained by hydrolysis of the corresponding esters, for example compound VIIab, Xia or XIb (see below), using conditions known to those skilled in the art. An alternative synthesis of compounds of formula I is illustrated in scheme 10.

Scheme 10:

VIIa, Q is Qa
VIIb, Q is Qb

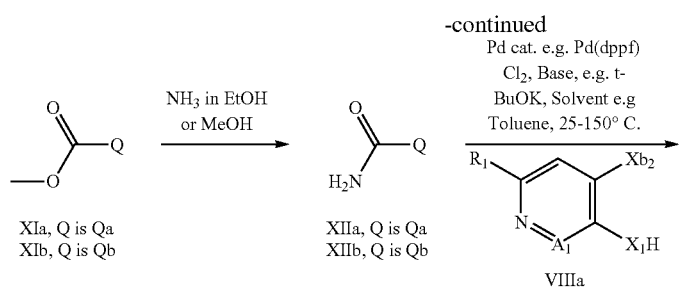

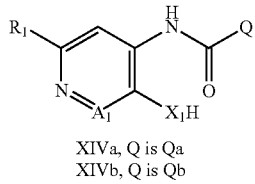

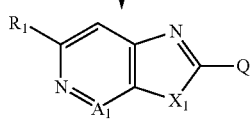

Ia, Q is Qa
Ib, Q is Qb

As shown in scheme 10, compounds of formula VIIa and VIIb can be converted to XIa and XIb, by methods known to those skilled in the art. Compounds of formula XIa or XIb are then treated with ammonia in a suitable solvent, for example methanol or ethanol, to give the amides of formula XIIa or XIIb. Reaction of the amides of formula XIIa or XIIb with compounds of formula VIIIa, wherein $A_1$, $R_1$ and $X_1$ are as described in formula I, and $Xb_2$ is halogen, leads to compounds of formula XIVa or XIVb. Such an amide nitrogen heteroarylation reaction, typically runs under transition metal-catalysed C—N bond formation conditions involving a catalytic system (such as for example [1,1'-bis (diphenylphosphino) ferrocene] dichloropalladium(II)), usually composed of a metal, such as a palladium source (for example palladium(0) precursors like $Pd_2$ (dibenzylideneacetone)$_3$, or palladium(II) precursors like $Pd(OAc)_2$) and a ligand (for example phosphine-based or N-heterocyclic carbene-based), a base, such as alkoxides (for example sodium or potassium tert-butoxide), carbonates, phosphates or silyl amides (for example potassium or cesium carbonate, potassium phosphate, or lithium hexamethyl disilazane) or hydroxides (for example sodium or potassium hydroxide), and solvents such as toluene, tetrahydrofurane, dioxane, dimethoxyethane, N,N-dimethyl formamide, N-methyl pyrrolidone and dimethylsulfoxide, as well as their aqueous solutions. These methods are known to those skilled in the art and described, for example, in WO 2014/142292. Under those above described amide cross-coupling reaction conditions, the compounds of formula XIVa or XIVb can be isolated, and converted to compounds of formula I as described in schemes 8 and 9) but may also spontaneously ring-close into the compounds of formula I, especially in cases where $X_1$ is $NR_2$.

A further syntheses of compounds of formula I are shown in Schemes 11 and 12:

Scheme 11:

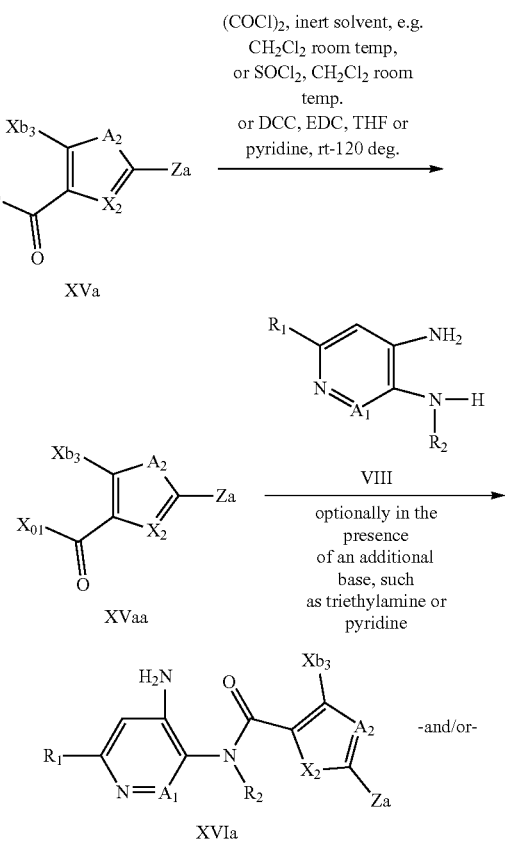

-continued

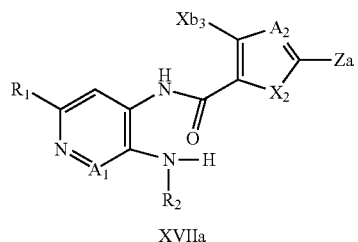

XVIIa

PPh3, DIAD, solvent, e.g. THF r.t to 50 deg. or p. TsOH, inert solvent, e.g NMP, Microwave, rt to 180° C. or AcOH, 150° C.

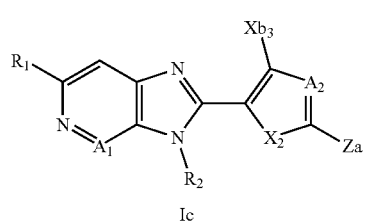

Ic $M_0SR_3$
Solvent e.g.
NMP, DMF, THF
Rt to 100° C.

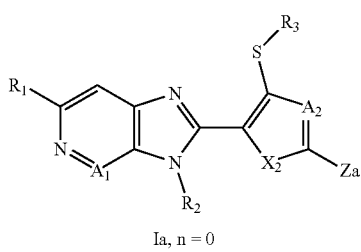

Ia, n = 0

Oxidation

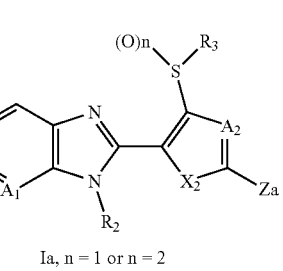

Ia, n = 1 or n = 2 wherein:

$X_{01}$ = Halogen,

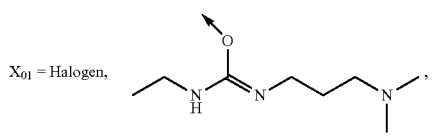

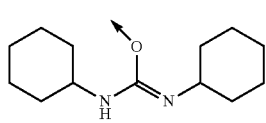

Scheme 12:

XVb (COCl)$_2$, inert solvent, e.g. CH$_2$Cl$_2$ room temp, or SOCl$_2$, CH$_2$Cl$_2$ room temp. or DCC, EDC, THF or pyridine, rt-120 deg.

XVba

VIII
optionally in the presence of an additional base, such as triethylamine or pyridine XVIb   -and/or- XVIIb PPh3, DIAD, solvent, e.g. THF r.t to 50 deg. or p. TsOH, inert solvent, e.g NMP, Microwave, rt to 180° C. or AcOH, 150° C.

Id $M_0SR_3$
Solvent e.g.
NMP, DMF, THF
Rt to 100° C.

Ib, n = 0

Oxidation

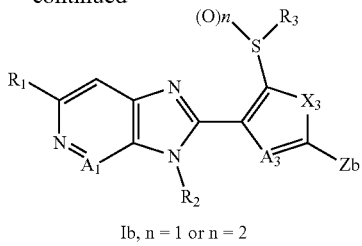

Ib, n = 1 or n = 2 wherein:

$X_{01}$ = Halogen,

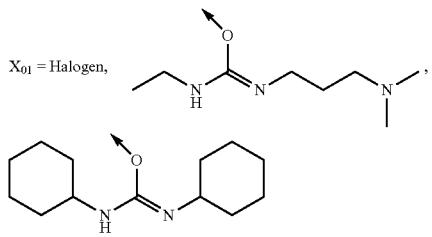

Compounds of the formula XVIa, and/or XVIIa and XVIb, and/or XVIIb or a salt thereof, may be prepared (scheme 11 and scheme 12) by;

i) activation of compound of formula XVb or XVa, by methods known to those skilled in the art and described in schemes 8 and 9, to form an activated species XVaa or XVba, wherein $X_{01}$ is halogen, preferably chlorine. For example, compounds XVaa or XVba where $X_{01}$ is halogen, preferably chlorine, are formed by treatment of XVa or XVb with, for example, oxalyl chloride $(COCl)_2$ or thionyl chloride $SOCl_2$ in the presence of catalytic quantities of N,N-dimethylformamide (DMF) in inert solvents such as methylene chloride or tetrahydrofurane at temperatures between 20 to 100° C., preferably 25° C. Alternatively, treatment of compounds of formula XVa or XVb with, for example, 1-ethyl-3-(3-dimethylaminopropyl)carbodiimide (EDC) or dicyclohexyl carbodiimide (DCC) will generate an activated species XVaa or XVba, wherein $X_{01}$ is

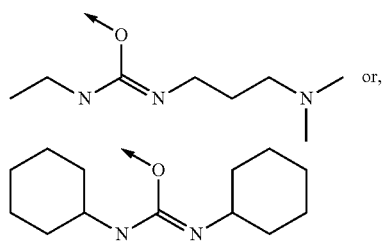

respectively, in an inert solvent, such as pyridine or tetrahydrofurane, optionally in the presence of a base, such as triethylamine, at temperatures between 25-180° C.; followed by;

ii) treatment of the activated species XVba or XVaa with a compound of formula VIII (or a salt thereof), wherein $A_1$ and $R_1$ are as described under formula I above, $X_1$ is $NR_2$, and $R_2$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl, optionally in the presence of a base, such as triethylamine or pyridine, in an inert solvents such as dichloromethane, tetrahydrofurane, dioxane or toluene, at temperatures between 0 and 80° C., to form the compounds of formula XVIa and/or XVIIa and XVIb and/or XVIIb.

Compounds of formula XVIa and/or XVIIa and XVIb and/or XVIIb may further be converted into compounds of formula Ic and Id, respectively (schemes 11 and 12), wherein $Xb_3$ is a leaving group such as fluorine, chlorine, bromine or iodine, by dehydration, e.g. by heating the compounds XVIa and/or XVIIa and XVIb and/or XVIIb in the presence of an acid catalyst, such as for example methane sulfonic acid, or para-toluene sulfonic acid (TsOH), in an inert solvent such as N-methyl pyrrolidine at temperatures between 25-180° C., preferably 100-170° C., optionally under microwave conditions, or by heating in acetic acid at temperatures between 100-180° C. Such reactions have been described previously in schemes 8 and 9. Compounds of formula Ic and Id (scheme 11 and scheme 12, respectively) can be treated with a compound of the formula $M_0SR_3$, wherein $R_3$ is as defined in formula I and $M_0$ is a metal or non-metal cation to give compounds of formula Ia or Ib, wherein n is 0. In scheme 11 and scheme 12, the cation $M_0$ is assumed to be monovalent, but polyvalent cations associated with more than one S—$R_3$ group can also be considered. Preferred cations are, for example lithium, sodium, potassium or cesium. For this transformation to work, $Xb_3$ is a leaving group like, for example, fluorine, chlorine, bromine or iodine, or an aryl- or alkylsulfonate, but many other leaving groups could be considered (for example $NO_2$). The reaction can be performed in a solvent, preferably aprotic, at temperatures below 0° C. or up to boiling temperature of the reaction mixture. Compounds of formula and Ia and Ib, wherein the substituents are described as in formula I, and n is 1 or 2, can be prepared by oxidation of compounds of formula Ic and Id. The reaction can be performed with reagents like, for example, a peracid such as peracetic acid or m-chloroperbenzoic acid, or a hydroperoxide, such as for example, hydrogen peroxide or tert-butylhydroperoxide, or an inorganic oxidant, like a monoperoxo-disulfate salt or potassium permanganate.

These reactions can be performed in various organic or aqueous solvents compatible to these conditions, by temperatures from below 0° C. up to the boiling point of the solvent system. The reactions can occur in a stepwise fashion through compounds of formula Ia or Ib (wherein n=1). Those skilled in the art will appreciate that is therefore possible to control the reaction (depending on amount of oxidant added, the temperature, and time of reaction) to allow isolation of compounds of formula Ia and Ib wherein n is equal to 1 (i.e the sulfoxides of compounds Ia and Ib) or to oxide through to compounds Ia and Ib wherein n is equal to 2 (i.e. the sulfones of compounds Ia and Ib).

As shown in scheme 13, compounds of formula Ia or Ib, wherein $R_1$ is $R_1a$ and $R_1a$ is halogen, preferably bromine or iodine, can be converted to compounds of formula Ia or Ib, wherein $R_1$ is $C_1$-$C_2$haloalkyl, by treatment of Ia or Ib with a compound of formula $W_1$ in an aprotic polar solvent, such as DMF, acetonitrile, N-methylpyrollidinone and the like, at temperatures between 20-150° C., optionally under microwave conditions. Such reactions have previously been reported in the literature (see Hartwig, J. F et al., Angew. Chem. Int. Ed. 2011, 50, 3793-3798). Similarly, compounds of formula Ia or Ib wherein $R_1$ is $C_1$-$C_2$haloalkylsufanyl, can be prepared by treatment of compounds of formula Ia or Ib, wherein $R_1b$ is halogen, preferably bromine or iodine, with a compound of formula $W_2$ in an aprotic polar solvent, such as DMF, acetonitrile, N-methylpyrollidinone and the like, at temperatures between 20-150° C., optionally under microwave conditions. Such copper alkylfluorothiolations have been reported in the literature (Angew. Chem. Int. Ed. 2013, 52, 1548-1552). Compounds of formula Ia or Ib wherein $R_1$ is $C_1$-$C_2$haloalkylsufanyl can be oxidised by methods know to those skilled in the art, for example with oxidants such as m-chloroperbenzoic, or an aqueous hydrogen peroxide solution in the presence of a catalyst, for example sodium tungstate.

Compounds of formula Ia or Ib wherein $R_1$ is $C_3$-$C_6$cycloalkyl which can be mono- or polysubstituted by substituents selected from the group consisting of halogen, cyano and $C_1$-$C_4$alkyl, can be prepared by a Suzuki coupling of a compound of formula IIIaa with a compound of formula Ia or Ib wherein $R_1$ is $R_1$a and $R_1$a is halogen, with a compound of formula IIIaa, wherein $R_1$ is $C_3$-$C_6$cycloalkyl which can be mono- or polysubstituted by substituents selected from the group consisting of halogen, cyano and $C_1$-$C_4$alkyl. In compound IIIaa, $Yb_5$ can be a boron-derived functional group, as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction is catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like for example, toluene, a mixture of 1,2-dimethoxyethane and water or of dioxane and water, preferably under inert atmosphere. The reaction temperature can preferentially range from ambient temperature to the boiling point of the reaction mixture. Such Suzuki reactions are well known to those skilled in the art and have been reviewed, for example *Angew. Chem., Int. Ed.,* 40, 2001, pp. 4544, and *Tetrahedron,* 68(3), 900-905, 2012. The chemistry is illustrated in scheme 13.

Compounds of formula IIa, required for the preparation of compounds of formula Ia (schemes 1 and 3) can be prepared as shown in scheme 14.

Scheme 14:

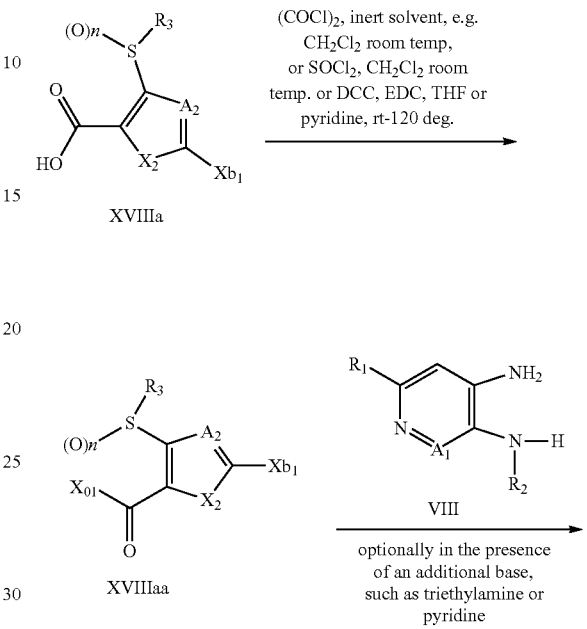

Scheme 13:

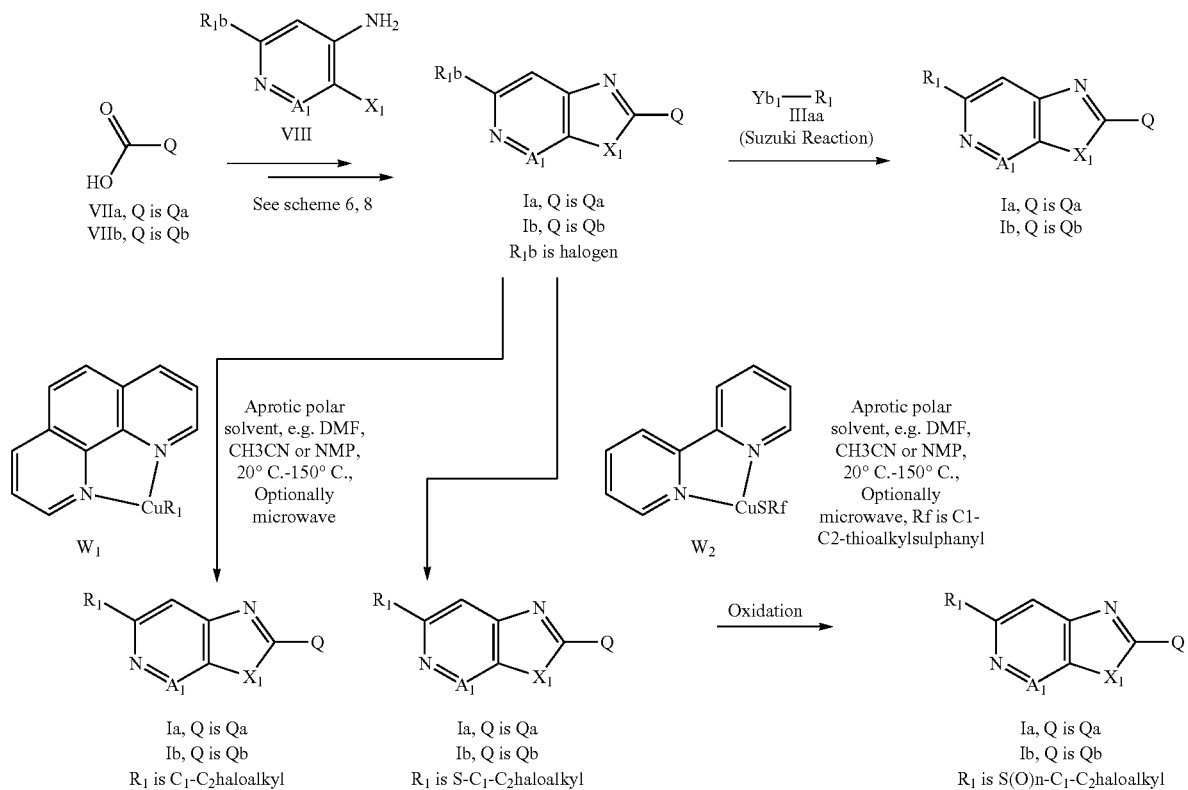

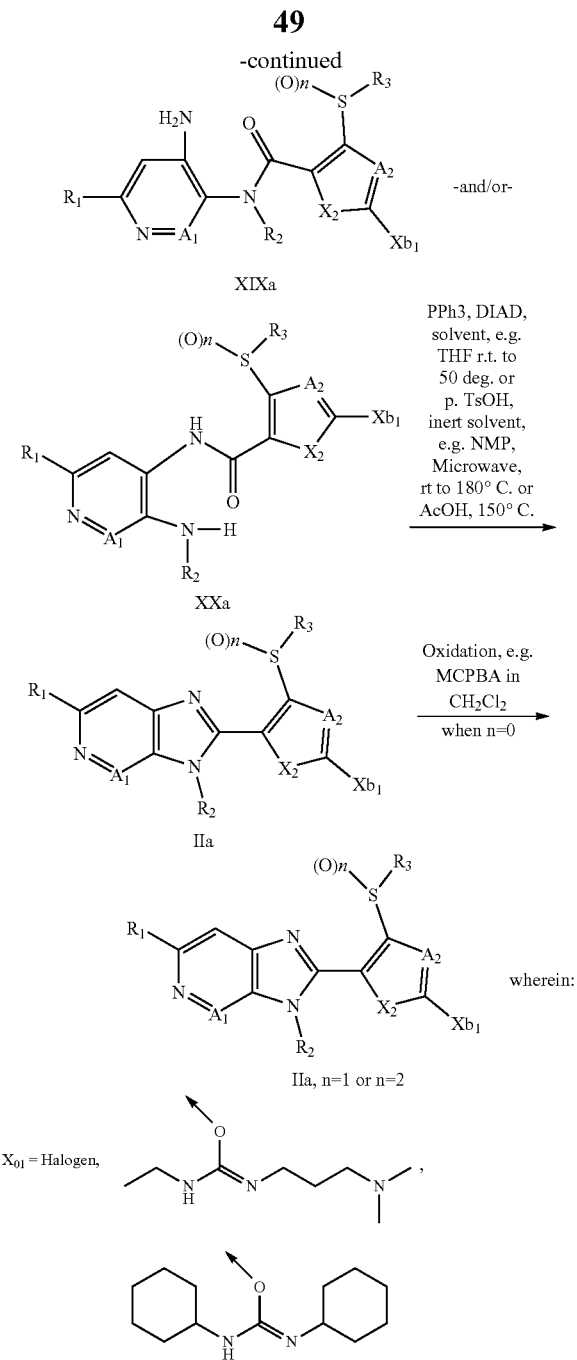

Scheme 15:

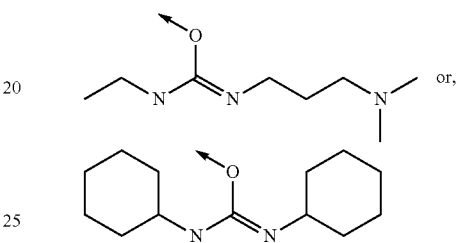

The chemistry described in scheme 14 is analogous to that described for example in scheme 11. Thus, activation of compound of formula XVIIIa, by methods known to those skilled in the art and described in scheme 11 and forms an activated species XVIIIaa, wherein $X_{01}$ is halogen, preferably chlorine, are formed by treatment of XVIIIa with, for example, oxalyl chloride $(COCl)_2$ or thionyl chloride $SOCl_2$ in the presence of catalytic quantities of N,N-dimethylformamide (DMF) in inert solvents such as methylene chloride or tetrahydrofurane at temperatures between 20 to 100° C., preferably 25° C. Alternatively, treatment of compounds of formula XVIIIa with 1-ethyl-3-(3-dimethylaminopropyl) carbodiimide (EDC) or dicyclohexyl carbodiimide (DCC) will generate an activated species XVIIIaa, wherein $X_{01}$ is wherein:

respectively, in an inert solvent, such as pyridine or tetrahydrofurane, optionally in the presence of a base, such as triethylamine, at temperatures between 25-180° C.; followed by treatment of the activated species XVIIIaa with a compound of formula VIII (or a salt thereof), wherein $A_1$ and $R_1$ are as described under formula I above, $X_1$ is $NR_2$, and $R_2$ is as defined in formula I, optionally in the presence of a base, such as triethylamine or pyridine, in an inert solvents such as dichloromethane, tetrahydrofurane, dioxane or toluene, at temperatures between 0 and 80° C., leads to the compounds of formula XIXa and/or XXa. The latter may be converted into compounds of formula IIa by dehydration, e.g. by heating the compounds XIXa and/or XXa in the presence of an acid catalyst, such as for example methane sulfonic acid, or para-toluene sulfonic acid (TsOH), in an inert solvent such as N-methyl pyrrolidine at temperatures between 25-180° C., preferably 100-170° C., optionally under microwave conditions, or by heating in acetic acid at temperatures between 100-180° C. Such reactions have been described previously.

Intermediates of formula XVIIIa may be prepared as shown in scheme 15:

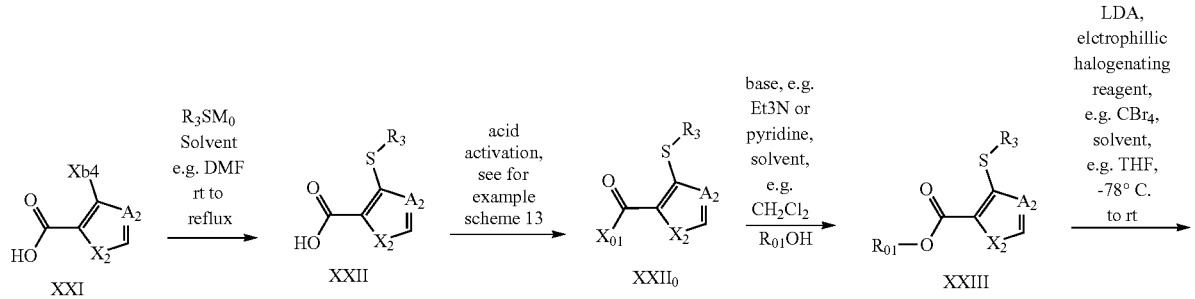

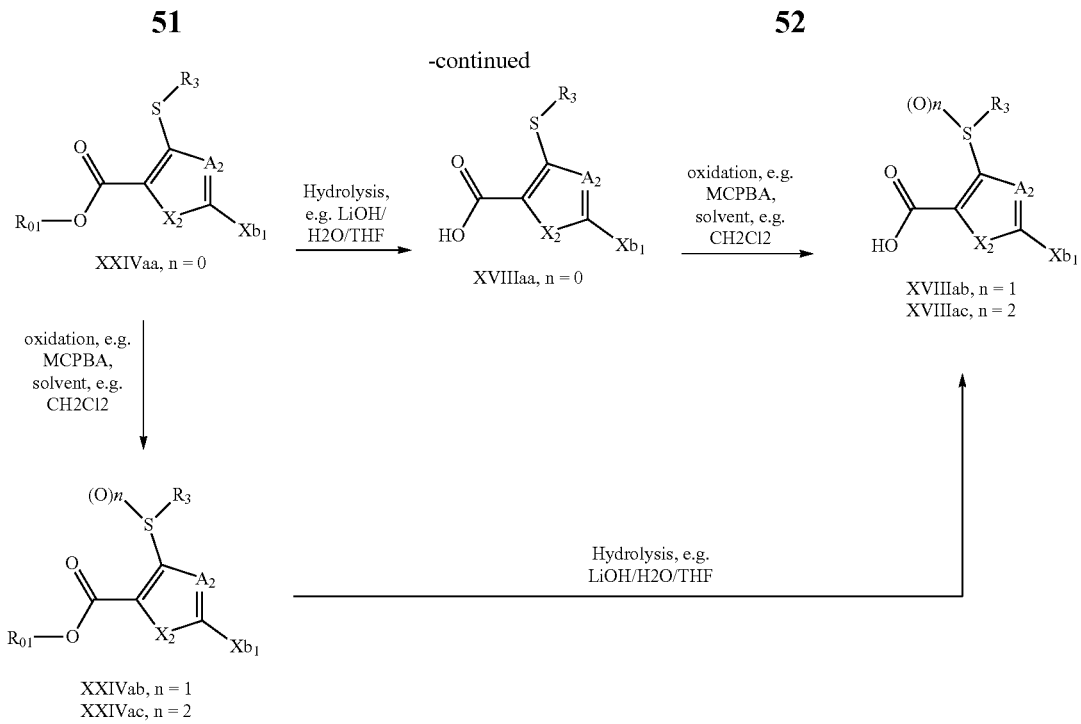

As shown in scheme 15, compounds of formula XXI, wherein $A_2$ and $X_2$ are as described in formula I, and $Xb_4$ is halogen, are converted to compounds of formula XXII by treatment with compounds of the formula $M_0SR_3$, wherein $M_0$, and $R_3$ are as previously described, under the conditions described in scheme 11, to give compounds of formula XXII. Compounds of formula XXII can be converted to the esters of formula XXIII, by treatment of the activated species $XXII_0$ with an alcohol $R_{01}OH$, wherein $R_{01}$ is C1-C4alkyl, in the presence of a base, for example triethylamine of pryridine, optionally in the presence of a solvent, such as methylene chloride or tetrahydrofurane. Activation of acids is known to those skilled in the art and has been previously described here for example in scheme 11. Compounds of formula XXIII can be deprotonated with a strong base, such as lithiumdiisopropylamide, in an inert solvent such as ether or tetrahydrofurane, at temperatures between −78° C. to rt, and the anion formed quenched with an electrophilic halogen source such as bromine, carbon tetrabromide and the like, to give compounds of formula XXIVaa, wherein $A_2$ and $X_2$ are as described under formula I. Compounds of formula XXIVaa can be hydrolyzed by methods known to those skilled in the art, for example with an alkaline earth metal base such as lithium hydroxide, in a mixture of water and a water miscible solvent such as THF or acetone to give compounds of formula XVIIIaa. Compounds of formula XVIIIaa can be oxidized to compounds of formula XVIIIab (n=1, i.e sulfoxides), or XVIIIac (n=2, i.e sulfones) by methods known to those skilled in the art and described for example in scheme 11. Alternatively, compounds of formula XXIVaa can be first oxidized to compounds of formula XXIVab (sulfoxides) or XXIVac (sulfones), and these then in turn hydrolyzed to compounds of formula XVIIIab (sulfoxides) or XVIIIac (sulfones), respectively. Intermediates of formula VIIa can be prepared (as shown in scheme 16) from compounds of formula VIIab, wherein $A_2$, $R_3$, $X_2$, and $Xb_1$, are as previously defined, $R_{01}$ is $C_1$-$C_4$alkyl and n is 0, 1, or 2, by methods known to those skilled in the art, for example by treatment with an alkaline earth metal base, such as lithium hydroxide, typically in water with sufficient miscible organic solvent, for example THF or acetone, to dissolve compounds of the formula VIIab. Compounds VIIab can be prepared by a Suzuki reaction, which involves for example, reacting compounds of formula XXIVa, XXIVb, or XXIVc (preferably XXIVc), wherein $Xb_1$ is a leaving group like, for example, chlorine, bromine or iodine, with compounds of formula IIIa1, wherein $Y_{b1}$ can be a boron-derived functional group, as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction can be catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water or of dioxane and water, preferably under inert atmosphere. The reaction temperature can preferentially range from ambient temperature to the boiling point of the reaction mixture. Such Suzuki reactions are well known to those skilled in the art and have been reviewed, for example *J. Orgmet. Chem.* 576, 1999, 147-168.

Scheme 16:

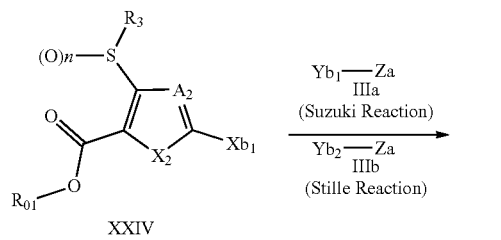

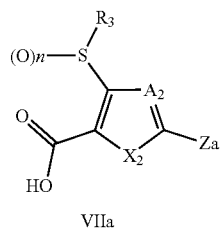

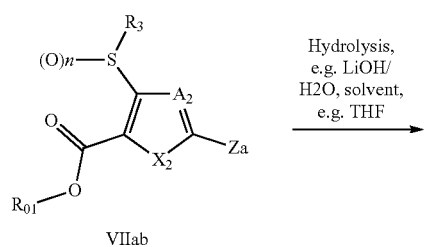

Alternatively (as shown above in scheme 16) compounds of formula VIIab can be prepared by a Stille reaction of compounds of formula IIIb1 wherein $Y_{b2}$ is a trialkyl tin derivative, preferably tri-n-butyl tin, with compounds of formula XXIV. Such Stille reactions are usually carried out in the presence of a palladium catalyst, for example tetrakis (triphenylphosphine)palladium(0), or (1,1'bis(diphenyl-phosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136.

Intermediates VIIa, VIIab, and, XVa can be prepared as shown in scheme 17:

Scheme 17:

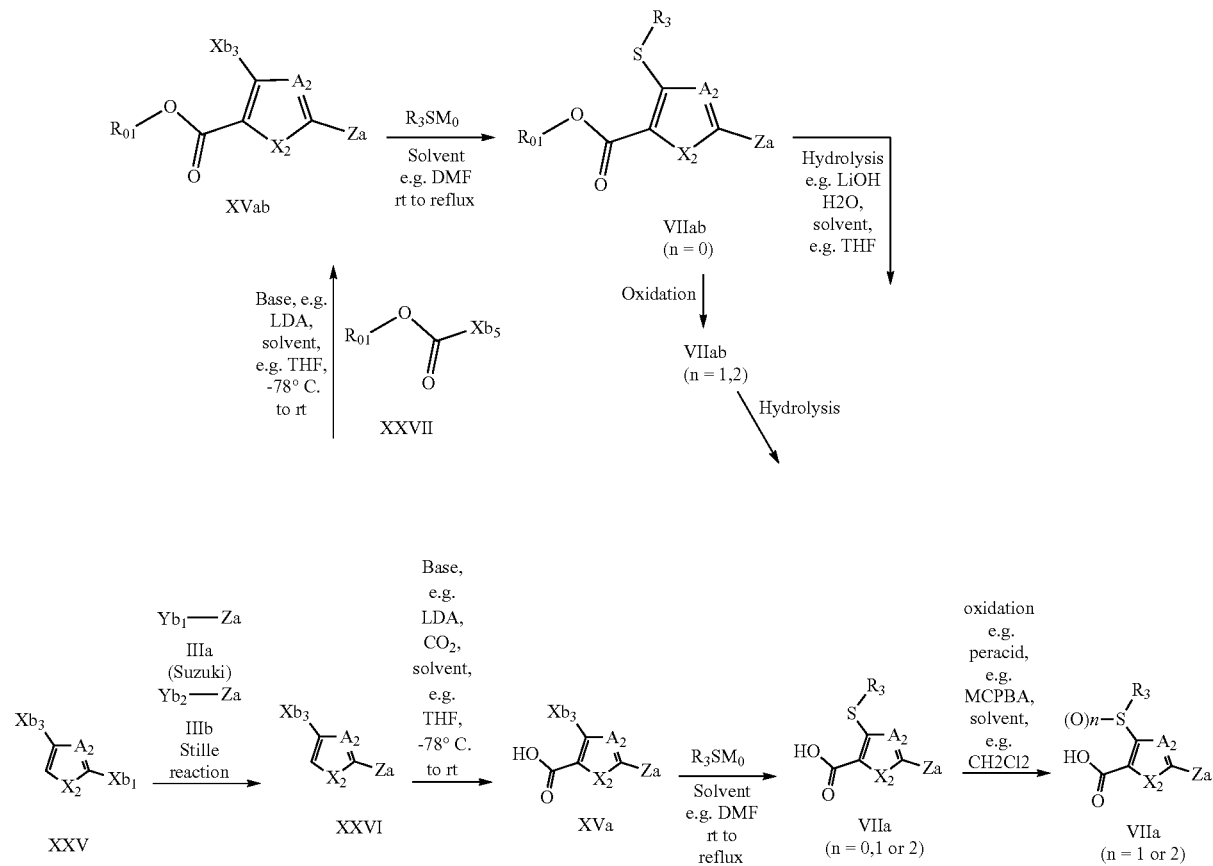

As shown in scheme 17, a compound of formula XXV, wherein $Xb_3$ and $Xb_1$ are as previously defined, can be reacted with a boronic acid, or boronate ester of formula IIIa1 under Suzuki conditions, or with a compound of formula IIIb under Stille conditions, as previously described in for example scheme 1, to give compounds of formula XXVI, wherein $A_2$, X2, and Za are as described in formula I, and $Xb_3$ is a leaving group such as fluorine, chlorine, bromine or iodine. Compounds of formula XXVI can be deprotonated with a strong base, such as lithiumdiisopropylamide, in an inert solvent such as ether or tetrahydrofurane, at temperatures between −78° C. to rt, and the anion formed quenched with carbon dioxide to give carboxylic acids of formula XVa, wherein $A_2$ and $X_2$, and Za are as described under formula I. Alternatively, the anion can be quenched with an electrophile of formula XXVII, wherein $Xb_5$ is a leaving group, such as halogen or methoxy, $R_{O1}$ is $C_1$-$C_4$alkyl in an inert solvent such as ether or tetrahydrofurane, at temperatures between −78° C.-ambient temperature, to give compounds of formula XVab, where the substituents are as previously described. Compounds of formula XVa can be used directly as intermediates in the synthesis of compounds of formula I, or converted to compounds of formula VIIa by treatment with $M_0SR_3$ and subsequent oxidation as previously described. Those skilled in the art will recognize that compounds of formula VIIb can be obtained in similar manner to those described in schemes 15, 16 and 17 for compounds of formula VIIa.

A large number of compounds of the formula Va and Vb are commercially available or can be prepared by those skilled in the art. Many chemical transformations, also well known by those skilled in the art, can be used to access boronic acid derivatives of formula IIIa1, starting from various and easily available starting materials, as for example, to cite only a few (scheme 18), hydrogen abstraction on a heteroaromatic compound of the formula Va wherein Xb2 is hydrogen, with a strong base (step A), like butyl lithium or lithium diisopropylamide or (i-PrMgCl.LiCl), followed by reaction of the metallated intermediate of the formula IIIaa1, wherein $Wb_2$ is a metal such as $Li^+$ or $MgCl^+$ for example, with, for example, a trialkylborate (step B, to give IIIa1), or a tri-n-butyl tin chloride (step B, to give IIIb1). Another way to access an organometal intermediate of the formulae IIIa1 is by metal-halogen exchange of compound of formula Va with an organometallic species (step C), using for example butyl lithium or an organo magnesium compound, or direct metallation with a metal, like magnesium.

Introduction of a pinacolborate functional group via a palladium catalyzed reaction with bispinacol diborane, or hexa-n-butyldistannane (to give IIIb1), on a compound of the formula Va, wherein Xb2 is halogen, is another common strategy (scheme 18, step D). In the compounds of formula IIIa1 within scheme 18, Za have the values defined for the formula I. A person skilled in the art will be able to select an adequate preparation method to access compounds of formula IIIa1 (and IIIb1) depending on the values of Za (and Zb). The chemistry is illustrated in scheme 18 only for compounds of formula IIIa1, and IIIb1, but those skilled in the art will appreciate that exactly the same chemistry can be applied to form compounds of formula IIIa2 and IIIb2 from compounds of formula Vb using the very same strategies.

Scheme 18:

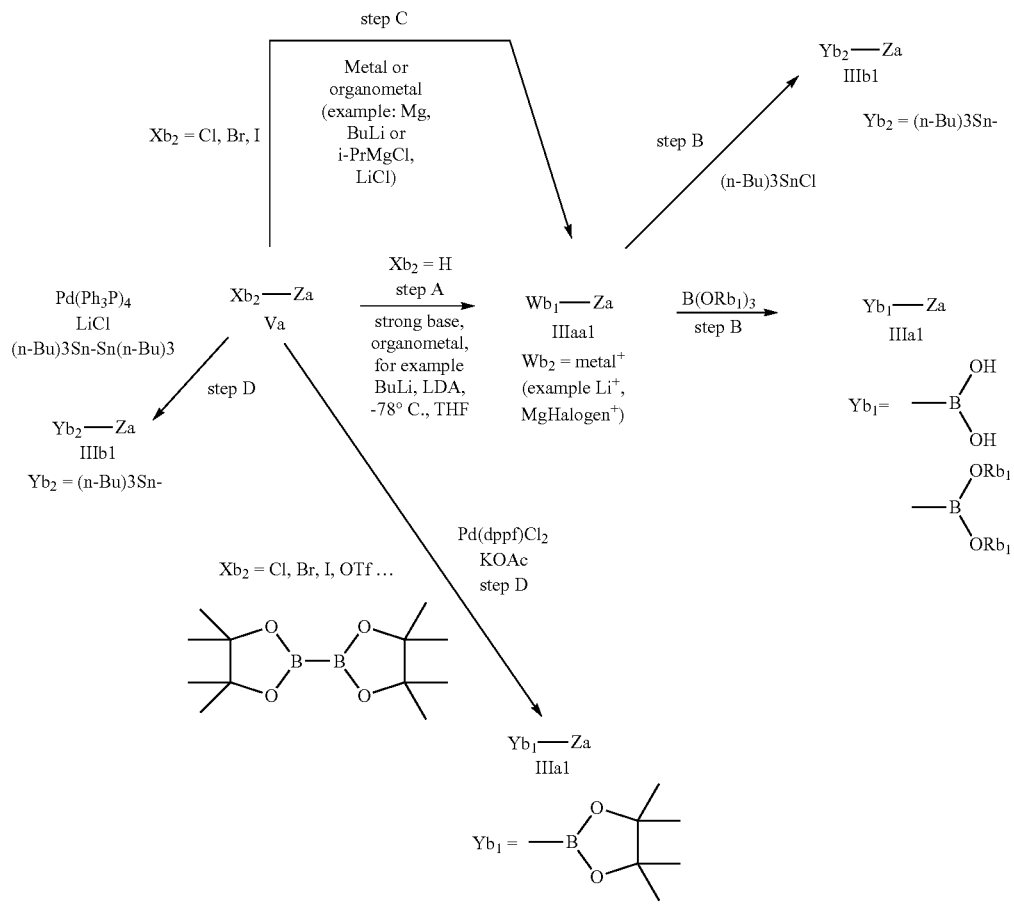

Compounds of formula IVa, wherein $A_1$, $X_1$, $A_2$, $X_2$, $R_1$, $R_3$, and n are as described in formula I, can be prepared from compounds of formula IIa (scheme 19), wherein $A_1$, $X_1$, $A_2$, $X_2$, $R_1$, $R_3$, and n are as described in formula I. Thus, compounds of formula IIa, wherein $Xb_1$ is chlorine, bromine or iodine, can be treated with an organometallic species like, for example, butyl lithium or an organomagnesium compound, to generate an intermediate compound of the formula IVaa, wherein $Wb_3$ is as defined in the scheme, via metal-halogen exchange. This reaction is preferentially performed in an anhydrous aprotic solvent, such as THF, at low temperature (between −120° C. and 0° C.), preferentially between −110° C. and −60° C.). The intermediate organometal compound of formula IVaa is preferably directly converted into compound of formula IVa by reaction with a boronate compound $B(OR_{b2})_3$, wherein $R_{b2}$ is a $C_1$-$C_4$alkyl group. Depending on nature of the boronate, the reaction treatment conditions and the workup conditions, the boronic acid IVa, wherein $Yb_3$ is —$B(OH)_2$, or a dialkylboronate IV, wherein $Yb_3$ is —$B(OR_{b2})_2$, can be formed. Those skilled in the art will appreciate that compounds of formula IVb can be prepared from compounds of formula IIb in exactly the same manner.

Introduction of a pinacolborate functional group via a palladium catalyzed reaction with bispinacol diborane on compound of the formula IIa, wherein Xb1 is chlorine, bromine, iodine or triflate, is another common strategy (scheme 19). In the compounds of formula IIa within scheme 19, $A_1$, $X_1$, $A_2$, $X_2$, $R_1$, $R_3$, and n have the values defined for the formula I, and Xb1 is chlorine, bromine, fluorine, iodine or triflate. A person skilled in the art will be able to select an adequate preparation method to access compounds of formula IVa from IIA depending on the values $A_1$, $X_1$, $A_2$, $X_2$, $R_1$, $R_3$, and n. Those skilled in the art will recognize that compounds of formula IVb containing a pinacolborate functional group can be obtained from compounds of formula IIb in an analogous manner.

The very similar preparation methods described in scheme 19 may be applied for the synthesis of intermediates of the formula VIa and VIb, but in this case instead of using boronic compounds e.g. of formula $B(OR_{b2})_3$, those skilled in the art would know to use a tin compound of formula (n-butyl)$_3$SnCl (as described as for example in *Eu. J. Chem.*, 4098-4104, 20, 2014) or instead of bispinacol diborane, hexabutylditin (as described in for example Eur. Pat. Appl., 2749561, 2014). This is illustrated for compound VIa in scheme 20.

Scheme 19:

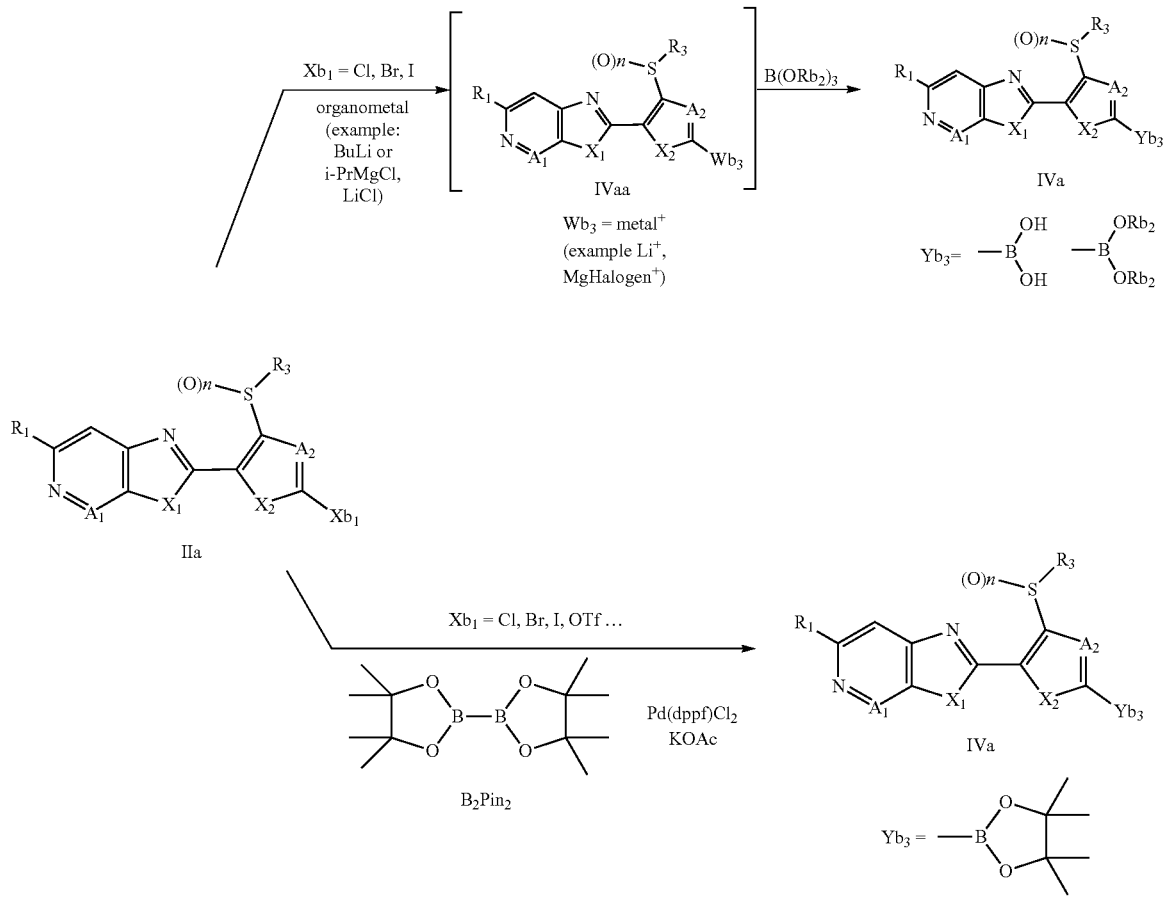

Scheme 20.

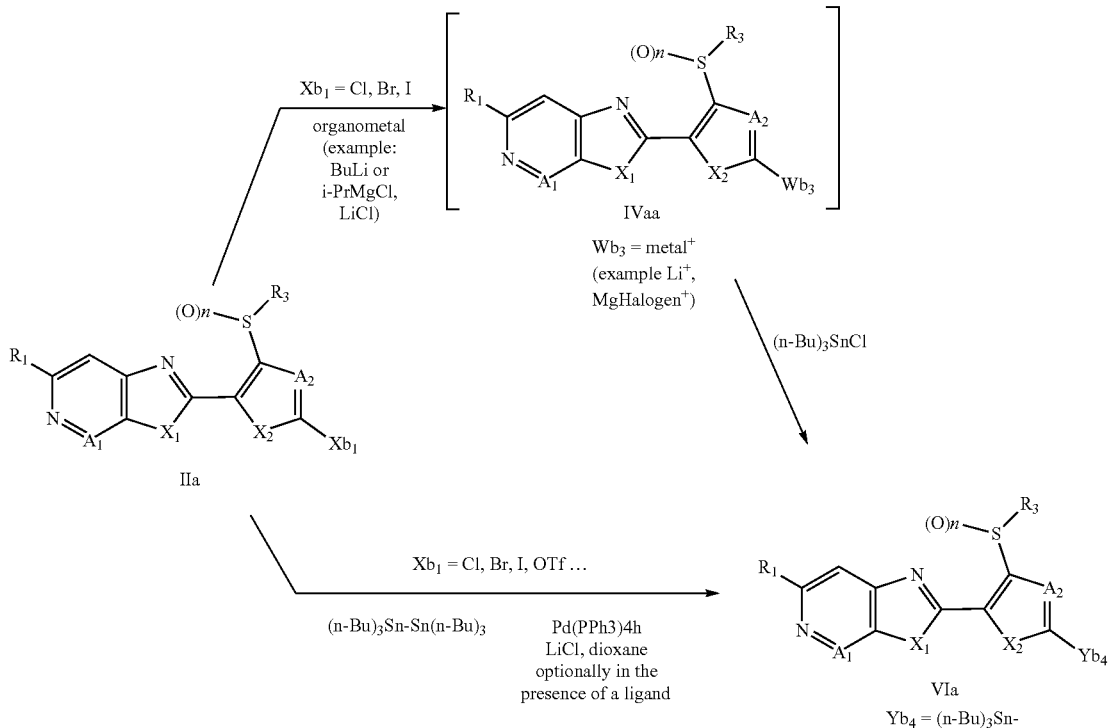

Intermediates of formula VIII and VIIIa are known, or can be prepared by those skilled in the art or using syntheses analogous to those described previously. For example compounds of formula VIII,

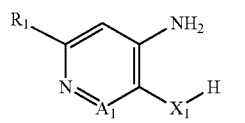

(VIII)

wherein $R_1$ is halogen, preferably bromine, and $X_1$ is $NR_{2a}$, wherein $R_{2a}$ is $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl, can be prepared the methods shown, for example, in scheme 21

Scheme 21:

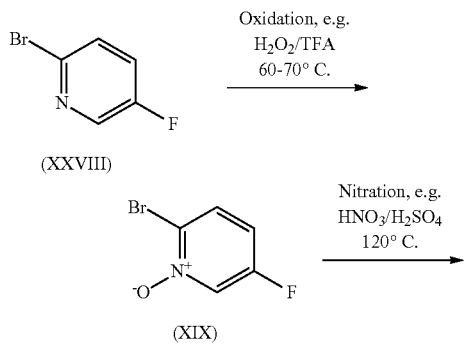

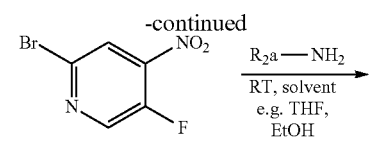

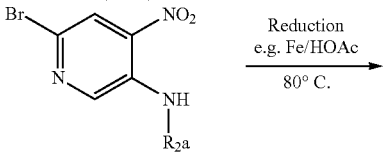

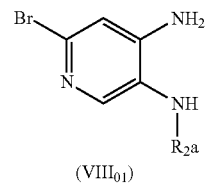

In scheme 21, a compound of formula (XXVIII) is oxidized to a compound of formula XIX by methods known to those skilled in the art, for example with hydrogen peroxide in trifluoroacetic acid and the like. The compounds of formula XIX can be nitrated by methods described for example in "Nitro Compounds, Aromatic" Ullmann's Encyclopedia of Industrial Chemistry, 2005, Wiley-VCH, Weinheim to give compounds of formula XXX. Compounds of formula XXX can be converted to compounds of formula XXXI by treatment with a compound of formula $R_{2a}$—$NH_2$, wherein $R_{2a}$ is $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl. The reaction is generally conducted in the presence of a solvent, such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof. The reaction temperature of the reaction is generally within a range of −80° C. to 50° C. The products of formula XXXI, can be reduced to compounds of formula $XVIII_{01}$ by methods known to those skilled in the art, for example with a metal in acidic medium, for example Fe in acetic acid or hydrochloric acid. Such reductions of $NO_2$ groups have been described for example in Org. Synth.; Coll. Vol. 5: 346, 1973.

Compounds of formula VIII, wherein $X_1$ is $NR_2$, $A_1$ is CH and $R_1$ is trifluoromethyl have been described in WO 2015/000715. Compounds of formula VIIIa, have been described in WO 2014/148451 and WO 2014/142292. An improved synthesis of compounds of formula $VIIIa_{01}$ and of com-

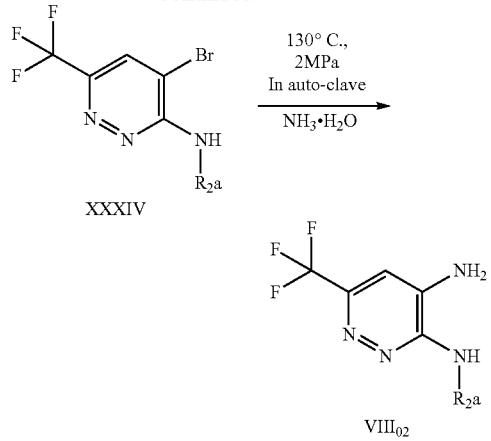

Scheme 23:

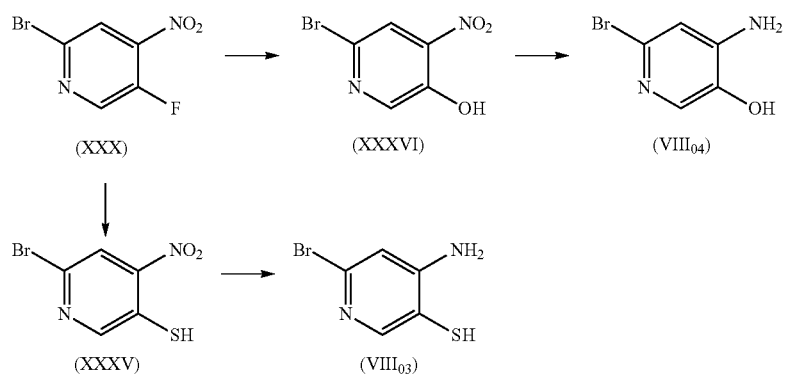

pounds $VIII_{02}$ is shown in scheme 22; Treatment of compounds of formula XXXII with compounds formula $R_{2a}$—$NH_2$, wherein $R_{2a}$ is as defined above, in an inert solvent such as THF, or EtOH, leads to compounds of formula XXXXIII. Halogenation of compounds of formula XXXIII with for example bromine in acetonitrile leads to compounds of formula XXXIV. The bromine in compounds of formula XXXIV can be substituted with ammonia at temperatures between 100-150° C. at a pressure of 2M Pa, as described in scheme 22.

Scheme 22:

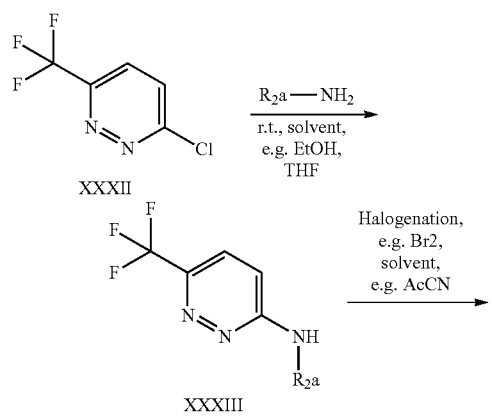

The compound of formula VIII wherein $X_1$ is SH (i.e. compounds of formula $VIII_{03}$) can be produced by reacting a compound of formula XXX (scheme 23) with a sulfating agent. Examples of the sulfating agent to be used in the reaction include sodium sulfide, sodium sulfide 9-hydrate, and thiourea. The reaction may be conducted in the presence of a base. Examples of the base to be used in the reaction include inorganic bases such as potassium carbonate, cesium carbonate, and tripotassium phosphate; and organic bases, for example triethylamine. The reaction is generally conducted in the presence of a solvent. Examples of the solvent to be used in the reaction include water; alcohols such as methanol and ethanol; ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; carboxylic acids such as acetic acid; and mixtures thereof. Similar reactions have been described in the literature (see WO 2010/055004). Reduction of the nitro group in compound XXXV as described in scheme 21 leads to compounds of formula $VIII_{03}$. In a similar manner, compounds of formula VIII wherein $X_1$ is OH (i.e compounds of formula $VIII_{04}$), can be prepared from compounds of formula XXX by treatment with aqueous base such as sodium hydroxide, or lithium hydroxide, under conditions known to those skilled in the art. The nitro group in compounds XXXVI can then be reduced yield compounds of formula $VIII_{04}$ using for example Fe in acetic acid or hydrochloric acid, as described in scheme 21.

For preparing all other compounds of the formula (I) functionalized according to the definitions of formula I, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and herein below, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615. It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 38 below can be prepared according to the methods described above. The examples which follow are intended to illustrate the invention and show preferred compounds of formula I. "Ph" represents the phenyl group. Free radicals represent methyl groups.

TABLE X

This table discloses the 42 substituent designations X.001 to X.042 for the formulae (Iaa), (Iab), (Iac), (Iad), (Iae) and (Iaf) which are disclosed after Table X. The arrow denotes the point of attachment of the substituent to the 5 membered heterocycle.

| Comp. No | Zx |
|---|---|
| X.001 | phenyl |
| X.002 | 2-Cl-phenyl |
| X.003 | 3-Cl-phenyl |
| X.004 | 4-Cl-phenyl |
| X.005 | 2-CF₃-phenyl |
| X.006 | 3-CF₃-phenyl |
| X.007 | 4-CF₃-phenyl |
| X.008 | 5-Cl-pyridin-2-yl |

TABLE X-continued

This table discloses the 42 substituent designations X.001 to X.042 for the formulae (Iaa), (Iab), (Iac), (Iad), (Iae) and (Iaf) which are disclosed after Table X. The arrow denotes the point of attachment of the substituent to the 5 membered heterocycle.

| Comp. No | Zx |
|---|---|
| X.009 | 3-Cl-pyridin-2-yl |
| X.010 | 3,5-diCl-pyridin-2-yl |
| X.011 | 5-F-pyridin-2-yl |
| X.012 | 3-F-pyridin-2-yl |
| X.013 | 3,5-diF-pyridin-2-yl |
| X.014 | 3-F-5-CF₃-pyridin-2-yl |
| X.015 | 5-Cl-pyrimidin-2-yl |
| X.016 | pyrimidin-2-yl |
| X.017 | 3-CF₃-pyrazol-1-yl |
| X.018 | 3-Cl-pyrazol-1-yl |
| X.019 | 4-CF₃-pyrazol-1-yl |

TABLE X-continued

This table discloses the 42 substituent designations X.001 to X.042 for the formulae (Iaa), (Iab), (Iac), (Iad), (Iae) and (Iaf) which are disclosed after Table X. The arrow denotes the point of attachment of the substituent to the 5 membered heterocycle.

| Comp. No | Zx |
|---|---|
| X.020 | 4-chloro-1H-pyrazol-1-yl |
| X.021 | cyclopropyl |
| X.022 | 1-cyanocyclopropyl |
| X.023 | 1-methylcyclopropyl |
| X.024 | 1-(trifluoromethyl)cyclopropyl |
| X.025 | (E)-2-(2-(trifluoromethyl)phenyl)vinyl |
| X.026 | 2-(2-(trifluoromethyl)phenyl)ethyl |
| X.027 | (2-(trifluoromethyl)phenyl)ethynyl |
| X.028 | 5-cyanopyrimidin-2-yl |
| X.029 | 4-cyanopyrimidin-2-yl |
| X.030 | 5-cyanopyridin-2-yl |
| X.031 | 4-cyanopyridin-2-yl |
| X.032 | 3-cyano-1H-pyrazol-1-yl |
| X.033 | 4-cyano-1H-pyrazol-1-yl |
| X.034 | 4-(trifluoromethyl)pyridin-2-yl |
| X.035 | 3-cyanophenyl |
| X.036 | 4-cyanophenyl |
| X.037 | 4-chloropyridin-2-yl |
| X.038 | pyridin-2-yl |
| X.039 | 5-(trifluoromethyl)-1,3,4-oxadiazol-2-yl |
| X.040 | 3,5-difluorophenyl |

TABLE X-continued

This table discloses the 42 substituent designations X.001 to X.042 for the formulae (Iaa), (Iab), (Iac). (Iad), (Iae) and (Iaf) which are disclosed after Table X. The arrow denotes the point of attachment of the substituent to the 5 membered heterocycle.

| Comp. No | Zx |
|---|---|
| X.041 | 3-fluorophenyl |
| X.042 | 3,5-dichlorophenyl |

Table 1:

This table discloses the 42 compounds 1.001 to 1.042 of the formula (Iaa):

(Iaa)

wherein n is 0, and $R_1$ is $CF_3$, $R_3$ is ethyl, $R_4$ is hydrogen, and Zx is as defined in lines X.001-X.042 in table X. For example, compound 1.004 has the following structure:

(1.004)

Table 2:

This table discloses the 42 compounds 2.001 to 2.042 of the formula (Iaa) wherein n is 2, and $R_1$ is $CF_3$, $R_3$ is ethyl, $R_4$ is hydrogen, and Zx is as defined in lines X.001-X.042 in table X.

Table 3:

This table discloses the 42 compounds 3.001 to 3.042 of the formula (Iaa) wherein n is 0, and $R_1$ is $CF_2CF_3$, $R_3$ is ethyl, and Zx is as defined in lines X.001-X.042 in table X.

Table 4:

This table discloses the 42 compounds 4.001 to 4.042 of the formula (Iaa) wherein n is 2, and $R_1$ is $CF_2CF_3$, $R_3$ is ethyl, $R_4$ is hydrogen, and Zx is as defined in lines X.001-X.042 in table X.

Table 5:

This table discloses the 42 compounds 5.001 to 5.042 of the formula (Iaa) wherein n is 0, and $R_1$ is $OCF_3$, $R_3$ is ethyl, $R_4$ is hydrogen and Zx is as defined in lines X.001-X.042 in table X.

Table 6:

This table discloses the 42 compounds 6.001 to 6.042 of the formula (Iaa) wherein n is 2, and $R_1$ is $OCF_3$, $R_3$ is ethyl, $R_4$ is hydrogen and Zx is as defined in lines X.001-X.042 in table X.

Table 7:

This table discloses the 42 compounds 7.001 to 7.042 of the formula (Iaa) wherein n is 0, and $R_1$ is $SCF_3$, $R_3$ is ethyl, $R_4$ is hydrogen and Zx is as defined in lines X.001-X.042 in table X.

Table 8:

This table discloses the 42 compounds 8.001 to 8.042 of the formula (Iaa) wherein n is 2, and $R_1$ is $SCF_3$, $R_3$ is ethyl, $R_4$ is hydrogen and Zx is as defined in lines X.001-X.042 in table X.

Table 9:

This table discloses the 42 compounds 9.001 to 9.042 of the formula (Iaa) wherein n is 0, and $R_1$ is $SOCF_3$, $R_3$ is ethyl, $R_4$ is hydrogen and Zx is as defined in lines X.001-X.042 in table X.

Table 10:

This table discloses the 42 compounds 10.001 to 10.042 of the formula (Iaa) wherein n is 2, and $R_1$ is $SOCF_3$, $R_3$ is ethyl, $R_4$ is hydrogen and Zx is as defined in lines X.001-X.042 in table X.

Table 11:

This table discloses the 42 compounds 11.001 to 11.042 of the formula (Iaa) wherein n is 0, and $R_1$ is $SO_2CF_3$, $R_3$ is ethyl, $R_4$ is hydrogen and Zx is as defined in lines X.001-X.042 in table X.

Table 12:

This table discloses the 42 compounds 12.001 to 12.042 of the formula (Iaa) wherein n is 2, and $R_1$ is $SO_2CF_3$, $R_3$ is ethyl, $R_4$ is hydrogen and Zx is as defined in lines X.001-X.042 in table X.

Table 13:

This table discloses the 42 compounds 13.001 to 13.042 of the formula (Iaa) wherein n is 0, and $R_1$ is Br, $R_3$ is ethyl, $R_4$ is hydrogen and Zx is as defined in lines X.001-X.042 in table X.

Table 14:

This table discloses the 42 compounds 14.001 to 14.042 of the formula (Iaa) wherein n is 2, and $R_1$ is Br, $R_3$ is ethyl, $R_4$ is hydrogen and Zx is as defined in lines X.001-X.042 in table X.

Table 15:

This table discloses 1 compound 15.001 of the formula (Iaa):
wherein n is 0, and $R_1$ is $CF_3$, $R_3$ is ethyl, $R_4$ is Cl and Za is as defined in line X.004 in table X.

Table 16:

This table discloses 1 compound 16.001 of the formula (Iaa) wherein n is 2, and $R_1$ is $CF_3$, $R_3$ is ethyl, $R_4$ is Cl and Za is as defined in line X.004 in table X.

Table 17:

This table discloses the 42 compounds 17.001 to 17.042 of the formula (Iaa) wherein n is 0, and $R_1$ is $CF_2CF_3$, $R_3$ is ethyl, $R_4$ is hydrogen and Zx is as defined in lines X.001-X.042 in table X.

Table 18:

This table discloses the 42 compounds 18.001 to 18.042 of the formula (Iaa) wherein n is 2, and $R_1$ is $CF_2CF_3$, $R_3$ is ethyl, $R_4$ is hydrogen and Zx is as defined in lines X.001-X.042 in table X.

Table 19:

This table discloses the 42 compounds 19.001 to 19.042 of the formula (Iab):

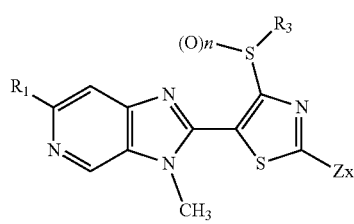
(Iab)

wherein n is 0, and $R_1$ is $CF_3$, $R_1$ is ethyl, and Zx is as defined in lines X.001-X.042 in table X. For example, compound 19.017 has the following structure:

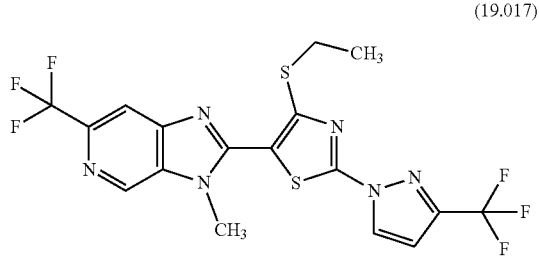 [SMILES: CCSc1nc(-n2ccc(C(F)(F)F)n2)sc1-c1nc2cc(C(F)(F)F)ncc2n1C]
(19.017)

Table 20:

This table discloses the 42 compounds 20.001 to 20.042 of the formula (Iab) wherein n is 2, and $R_1$ is $CF_3$, $R_3$ is ethyl, and Zx is as defined in lines X.001-X.042 in table X.

Table 21:

This table discloses the 42 compounds 21.001 to 21.042 of the formula (Iab) wherein n is 0, and $R_1$ is $CF_2CF_3$, $R_3$ is ethyl, and Zx is as defined in lines X.001-X.042 in table X.

Table 22:

This table discloses the 42 compounds 22.001 to 22.042 of the formula (Iab) wherein n is 2, and $R_1$ is $CF_2CF_3$, $R_3$ is ethyl, and Zx is as defined in lines X.001-X.042 in table X.

Table 23:

This table discloses the 42 compounds 23.001 to 23.042 of the formula (Iab) wherein n is 0, and $R_1$ is $SCF_3$, $R_3$ is ethyl, and Zx is as defined in lines X.001-X.042 in table X.

Table 24:

This table discloses the 42 compounds 24.001 to 24.042 of the formula (Iab) wherein n is 2, and $R_1$ is $SCF_3$, $R_3$ is ethyl, and Zx is as defined in lines X.001-X.042 in table X.

Table 25:

This table discloses the 42 compounds 25.001 to 25.042 of the formula (Iac):

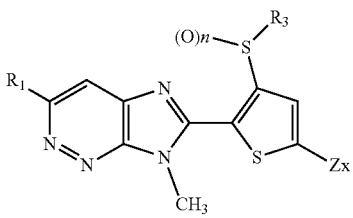
(Iac)

wherein n is 0, and $R_1$ is $CF_3$, $R_3$ is ethyl, and Zx is as defined in lines X.001-X.042 in table X. For example, compound 25.021 has the following structure:

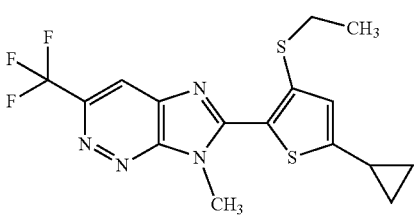
(25.021)

Table 26:

This table discloses the 42 compounds 26.001 to 26.042 of the formula (Iac) wherein n is 2, and $R_1$ is $CF_3$, $R_3$ is ethyl, and Zx is as defined in lines X.001-X.042 in table X.

Table 27:

This table discloses the 42 compounds 27.001 to 27.042 of the formula (Iac) wherein n is 0, and $R_1$ is $CF_2CF_3$, $R_3$ is ethyl, and Zx is as defined in lines X.001-X.042 in table X.

Table 28:

This table discloses the 42 compounds 28.001 to 28.042 of the formula (Iac) wherein n is 2, and $R_1$ is $CF_2CF_3$, $R_3$ is ethyl, and Zx is as defined in lines X.001-X.042 in table X.

Table 29:

This table discloses the 42 compounds 29.001 to 29.042 of the formula (Iac) wherein n is 0, and $R_1$ is $SCF_3$, $R_3$ is ethyl, and Zx is as defined in lines X.001-X.042 in table X.

Table 30:

This table discloses the 42 compounds 30.001 to 30.042 of the formula (Iac) wherein n is 2, and $R_1$ is $SCF_3$, $R_3$ is ethyl, and Zx is as defined in lines X.001-X.042 in table X.

Table 31:

This table discloses the 42 compounds 31.001 to 31.042 of the formula (Iad):

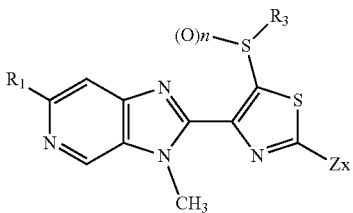
(Iad)

wherein n is 0, and $R_1$ is $CF_3$, $R_3$ is ethyl, and Zx is as defined in lines X.001-X.042 in table X. For example, compound 31.016 has the following structure:

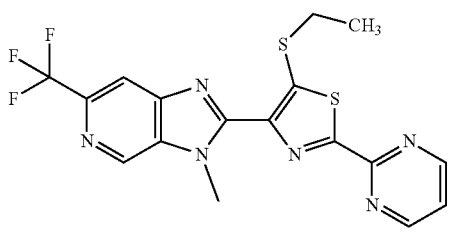

(31.016)

Table 32:

This table discloses the 42 compounds 32.001 to 32.042 of the formula (Iad) wherein n is 2, $R_1$ is $CF_3$, $R_3$ is ethyl, and Zx is as defined in lines X.001-X.042 in table X.

Table 33:

This table discloses the 42 compounds 33.001 to 33.042 of the formula (Iad) wherein n is 0, $R_1$ is $SCF_3$, $R_3$ is ethyl, and Zx is as defined in lines X.001-X.042 in table X.

Table 34:

This table discloses the 42 compounds 34.001 to 34.042 of the formula (Iad) wherein n is 2, $R_1$ is $SCF_3$, $R_3$ is ethyl, and Zx is as defined in lines X.001-X.042 in table X.

Table 35:

This table discloses the 42 compounds 35.001 to 35.042 of the formula (Iae):

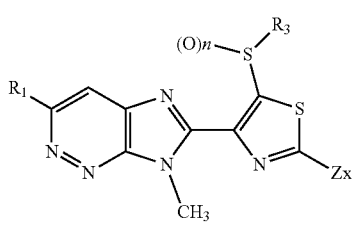

(Iae)

wherein n is 0, and $R_1$ is $CF_3$, $R_3$ is ethyl, and Zx is as defined in lines X.001-X.042 in table X. For example, compound 35.024 has the following structure:

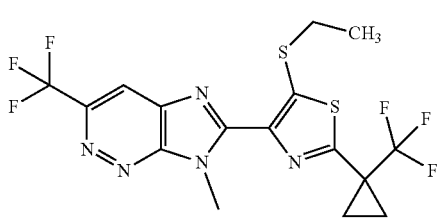

(35.024)

Table 36:

This table discloses the 42 compounds 36.001 to 36.042 of the formula (Iae) wherein n is 2, $R_1$ is $CF_3$, $R_3$ is ethyl, and Zx is as defined in lines X.001-X.042 in table X.

Table 37:

This table discloses the 42 compounds 37.001 to 37.042 of the formula (Iaf):

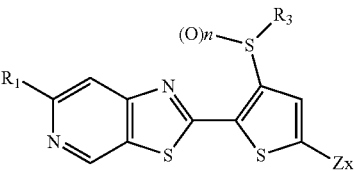

(Iaf)

wherein n is 0, and $R_1$ is $CF_3$, $R_3$ is ethyl, and Zx is as defined in lines X.001-X.042 in table X. For example, compound 37.007 has the following structure:

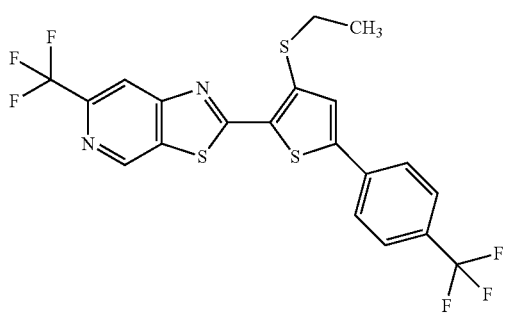

(37.007)

Table 38:

This table discloses the 42 compounds 38.001 to 38.042 of the formula (Iaf) wherein n is 2, $R_1$ is $CF_3$, $R_3$ is ethyl, and Zx is as defined in lines X.001-X.042 in table X.

The compounds of formula I according to the invention are preventively and/or curatively valuable active ingredients in the field of pest control, even at low rates of application, which have a very favourable biocidel spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*,

*Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp., *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea pleas*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp., *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp., *Trialeurodes* spp., *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp., *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp., *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absolute*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharine*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, *Cinnamomum* or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cystforming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniforrnis* and other *Rotylenchus* species; *Scutellonema* species; Stubby root nematodes, *Trichodorus primitivus* and other *Trichodorus* species; *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); *ochlodina; Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGarD® (maize variety that expresses a Cry1Ab toxin); YieldGard RootworM® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaF® (potato variety that expresses a Cry3A toxin); NatureGarD®, AgrisurE® GT Advantage (GA21 glyphosate-tolerant trait), AgrisurE® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide RounduP® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose,* or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/064072, WO2006/128870, EP 1724392, WO2005/113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
|  | *X. mutilatus* | Hardwoods |
|  | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
|  | *Agrilus politus* | Willow, Maple |
|  | *Agrilus sayi* | Bayberry, Sweetfern |
|  | *Agrilus vittaticolllis* | Apple, Pear, Cranberry, Serviceberry, Hawthorn |
|  | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
|  | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
|  | *Goes tigrinus* | Oak |
|  | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
|  | *Neoptychodes trilineatus* | Fig, Alder, Mulberry, Willow, Netleaf hackberry |
|  | *Oberea ocellata* | Sumac, Apple, Peach, Plum, Pear, Currant, Blackberry |
|  | *Oberea tripunctata* | Dogwood, Viburnum, Elm, Sourwood, Blueberry, Rhododendron, Azalea, Laurel, Poplar, Willow, Mulberry |
|  | *Oncideres cingulata* | Hickory, Pecan, Persimmon, Elm, Sourwood, Basswood, Honeylocust, Dogwood, Eucalyptus, Oak, Hackberry, Maple, Fruit trees |
|  | *Saperda calcarata* | Poplar |
|  | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
|  | *Dendroctonus frontalis* | Pine |
|  | *Dryocoetes betulae* | Birch, Sweetgum, Wild cherry, Beech, Pear |
|  | *Monarthrum fasciatum* | Oak, Maple, Birch, Chestnut, Sweetgum, Blackgum, Poplar, Hickory, *Mimosa*, Apple, Peach, Pine |

TABLE B-continued

Examples of native woodborers of economic importance.

| Family | Species | Host or Crop Infested |
|---|---|---|
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworms, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and green bugs. The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus lin-*

*earis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids. As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrates for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

PREPARATORY EXAMPLES

"Mpt." means melting point in ° C. Free radicals represent alkyl groups. $^1$H NMR and $^{19}$F NMR measurements were recorded on a Brucker 400 MHz spectrometer, chemical shifts are given in ppm relevant to a TMS standard. Spectra measured in deuterated solvents as indicated.

LCMS Methods:
Method 1:
Spectra were recorded on a Mass Spectrometer from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+ 0.05% HCOOH, B=Acetonitrile+0.05% HCOOH, gradient: 10-100% B in 1.2 min; Flow (mL/min) 0.85

Mass Spectroscopy Method ESI-MS
LC-20AD Mass Spectrometer from Shimadzu (Single quadrupole mass spectrometer)
Instrument Parameters:
Ionisation method: Electrospray
Polarity: positive and negative ions
Capillary (kV) 1.50
Cone (V) unknown
Extractor (V) 5.00
Source Temperature (° C.) 200
Desolvation Temperature (° C.) 250
Cone gas Flow (l/Hr) 90
Desolvation gas Flow (l/Hr) 90
Mass range: 50 to 1000 Da

Example H-1: Preparation of 2-[3-ethylsulfonyl-5-[4-(trifluoromethyl)phenyl]-2-thienyl]-3-methyl-6-(trifluoromethyl)imidazo[4,5-c]pyridine (Compound 2.007, Example P-1, Table P)

(Compound 2.007, example P-1, table P)

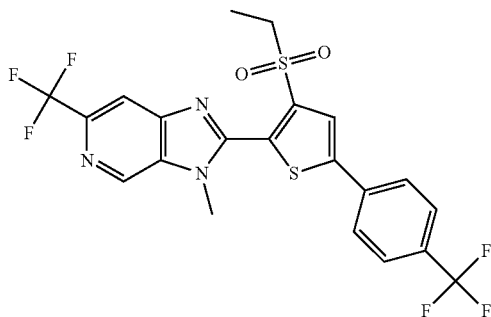

Step A: Preparation of 3-ethylsulfanylthiophene-2-carboxylic acid

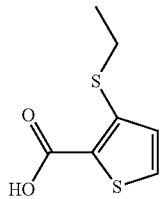

A solution of 3-bromothiophene-2-carboxylic acid (10.35 g, 50 mmol) and EtSNa (12.6 g, 150 mmol) in 60 mL of DMF was refluxed for 4 hours. Then, the mixture was poured into dilute hydrochloric acid and extracted with ethyl acetate three times. The combined organic layers were dried over sodium sulfate, filtered and concentrated in vacuo. The residue was purified by flash column chromatography on silica gel to give the title compound.

$^1$H NMR (400 Mz, DMSO-d$_6$): δ 1.28 (t, 3H), 3.04 (q, 2H), 7.16 (d, 1H), 7.86 (d, 1H), 12.91 (s, 1H).

ESI-MS(+): 189 (M+H)$^+$, 211 (M+Na)$^+$, 243 (M+Na+MeOH)$^+$.

Step B: Preparation of methyl 3-ethylsulfanylthiophene-2-carboxylate

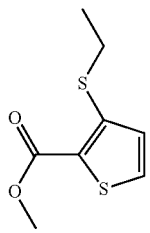

Diazomethane (30 mL, 15 mmol, 0.5 mol/L in diethyl ether) was added to a solution of compound 3-ethylsulfanylthiophene-2-carboxylic acid (1.88 g, 10 mmol) in diethyl ether (50 mL) at ambient temperature. The mixture was stirred at ambient temperature for 2 hours and poured into dilute hydrochloric acid, and extracted three times with ethyl acetate. The combined organic layers were dried over sodium sulfate, filtered and concentrated in vacuo. The residue was purified by flash column chromatography on silica gel to give the title product.

$^1$H NMR (400 Mz, DMSO-d$_6$): δ 1.29 (t, 3H), 3.05 (q, 2H), 3.78 (s, 3H), 7.21 (d, 1H), 7.93 (d, 1H).

ESI-MS(+): 203 (M+H)$^+$, 225 (M+Na)$^+$, 257 (M+Na+MeOH)$^+$.

Step C: Preparation of methyl 3-ethylsulfanyl-5-iodo-thiophene-2-carboxylate

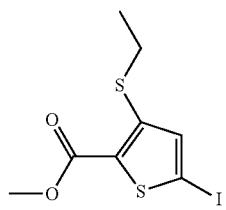

To a solution of diisopropylamine (3.03 g, 30 mmol) in 40 mL of dry tetrahydrofurane at −78° C. was added n-butyllithium (12 mL, 30 mmol, 2.5 M in hexane) under a nitrogen atmosphere. After stirring for 25 min. at −78° C., a solution of methyl 3-ethylsulfanylthiophene-2-carboxylate (5.05 g, 25 mmol) in 20 mL of dry tetrahydrofurane was added slowly during a 10 min period. The mixture was then allowed to stand at −78° C. for an additional 20 min and then treated with a solution of iodine (7 g, 27.5 mmol) in 20 mL of dry tetrahydrofurane. The cooling bath was removed and the solution was allowed to warm to ambient temperature over 1 h. The reaction mixture was then acidified with 1 M HCl and 100 mL of ether was added. The aqueous layer was extracted with ether (3×100 mL) and the combined organic layers were washed with water, dried over MgSO$_4$, and concentrated in vacuo. The residue was purified by flash column chromatography on silica gel to give the title product.

$^1$H NMR (400 Mz, DMSO-d$_6$): δ 1.26 (t, 3H), 3.06 (q, 2H), 3.76 (s, 3H), 7.44 (s, 1H).

Step D: Preparation of 3-ethylsulfanyl-5-iodo-thiophene-2-carboxylic acid

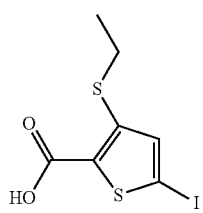

A mixture of methyl 3-ethylsulfanyl-5-iodo-thiophene-2-carboxylate (3.28 g, 10 mmol) and LiOH (480 mg, 20 mmol) in 30 mL of water and 30 mL of THF was stirred at ambient temperature for 16 h. The reaction mixture was then poured into diluted hydrochloric acid and extracted with ethyl acetate three times. The combined organic layers were dried over sodium sulfate, filtered and concentrated in vacuo. The residue was purified by flash column chromatography on silica gel to provide the title product.

$^1$H NMR (400 Mz, DMSO-d$_6$): δ 1.26 (t, 3H), 3.02 (q, 2H), 7.38 (s, 1H), 13.05 (s, 1H).

Step E: Preparation of 2-(3-ethylsulfanyl-5-iodo-2-thienyl)-3-methyl-6-(trifluoromethyl)imidazo[4,5-c]pyridine (Compound I-12, Table I)

Compound I-12, table I

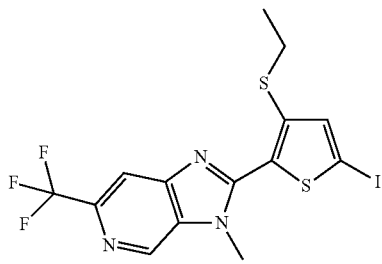

Oxalyl chloride (762 mg, 6 mmol) was added to a solution of 3-ethylsulfanyl-5-iodo-thiophene-2-carboxylic acid (628 mg, 2 mmol) in 10 mL of dichloromethane and stirred at ambient temperature for 16 hours. The excess oxalyl chloride and dichloromethane was removed under reduced pressure to give 3-ethylsulfanyl-5-iodo-thiophene-2-carbonyl chloride.

$^1$H NMR (400 MHz, DMSO-d6): δ 1.41 (t, 3H), 3.05 (q, 2H), 7.19 (s, 1H)).

This was dissolved in 20 mL of toluene and treated with N$^3$-methyl-6-(trifluoro methyl)pyridine-3,4-diamine (420 mg, 2.2 mmol, prepared as described in WO2015/000715) and the mixture refluxed for 48 h. The reaction mixture was then poured into water and extracted with ethyl acetate three times. The combined organic layers were dried over sodium sulfate, filtered and concentrated in vacuo. The residue was purified by flash column chromatography on silica gel to give the title compound as a white solid.

Mpt: 61-63° C.

$^1$H NMR (400 MHz, DMSO-d6): δ 1.18 (t, 3H), 3.01 (q, 2H), 3.97 (s, 3H), 7.54 (s, 1H), 8.22 (s, 1H), 9.20 (s, 1H).
ESI-MS(+): 470 (M+H)$^+$, 492 (M+Na)$^+$.

Step F: Preparation of 2-(3-ethylsulfonyl-5-iodo-2-thienyl)-3-methyl-6-(trifluoromethyl)imidazo[4,5-c]pyridine (Compound I-1, Table I)

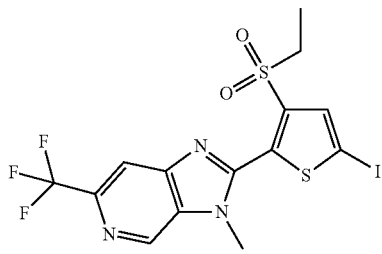 [SMILES: CCS(=O)(=O)c1cc(I)sc1-c1nc2cc(C(F)(F)F)ncc2n1C]

A solution of 2-(3-ethylsulfanyl-5-iodo-2-thienyl)-3-methyl-6-(trifluoromethyl)imidazo[4,5-c]pyridine (469 mg, 1 mmol) and m-CPBA (516 mg, 3 mmol) in 20 mL of dichloromethane was stirred at ambient temperature for 4 h. Then the mixture was poured into a saturated solution of NaHCO$_3$ and Na$_2$SO$_3$ in water, and extracted with ethyl acetate three times. The combined organic layers were dried over sodium sulfate, filtered and concentrated in vacuo. The residue was purified by flash column chromatography on silica gel to give the title product as a white solid.

Mpt. 255-257° C.

LCMS (method 1): retention time: 0.93 min; 502 (M+H).

$^1$H NMR (400 MHz, DMSO-d6): δ 1.28 (t, 3H), 3.43 (q, 2H), 3.86 (s, 3H), 7.92 (s, 1H), 8.28 (s, 1H), 9.25 (s, 1H).

$^{19}$F-NMR (400 Mz, DMSO-d$_6$): δ−63.92 (s, 3F).

ESI-MS(+): 502 (M+H)$^+$, 524 (M+Na)$^+$, 556 (M+Na+MeOH)$^+$.

Step G: Preparation of 2-[3-ethylsulfonyl-5-[4-(trifluoromethyl)phenyl]-2-thienyl]-3-methyl-6-(trifluoromethyl)imidazo[4,5-c]pyridine (Compound 2.007, Example P-1, Table P)

(Compound 2.007, example P-1, table P)

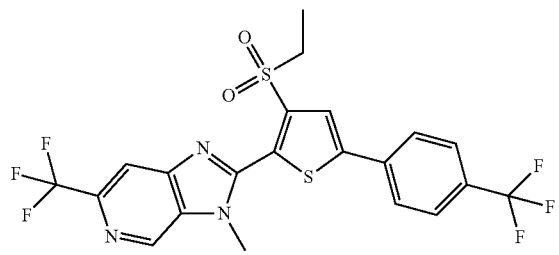

A suspension of 2-(3-Ethylsulfonyl-5-iodo-2-thienyl)-3-methyl-6-(trifluoromethyl)imidazo[4,5-c]pyridine (400 mg, 0.8 mmol), Pd(PPh$_3$)$_4$ (116 mg, 0.1 mmol), potassium carbonate (276 mg, 2 mmol) and 4-(trifluoromethyl)phenyl boronic acid (190 mg, 1 mmol) in 5 mL of DMF was refluxed for 16 h under nitrogen. After this time, the mixture was poured into water and extracted with ethyl acetate three times. The combined organic layers were dried over sodium sulfate, filtered and concentrated in vacuo. The residue was purified by flash column chromatography on silica gel to give the title product as white crystals.

Mpt. 181-183° C.

LCMS (method 1): retention time: 1.13 min; 520 (M+H).

$^1$H NMR (400 MHz, DMSO-d6): δ 1.18 (t, 3H), 3.51 (q, 2H), 3.93 (s, 3H), 7.89 (d, 2H), 8.09 (d, 2H), 8.28 (s, 1H), 8.30 (s, 1H), 9.28 (s, 1H).

$^{19}$F-NMR (400 Mz, DMSO-d$_6$): δ −59.75 (s, 3F), −56.47 (s, 3F).

ESI-MS(+): 520 (M+H)$^+$, 574 (M+Na+MeOH)$^+$.

Example H-2: Preparation of 2-[3-ethylsulfanyl-5-[3-(trifluoromethyl)pyrazol-1-yl]-2-thienyl]-3-methyl-6-(trifluoromethyl)imidazo[4,5-c]pyridine (Compound 1.017, Example P-3, Table P)

(Compound 1.017, example P-3, table P)

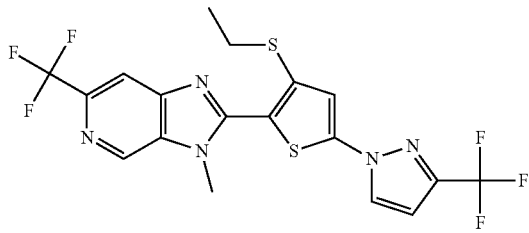

A solution of 2-(3-ethylsulfanyl-5-iodo-2-thienyl)-3-methyl-6-(trifluoromethyl)imidazo[4,5-c]pyridine (469 mg, 1 mmol, step E, example H-1) in 20 mL of 1,4-dioxane, was treated with 3-(trifluoromethyl)-1H-pyrazole (408 mg, 3 mmol), potassium carbonate (414 mg, 3 mmol), CuI (19 mg, 0.1 mmol) and N,N'-dimethylethylenediamine (9 mg, 0.1 mmol) and the mixture refluxed for 16 h under nitrogen. After this time, the mixture was poured into water and extracted with ethyl acetate three times. The combined organic layers were dried over sodium sulfate, filtered and concentrated in vacuo. The residue was purified by flash column chromatography on silica gel to give the title product as an off white solid.

Mpt. 162-164° C.
LCMS (method 1): retention time: 1.16 min; 478 (M+H).
$^1$H NMR (400 MHz, DMSO-d6): δ 1.20 (t, 3H), 3.03 (q, 2H), 4.01 (s, 3H), 7.15 (d, 1H), 7.87 (s, 1H), 8.21 (s, 1H), 8.86 (s, 1H), 9.18 (s, 1H).
$^{19}$F-NMR (400 Mz, DMSO-d$_6$): δ −61.42 (s, 3F), −57.78 (s, 3F).
ESI-MS(+): 478 (M+H)$^+$.

Example H-3: Preparation of 2-[3-ethylsulfonyl-5-[3-(trifluoromethyl)pyrazol-1-yl]-2-thienyl]-3-methyl-6-(trifluoromethyl)imidazo[4,5-c]pyridine (Compound 2.017, Example P-2, Table P)

(Compound 2.017, example P-2, table P)

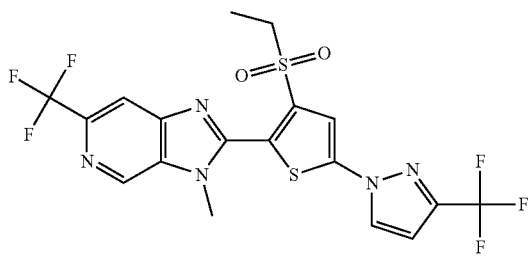

A solution of 2-[3-ethylsulfanyl-5-[3-(trifluoromethyl)pyrazol-1-yl]-2-thienyl]-3-methyl-6-(trifluoromethyl)imidazo[4,5-c]pyridine (100 mg, 0.21 mmol, from example H-2 above) in 10 mL of dichloromethane was treated with m-CPBA (109 mg, 0.63 mmol) and stirred at ambient temperature for 4 h. After this time, the mixture was poured into a saturated solution of NaHCO$_3$ and Na$_2$SO$_3$ in water, and extracted with ethyl acetate three times. The combined organic layers were dried over sodium sulfate, filtered and concentrated in vacuo. The residue was purified by flash column chromatography on silica gel to give the title products as a white solid.

Mpt. 173-175° C.
LCMS (method 1): retention time: 1.06 min; 510 (M+H).
$^1$H NMR (400 MHz, CDCl$_3$): δ 1.31 (t, 3H), 3.33 (q, 2H), 3.94 (s, 3H), 6.82 (d, 1H), 7.56 (s, 1H), 8.02 (s, 1H), 8.12 (s, 1H), 8.99 (s, 1H).
$^{19}$F-NMR (400 Mz, CDCl$_3$): δ −62.13 (s, 3F), −58.35 (s, 3F).
ESI-MS(+): 510 (M+H)$^+$, 532 (M+Na)$^+$, 564 (M+Na+MeOH)$^+$.

Example H-4: Preparation of 2-[5-(4-chlorophenyl)-3-ethylsulfanyl-2-thienyl]-3-methyl-6-(trifluoromethyl)imidazo[4,5-c]pyridine (Compound 1.004, Example P-6, Table P)

Compound 1.004, example P-6, table P

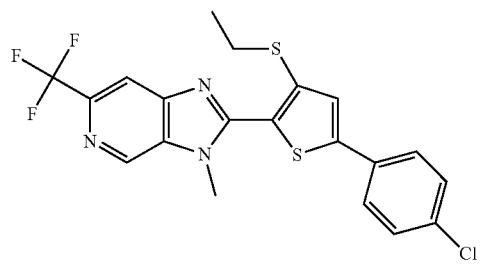

Step A: Preparation of methyl 5-(4-chlorophenyl)-3-ethylsulfanyl-thiophene-2-carboxylate

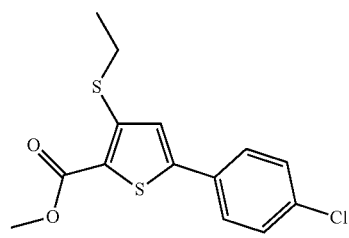 [SMILES: CCSc1cc(-c2ccc(Cl)cc2)sc1C(=O)OC]

A suspension of methyl 3-ethylsulfanyl-5-iodo-thiophene-2-carboxylate (3.28 g, 10 mmol, step C from example H-1), Pd(PPh$_3$)$_4$ (1.16 g, 1 mmol), cesium carbonate (6.52 g, 20 mmol) and 4-chlorophenylboronic acid (1.87 g, 12 mmol) in 50 mL of DME and 10 mL of H$_2$O was refluxed for 16 h, under nitrogen. After this time, the mixtures was cooled, poured into water and extracted with ethyl acetate three times. The combined organic layers were dried over sodium sulfate, filtered and concentrated in vacuo. The residue was purified by flash column chromatography on silica gel to give the title product as a yellow solid.

$^1$H NMR (400 MHz, DMSO-d6): δ 1.30 (s, 3H), 3.16 (q, 2H), 3.76 (s, 3H), 7.52 (d, 2H), 7.64 (s, 1H), 7.82 (d, 2H).
ESI-MS(+): 313 (M+H)$^+$, 335 (M+Na)$^+$, 367 (M+Na+MeOH)$^+$.

Step B: Preparation of 5-(4-Chlorophenyl)-3-ethyl-sulfanyl-thiophene-2-carboxylic acid

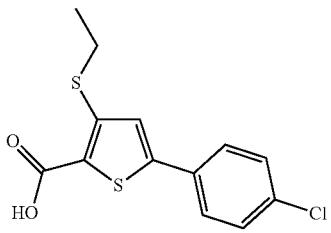 [SMILES: CCSc1cc(-c2ccc(Cl)cc2)sc1C(=O)O]

A mixture of methyl 5-(4-chlorophenyl)-3-ethylsulfanyl-thiophene-2-carboxylate (2.5 g, 8 mmol) and LiOH (576 mg, 24 mmol) in 30 mL of water and 30 mL of THF was stirred at ambient temperature for 16 h. The reaction mixture was then poured into diluted hydrochloric acid and extracted with ethyl acetate three times. The combined organic layers were dried over sodium sulfate, filtered and concentrated in vacuo. The residue was purified by flash column chromatography on silica gel to provide the title product as a white solid.

$^1$H NMR (400 MHz, DMSO-d6): δ 1.31 (s, 3H), 3.14 (q, 2H), 7.52 (d, 2H), 7.59 (s, 1H), 7.81 (d, 2H), 13.03 (s, 1H).

Step C: Preparation of 2-[5-(4-chlorophenyl)-3-ethylsulfanyl-2-thienyl]-3-methyl-6 (trifluoromethyl)imidazo[4,5-c]pyridine (Compound 1.004, Example P-6, Table P)

Compound 1.004, example P-6, table P

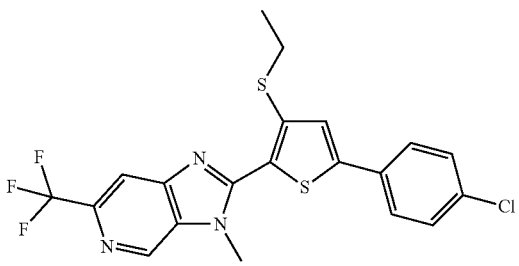

Oxalyl chloride (380 mg, 3 mmol) was added to a solution of 5-(4-Chlorophenyl)-3-ethylsulfanyl-thiophene-2-carboxylic acid (298 mg, 1 mmol) in 10 mL of dichloromethane. After the addition, the mixture was stirred at ambient temperature for 16 h. The excess oxalyl chloride and dichloromethane was removed in vacuo to give the crude product (5-(4-chlorophenyl)-3-ethylsulfanyl-thiophene-2-carbonyl chloride) in almost quantitative yield which was directly used for the next step without further purification.

$^1$H NMR (400 MHz, CDCl$_3$): δ 1.45 (s, 3H), 3.11 (q, 2H), 7.19 (s, 1H), 7.42 (d, 2H), 7.57 (d, 2H).

The sample of 5-(4-chlorophenyl)-3-ethylsulfanyl-thiophene-2-carbonyl chloride (316 mg, 1 mmol) from above, was dissolved in 20 mL of toluene and treated with N$^3$-methyl-6-(trifluoro methyl)pyridine-3,4-diamine (210 mg, 1.1 mmol, prepared as described in WO2015/000715). The mixture was heated at reflux for 48 h and then poured into water and extracted with ethyl acetate three times. The combined organic layers were dried over sodium sulfate, filtered and concentrated in vacuo. The residue was purified by flash column chromatography on silica gel to give the title product as a white solid.

Mpt. 146-148° C.
LCMS (method 1): retention time: 1.21 min; 454 (M+H).
$^1$H NMR (400 MHz, DMSO-d6): δ 1.22 (t, 3H), 3.11 (q, 2H), 4.02 (s, 3H), 7.55 (d, 2H), 7.83 (d, 2H), 7.86 (s, 1H), 8.22 (s, 1H), 9.20 (s, 1H).
$^{19}$F-NMR (400 Mz, DMSO-d$_6$): δ −59.74 (s, 3F).
ESI-MS(+): 454 (M+H)$^+$, 476 (M+Na)$^+$, 508 (M+Na+MeOH)$^+$.

Example H-5: Preparation of 2-[5-(4-chlorophenyl)-3-ethylsulfonyl-2-thienyl]-3-methyl-6-(trifluoromethyl)imidazo[4,5-c]pyridine (Compound 2.004, Example P-5, Table P)

Compound 2.004, example P-5, table P

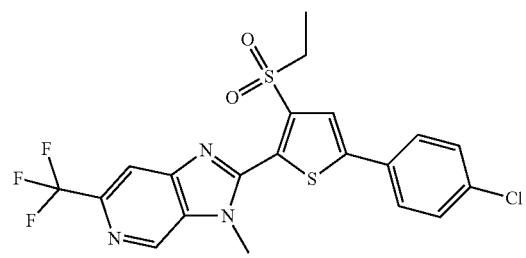

A solution of 2-[5-(4-chlorophenyl)-3-ethylsulfanyl-2-thienyl]-3-methyl-6-(trifluoromethyl)imidazo[4,5-c]pyridine (100 mg, 0.21 mmol) in 10 mL of dichloromethane was treated with m-CPBA (109 mg, 0.63 mmol) in 10 mL and stirred at ambient temperature for 2 h. The mixture was then poured into a saturated solution of NaHCO$_3$ and Na$_2$SO$_3$ in water, and extracted with ethyl acetate three times. The combined organic layers were dried over sodium sulfate, filtered and concentrated in vacuo. The residue was purified by column chromatography on silica gel to give the title product as a white solid.

Mpt. 170-172° C.
LCMS (method 1): retention time: 1.08 min; 486 (M+H).
$^1$H NMR (400 MHz, DMSO-d6) δ 1.18 (t, 3H), 3.50 (q, 2H), 3.92 (s, 3H), 7.59 (d, 2H), 7.88 (d, 2H), 8.14 (s, 1H), 8.29 (s, 1H), 9.27 (s, 1H).
$^{19}$F-NMR (400 Mz, DMSO-d$_6$): δ −59.77 (s, 3F).
ESI-MS(+): 486 (M+H)$^+$, 508 (M+Na)$^+$, 540 (M+Na+MeOH)$^+$.

Example H-6: Preparation of 2-[4-chloro-5-(4-chlorophenyl)-3-ethylsulfanyl-2-thienyl]-3-methyl-6-(trifluoromethyl)imidazo[4,5-c]pyridine (Compound 15.001, Example P-7, Table P)

Compound 15.001, example P-7, table P

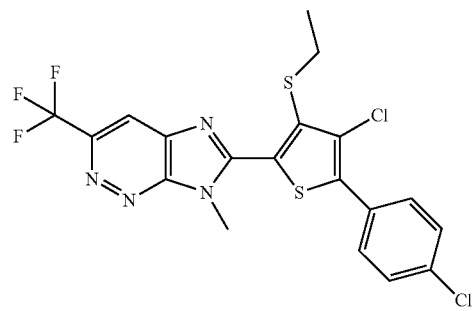

A solution of 5-(4-chlorophenyl)-3-ethylsulfanyl-thiophene-2-carboxylic acid (298 mg, 1 mmol, step B, example H-4) and thionyl chloride (10 mL) was refluxed for 4 h. After this time, the excess thionyl chloride was removed under reduced pressure to give 4-chloro-5-(4-chlorophenyl)-3-ethylsulfanyl-thiophene-2-carbonyl chloride which was used in the next step without purification. The acid chloride was dissolved in 20 mL of toluene and treated with $N^3$-methyl-6-(trifluoro methyl)pyridine-3,4-diamine (191 mg, 1 mmol, prepared as described in WO 2015/000715) and the mixture was refluxed for 48 h under nitrogen. The mixture was then poured into water and extracted with ethyl acetate three times. The combined organic layers were dried over sodium sulfate, filtered and concentrated in vacuo. The residue was purified by flash column chromatography on silica gel to give the title product as a white solid Mpt. 116-118° C.

LCMS (method 1): retention time: 1.29 min; 488 (M+H).

$^1$H NMR (400 MHz, DMSO-d6): δ 1.01 (t, 3H), 2.74 (q, 2H), 3.99 (s, 3H), 7.65 (d, 2H), 7.77 (d, 2H), 8.29 (s, 1H), 9.27 (s, 1H); $^{19}$F-NMR (400 Mz, DMSO-d$_6$): δ −59.77 (s, 3F); ESI-MS(+): 488 (M+H)$^+$.

Example H-7: Preparation of 2-[4-chloro-5-(4-chlorophenyl)-3-ethylsulfonyl-2-thienyl]-3-methyl-6-(trifluoromethyl)imidazo[4,5-c]pyridine (Compound 16.001, Example P-8, Table P)

Compound 16.001, example P-8, table P

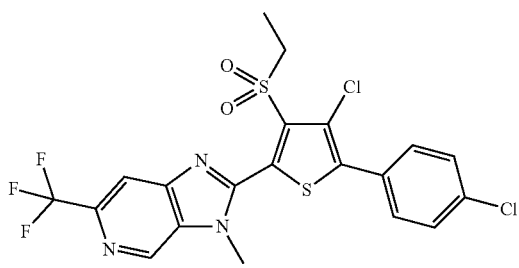

A sample of 2-[4-chloro-5-(4-chlorophenyl)-3-ethylsulfanyl-2-thienyl]-3-methyl-6-(trifluoromethyl)imidazo[4,5-c]pyridine (58 mg, 0.12 mmol) and m-CPBA (62 mg, 0.36 mmol) in 10 mL of dichloromethane was stirred at ambient temperature for 2 h. The mixture was then poured into a saturated solution of NaHCO$_3$ and Na$_2$SO$_3$ in water, and extracted with ethyl acetate three times. The combined organic layers were dried over sodium sulfate, filtered and concentrated in vacuo. The residue was purified by flash column chromatography on silica gel to give the title compound as a white solid.

Mpt. 212-214° C.

LCMS (method 1): retention time: 1.14 min; 520 (M+H).

$^1$H NMR (400 MHz, DMSO-d6): δ 1.20 (t, 3H), 3.51 (q, 2H), 3.91 (s, 3H), 7.67 (d, 2H), 7.77 (d, 2H), 8.29 (s, 1H), 9.27 (s, 1H).

$^{19}$F-NMR (400 Mz, DMSO-d$_6$): δ −59.76 (s, 3F).

ESI-MS(+): 520 (M+H)$^+$, 542 (M+Na)$^+$, 574 (M+Na+MeOH)$^+$.

Example H-8: Preparation of 2-(4-chlorophenyl)-4-ethylsulfanyl-5-[3-methyl-6-(trifluoromethyl)imidazo[4,5-c]pyridin-2-yl]thiazole (Compound 19.004, Example P-25, Table P)

Compound 19.004, example P-25, table P

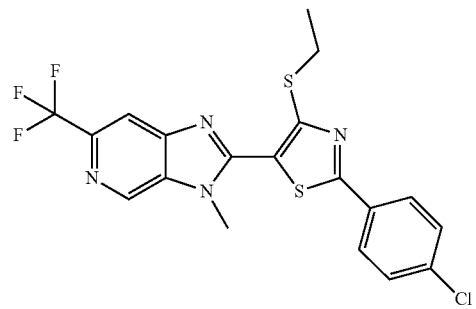

Step A: Preparation of 4-bromo-2-(4-chlorophenyl)thiazole

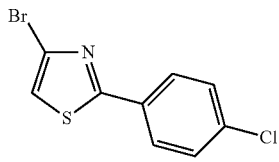 [SMILES: Clc1ccc(-c2nc(Br)cs2)cc1]

A mixture of 2,4-dibromothiazole (482 mg, 2 mmol; CAS: [4175-77-3]) Pd(PPh$_3$)$_4$ (116 mg, 0.1 mmol), cesium carbonate (978 mg, 3 mmol) and 4-chlorophenylboronic acid (312 mg, 2 mmol) dissolved in 20 ml of DME and 10 mL of H$_2$O was refluxed for 16 h under nitrogen. After this time, the mixture was diluted with water and extracted with ethyl acetate three times. The combined organic layers were dried over sodium sulfate, filtered and concentrated in vacuo. The residue was purified by flash column chromatography on silica gel to give the title compound.

$^1$H NMR (400 MHz, DMSO-d6): δ 7.59 (d, 2H), 7.94 (d, 2H), 7.95 (s, 1H).

EI-MS: 273/275 (M).

Step B: Preparation of 4-bromo-2-(4-chlorophenyl)thiazole-5-carboxylic acid

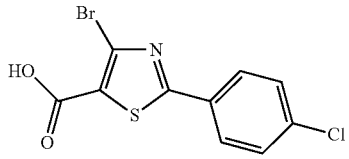 [SMILES: O=C(O)c1sc(-c2ccc(Cl)cc2)nc1Br]

A solution of i-Pr$_2$NH (253 mg, 2.5 mmol) in 5 mL of THF was treated dropwise with n-BuLi (1 mL, 2.5 mmol; 2.5M in hexane) at −60° C. under nitrogen. After the addition, 4-Bromo-2-(4-chlorophenyl)thiazole (546 mg, 2 mmol) dissolved in 2 mL of THF, was added slowly to the reaction mixture, and stirring continued for a further 20 min. The reaction mixture was then poured into dry ice and stirred until the dry ice dissolved. The reaction mixture was poured into dilute hydrochloric acid and extracted with ethyl acetate three times. The combined organic layers were dried over sodium sulfate, filtered and concentrated in vacuo. The residue was purified by flash column chromatography on silica gel to give the title product as a white solid.

$^1$H NMR (400 MHz, DMSO-d6): δ 7.61 (d, 2H), 8.01 (d, 2H).

Step C: Preparation of 2-(4-chlorophenyl)-4-ethylsulfanyl-5-[3-methyl-6-(trifluoromethyl)imidazo[4,5-c]pyridin-2-yl]thiazole

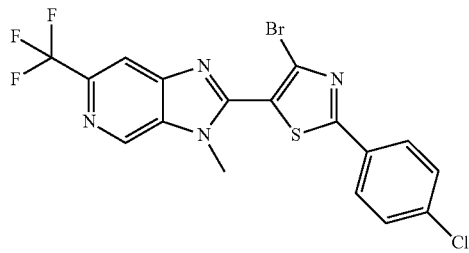 [SMILES: Cn1c(-c2sc(-c3ccc(Cl)cc3)nc2Br)nc2cc(C(F)(F)F)ncc21]

Oxalyl chloride (762 mg, 6 mmol) was added to a mixture of 4-bromo-2-(4-chlorophenyl)thiazole-5-carboxylic acid (632 mg, 2 mmol) in 10 mL of dichloromethane and stirring was continued at ambient temperature for 16 h. The excess oxalyl chloride and dichloromethane was removed in vacuo to give crude 4-bromo-2-(4-chlorophenyl)thiazole-5-carbonyl chloride.

$^1$H NMR (400 MHz, CDCl$_3$): δ 7.49 (d, 2H), 7.94 (d, 2H).

This acid chloride (672 mg, 2 mmol) was dissolved in 20 mL of toluene and treated with N$^3$-methyl-6-(trifluoromethyl)pyridine-3,4-diamine (420 mg, 2.2 mmol, prepared as described in WO2015/000715) and the mixture was refluxed for 48 h. After this time, the mixture was poured into water and extracted with ethyl acetate three times. The combined organic layers were dried over sodium sulfate, filtered and concentrated in vacuo. The residue was purified by flash column chromatography on silica gel to give the title compound.

$^1$H NMR (400 MHz, DMSO-d$_6$): δ 4.04 (s, 3H), 7.65 (d, 2H), 8.08 (d, 2H), 8.31 (s, 1H), 9.29 (s, 1H);

$^{19}$F NMR (400 MHz, DMSO-d$_6$): δ −59.77 (s, 3F).

Step D: Preparation of 2-(4-chlorophenyl)-4-ethylsulfanyl-5-[3-methyl-6-(trifluoromethyl)imidazo[4,5-c]pyridin-2-yl]thiazole (Compound 19.004, Example P-25, Table P)

Compound 19.004, example P-25, table P

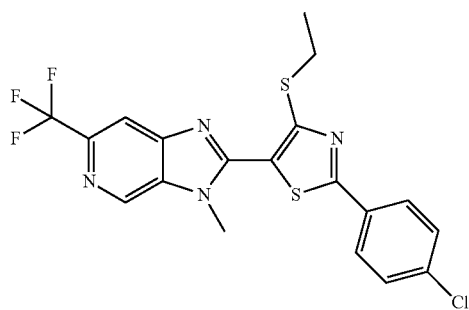

A sample of 2-(4-chlorophenyl)-4-ethylsulfanyl-5-[3-methyl-6-(trifluoromethyl)imidazo[4,5-c]pyridin-2-yl]thiazole (472 mg, 1 mmol) and EtSNa (100 mg, 1.2 mmol) in 5 mL of NMP, was stirred at ambient temperature for 1 h. The reaction mixture was then poured into dilute hydrochloric acid and extracted with ethyl acetate three times. The combined organic layers were dried over sodium sulfate, filtered and concentrated in vacuo. The residue was purified by flash column chromatography on silica gel to give the title product as a white powder.

$^1$H NMR (400 Mz, DMSO-d$_6$): δ 1.30 (t, 3H), 3.31 (q, 2H), 4.09 (s, 3H), 7.65 (d, 2H), 8.08 (d, 2H), 8.24 (s, 1H), 9.22 (s, 1H).

$^{19}$F NMR (400 MHz, DMSO-d$_6$): δ −59.78 (s, 3F).

ESI-MS(+): 455 (M+H)$^+$.

Example H-9: Preparation of 2-(4-chlorophenyl)-4-ethylsulfonyl-5-[3-methyl-6-(trifluoromethyl)imidazo[4,5-c]pyridin-2-yl]thiazole (Compound 20.004, Example P-4, Table P)

Compound 20.004, example P-4, table P

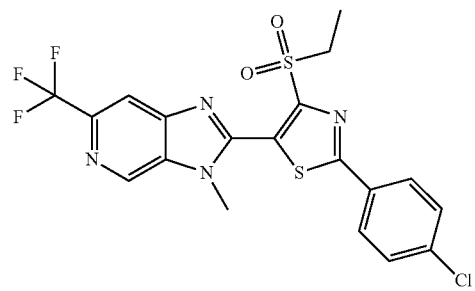

A sample of 2-(4-chlorophenyl)-4-ethylsulfanyl-5-[3-methyl-6-(trifluoromethyl)imidazo[4,5-c]pyridin-2-yl]thiazole (100 mg, 0.22 mmol) and m-CPBA (114 mg, 0.66 mmol) in 10 mL of dichloromethane was stirred at ambient temperature for 2 hours. The mixture was then poured into a saturated solution of NaHCO$_3$ and Na$_2$SO$_3$ in water, and extracted with ethyl acetate three times. The combined organic layers were dried over sodium sulfate, filtered and concentrated in vacuo. The residue was purified by column chromatography on silica gel to give the title compound as a white solid.

Mpt. 230-232° C.

LCMS (method 1): retention time: 1.03 min; 487 (M+H).

$^1$H NMR (400 Mz, DMSO-d$_6$): δ 1.20 (t, 3H), 3.58 (q, 2H), 3.95 (s, 3H), 7.68 (d, 2H), 8.12 (d, 2H), 8.29 (s, 1H), 9.28 (s, 1H).

$^{19}$F-NMR (400 Mz, DMSO-d$_6$): δ −63.95 (s, 3F).

ESI-MS(+): 487 (M+H)$^+$.

Example H-10: Preparation of 2-(3-ethylsulfonyl-5-pyrimidin-2-yl-2-thienyl)-3-methyl-6-(trifluoromethylsulfanyl)imidazo[4,5-c]pyridine (Compound 8.016, Example P-16 Table P)

(compound 8.016, example P-16, table P)

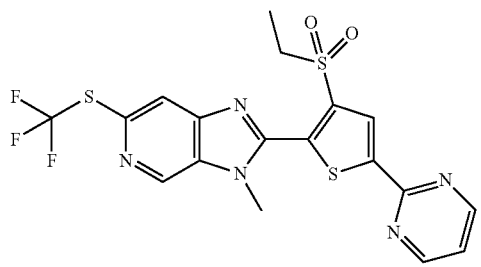

Step A: N-methyl-4-nitro-6-(trifluoromethylsulfanyl)pyridin-3-amine

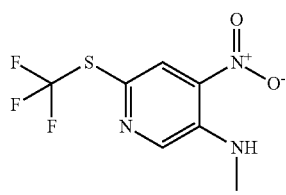 [SMILES: CNc1cnc(SC(F)(F)F)cc1[N+](=O)[O-]]

A sample of (bpy)CuSCF$_3$ (14.4 g, 45 mmol) and 6-bromo-N-methyl-4-nitro-pyridin-3-amine (6.96 g, 30 mmol, CAS [1218997-21-7]) in 120 mL of CH$_3$CN was refluxed for 48 h under nitrogen. The reaction mixture was removed from the oil bath and allowed to cool and then filtered through SiO$_2$, eluted with diethyl ether, washed with brine, and concentrated in vacuum. The residue was purified by silica gel column chromatography to give the title compound.

$^1$HNMR (400 MHz, DMSO-d$_6$): δ (ppm) 3.10 (d, J=5.2 Hz, 3H), 8.21 (s, 1H) 8.49 (q, 1H), 8.67 (s, 1H);
$^{19}$FNMR (376 MHz, DMSO-d$_6$): δ (ppm) −36.79 (s, 3F).
ESI-MS: 252 (M−H)$^−$.

Step B: Preparation of N3-methyl-6-(trifluoromethylsulfanyl)pyridine-3,4-diamine

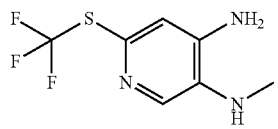

To a solution of N-methyl-4-nitro-6-(trifluoromethylsulfanyl)pyridin-3-amine (3.42 g, 13.5 mmol) in methanol (50 mL) was added Raney Ni (20% wt), and then the hydrazine hydrate (10 mL) was added dropwise at room temperature. The reaction mixture was stirred at room temperature for 30 minutes. Raney Ni was filtered off through celite; the filtrate was dried in vacuo and purified with chromatography column on silica gel (petroleum ethyl acetate=2:1) to afford the title compound as white solid.

$^1$HNMR (400 MHz, DMSO-d$_6$): δ ppm 2.78 (d, J=5.2 Hz, 3H), 5.20 (q, 1H), 5.77 (s, 2H), 6.82 (s, 1H), 7.53 (s, 1H).
$^{19}$FNMR (376 MHz, DMSO-d$_6$): δ ppm −45.49 (s, 3F).
ESI-MS(+): 224 (M+H)$^+$.

Step C: Preparation of 3-ethylsulfanyl-5-iodo-N-[5-(methylamino)-2-(trifluoromethylsulfanyl)-4-pyridyl]thiophene-2-carboxamide

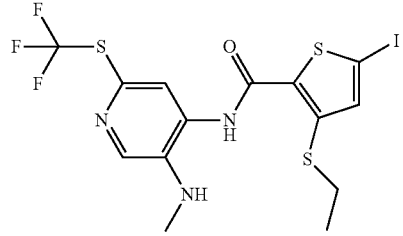 [SMILES: CCSc1cc(I)sc1C(=O)Nc1cc(SC(F)(F)F)ncc1NC]

To a solution of N3-methyl-6-(trifluoromethylsulfanyl)pyridine-3,4-diamine (1.45 g, 6.50 mmol) in THF (7.25 mL) was added triethylamine (2.29 mL, 16.2 mmol). The red solution was cooled down at 0° C. and treated dropwise with 3-ethylsulfanyl-5-iodo-thiophene-2-carbonyl chloride (2.16 g, 6.50 mmol, prepared as described in example H-1 step E) in dichloromethane (10.2 mL) at 0-5° C. over 10 min. The resulting suspension was stirred at 0° C. and then allowed to warm to room temperature and stirred for 4 hours. LC-MS analysis showed the desired mass. The reaction mixture was treated with NH$_4$Cl sat solution and the mixture was partially concentrated in vacuo to remove the toluene. The partially concentrated solution was extracted with ethyl acetate, and the combined organic layers washed with water and brine. The organic phase was dried over Na$_2$SO$_4$, filtered and concentrated in vacuo to give the title compound as a white solid.

LC/MS: (Method 1): Rt=1.05 Min; [M+H$^+$]520.

Step E: Preparation of 2-(3-ethylsulfanyl-5-iodo-2-thienyl)-3-methyl-6-(trifluoromethylsulfanyl)imidazo[4,5-c]pyridine (Example I-7 Table I)

(compound I-7 table I)

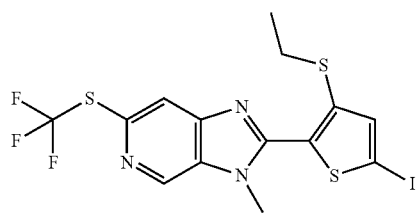

A yellow solution of 3-ethylsulfanyl-5-iodo-N-[5-(methylamino)-2-(trifluoromethylsulfanyl)-4-pyridyl]thiophene-2-carboxamide (3.43 g, 6.60 mmol) in acetic acid (17.2 mL) was stirred at 110° C. bath temperature for 2.5 hours. LC-MS analysis showed the desired mass. The reaction mixture was cooled down at room temperature and evaporated in using toluene to remove the excess of acetic. The crude was purified by flash chromatography over silica gel 2 times. Then the solid obtained was triturated with hexane, filtered and dried to give the title compound.

LC/MS: (Method 1) Rt=1.20 Min; [M+H⁺]502

$^1$H NMR (400 MHz, CHLOROFORM-d) δ ppm 1.22-1.28 (m, 3H) 2.87 (q, J=7.46 Hz, 2H) 3.95 (s, 3H) 7.31 (s, 1H) 8.13 (s, 1H) 8.88 (d, J=0.73 Hz, 1H).

Step F: Preparation of 2-(3-ethylsulfonyl-5-iodo-2-thienyl)-3-methyl-6-(trifluoromethylsulfanyl)imidazo[4,5-c]pyridine (Example I-8 Table I))

(compound I-8 table 1)

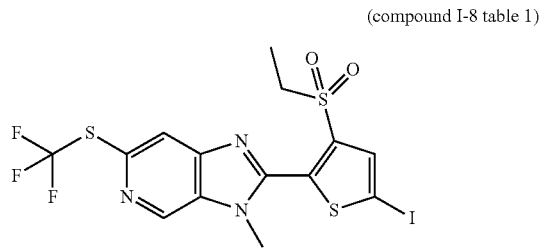 [SMILES: CCS(=O)(=O)c1cc(I)sc1-c1nc2cc(SC(F)(F)F)ncc2n1C]

At 0° C., m-CPBA (1.41 g, 6.30 mmol) was added to a solution of 2-(3-ethylsulfanyl-5-iodo-2-thienyl)-3-methyl-6-(trifluoromethylsulfanyl)imidazo[4,5-c]pyridine (1.54 g, 3.07 mmol) in chloroform (46.2 mL). After the addition the ice-bath was kept for 20 min and then the milky solution was allowed to warm up to room temperature and stirred overnight. LC-MS analysis showed mainly sulfoxide and a bit desired mass. The yellow solution was cooled down with an ice-bath and a second portion of m-CPBA (1.41 g, 6.30 mmol) was added and the resulting mixture was stirred 2 hours at room temperature. Sodium thiosulfate aqueous solution and sat NaHCO₃ aq were added and the mixture was stirred for 20 min. Dichloromethane was added and the organic layer was separated, washed again 2 times with NaHCO₃ and once with water, dried over Na₂SO₄ and evaporated. The crude was purified by flash chromatography over silica gel to give the title compound.

Mpt: 219-220° C.

LC/MS: (Method 1) Rt=1.03 Min; [M+H⁺] 534;

$^1$H NMR (400 MHz, CHLOROFORM-d) δ ppm 1.29 (t, J=7.34 Hz, 3H) 3.20-3.28 (m, 2H) 3.87 (s, 3H) 7.72 (s, 1H) 8.11 (s, 1H) 8.91 (d, J=0.73 Hz, 1H)

Step G: Preparation of 2-(3-ethylsulfonyl-5-pyrimidin-2-yl-2-thienyl)-3-methyl-6-(trifluoromethylsulfanyl)imidazo[4,5-c]pyridine (Compound 8.016, Example P-16 Table P)

(compound 8.016, example P-16 table P)

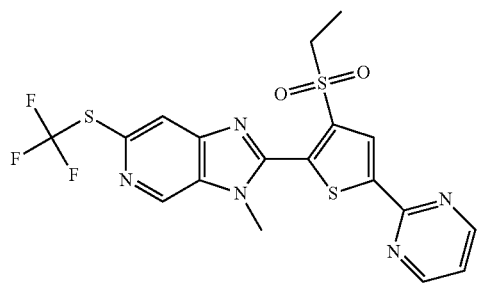

A yellow solution of 2-(3-ethylsulfonyl-5-iodo-2-thienyl)-3-methyl-6-(trifluoromethylsulfanyl)imidazo[4,5-c]pyridine (0.15 g, 0.28 mmol), tributyl(pyrimidin-2-yl)stannane (0.14 mL, 0.42 mmol) and Pd(PPH₃)₄ (0.016 g, 0.014 mmol) in toluene (3.8 mL) was heated at reflux and under argon atmosphere for 21 hours. LC-MS showed consumption of starting material. The crude was purified by flash chromatography over silica gel and then by reverse phase to give the title compound.

Mpt: 261-262° C.

LC/MS: (method 1); Rt=1.01, [M+H⁺] 486;

$^1$H NMR (400 MHz, CHLOROFORM-d) δ ppm 1.26 (t, J=7.34 Hz, 3H) 3.24 (q, J=7.46 Hz, 2H) 3.83 (s, 3H) 7.22 (t, J=4.95 Hz, 1H) 8.06 (s, 1H) 8.34 (s, 1H) 8.72 (d, J=4.77 Hz, 2H) 8.85 (d, J=0.73 Hz, 1H)

Example H-11: Preparation of 6-[5-(4-chlorophenyl)-3-ethylsulfanyl-2-thienyl]-7-methyl-3-(trifluoromethyl)imidazo[4,5-c]pyridazine (Compound 25.004, Example P-17 Table P)

(compound 25.004, example P-17 table P)

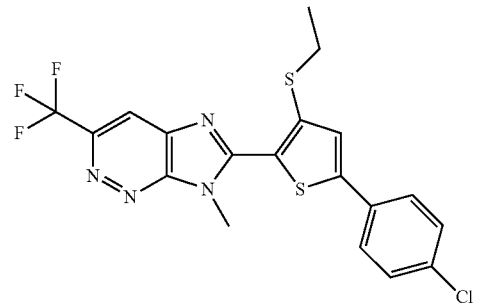

Step A: Preparation of 3-chloro-6-iodopyridazine

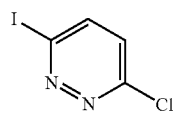

Hydroiodic acid (250 mL) was added to a mixture of 3,6-dichloropyridazine (149 g, 1 mol CAS:[135034-10-5]) and NaI (180 g, 1.2 mol) in 500 mL of CHCl₃. After the addition, the mixture was stirred at ambient temperature for 24 h, and poured into water and extracted with dichloromethane three times. The combined organic layers were dried over sodium sulfate, filtered and concentrated in vacuo to give 3-chloro-6-iodopyridazine.

$^1$H-NMR (400 Mz, DMSO-d₆) δ: 7.63 (d, 1H), 8.16 (d, 1H).

Step B: Preparation of 3-chloro-6-(trifluoromethyl)pyridazine

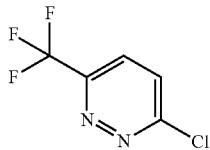

A sample of TMSCF$_3$ (198.8 g, 1.4 mol) was added to a mixture of 3-chloro-6-iodopyridazine (240 g, 1 mol), KF (81 g, 1.4 mol) and CuI (228 g, 1.2 mol) in 1 L of DMF under nitrogen. After the addition, the mixture was stirred at 50° C. for 2 h. The mixture was then poured into water and extracted with ether. The combined organic layers were dried over sodium sulfate, filtered and concentrated in vacuo. The residue was purified by flash column chromatography on silica gel to give 3-chloro-6-(trifluoromethyl)pyridazine.

$^1$H-NMR (400 Mz, DMSO-d$_6$) δ: 8.30 (d, 1H), 8.38 (d, 1H).
$^{19}$F-NMR (400 Mz, DMSO-d$_6$) δ: −64.93 (s, 3F).

Step C: Preparation of N-methyl-6-(trifluoromethyl)pyridazin-3-amine

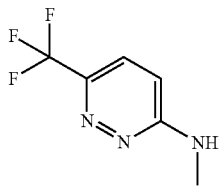

A solution of MeNH$_2$ (100 g, 30% in EtOH) was added to a mixture of 3-chloro-6-(trifluoromethyl)pyridazine (91 g, 0.5 mol) in 100 ml of EtOH. After the addition, the mixture was stirred at 50° C. for 2 hours and then poured into water. The precipitated solid was filtered and dried in vacuo to give N-methyl-6-(trifluoromethyl)pyridazin-3-amine.

$^1$H-NMR (400 Mz, DMSO-d$_6$) δ: 2.93 (d, 3H), 6.95 (d, 1H), 7.58 (q, 1H), 7.63 (d, 1H).
$^{19}$F-NMR (400 Mz, DMSO-d$_6$) δ: −59.88 (s, 3F).
ESI-MS(+): 178 (M+H)$^+$.

Step D: Preparation of 4-bromo-N-methyl-6-(trifluoromethyl)pyridazin-3-amine

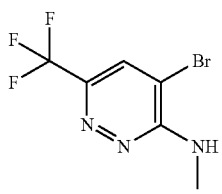

Bromine (32 g, 0.2 mol) was added to a mixture of N-methyl-6-(trifluoromethyl)pyridazin-3-amine (17.7 g, 0.1 mol) in 100 mL of MeCN. After the addition, the mixture was stirred at ambient temperature for 48 hours. After this time, the mixture was poured into ammonium hydroxide (10% solution) and extracted with ethyl acetate. The combined organic layers were dried over sodium sulfate, filtered and concentrated in vacuo. The residue was purified by flash column chromatography on silica gel to give the product 4-bromo-N-methyl-6-(trifluoromethyl)pyridazin-3-amine.

$^1$H-NMR (400 Mz, DMSO-d$_6$) δ: 3.03 (d, 3H), 7.45 (q, 1H), 8.23 (s, 1H).
$^{19}$F-NMR (400 Mz, DMSO-d$_6$) δ: −59.47 (s, 3F).
ESI-MS(+): 256/258 (M+H)

Step E: Preparation of N$^3$-methyl-6-(trifluoromethyl)pyridazine-3,4-diamine

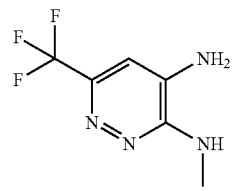

4-Bromo-N-methyl-6-(trifluoromethyl)pyridazin-3-amine (3 g, 11.8 mmol) and 120 mL of ammonium hydroxide was placed in a 250 mL autoclave. Then, nitrogen gas was introduced to the autoclave and pressure was increased to 2 MPa. The mixture was stirred at 130° C. for 48 h, poured into water and extracted with ethyl acetate. The combined organic layers were dried over sodium sulfate, filtered and concentrated under reduced pressure. The residue was purified by column chromatography on silica gel to give N$^3$-methyl-6-(trifluoromethyl)pyridazine-3,4-diamine.

$^1$H-NMR (400 Mz, DMSO-d$_6$) δ: 2.97 (d, 3H), 6.27 (s, 2H), 6.50 (q, 1H), 6.67 (s, 1H).
$^{19}$F-NMR (400 Mz, DMSO-d$_6$) δ: −61.96 (s, 3F).
ESI-MS(+): 193 (M+H)$^+$.

Step F: Preparation of 6-[5-(4-chlorophenyl)-3-ethylsulfanyl-2-thienyl]-7-methyl-3-(trifluoromethyl)imidazo[4,5-c]pyridazine (Compound 25.004, Example P-17 Table P)

(compound 25.004, example P-17 table P)

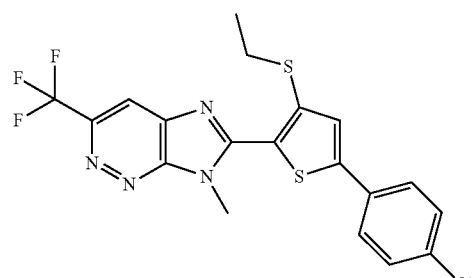

A solution of 5-(4-chlorophenyl)-3-ethylsulfanyl-thiophene-2-carbonyl chloride (0.37 g, 1.0eq, 1.2 mmol, prepared as described in example H-4, step C) in toluene (15 MI) was treated with N3-methyl-6-(trifluoromethyl)pyridazine-3,4-diamine (0.27 g, 1.2eq, 1.4 mmol) and the mixture was heated at reflux for 26 hr. LCMS after this time showed reaction completion. The mixture was cooled and poured into water and extracted with ethyl acetate three times. The combined organic layers were washed successively with water and brine, dried over anhydrous sodium sulfate, filtered and concentrated in vacuo. The crude product was dissolved in dichloromethane and adsorbed onto TEFLON BULK SORBENTS. Purification over silica gel cartridge (Rf200) eluting with cyclohexane/ethyl acetate. The product obtained was further purified by reversed phase HPLC to give the title compound as a white solid.

Mpt. 205-207° C.

LC/MS: (method 1) [M+H⁺] 455/457; Rt=1.27

Example H-12: Preparation of 6-[5-(4-chlorophenyl)-3-ethylsulfonyl-2-thienyl]-7-methyl-3-(trifluoromethyl)imidazo[4,5-c]pyridazine (Compound 26.004, Example P-18 Table P)

(compound 26.004, example P-18 table P)

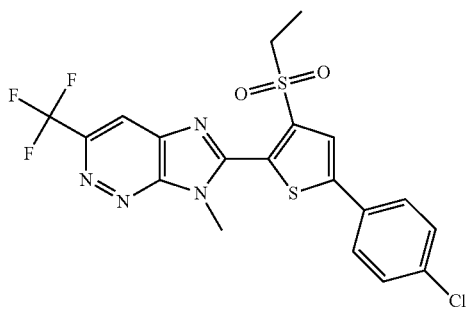

At 0° C., m-CPBA (0.06208 g, 0.2770 mmol) was added to a solution of 6-[5-(4-chlorophenyl)-3-ethylsulfanyl-2-thienyl]-7-methyl-3-(trifluoromethyl)imidazo[4,5-c] pyridazine (0.06 g, 1.000eq, 0.1319 mmol) in chloroform (2.84 g, 1.92 mL, 180eq, 23.8 mmol). After addition the ice-bath was kept for 10 min and then the milky solution was allowed to warm up to rt and stirred overnight. After this time, saturated sodium thiosulfate aqueous solution was added followed by sat NaHCO3aq and the mixture stirred at rt for 1 hr. The organic layer was separated, dried over sodium sulphate and concentrated in vacuo. The crude product was dissolved in dichloromethane and adsorbed onto TEFLON BULK SORBENTS. Purification over silica gel cartridge (Rf200) eluting with cyclohexane/ethyl acetate to give the title compound as a white solid.

Mpt. 166-168° C.

LC/MS: (method 1) [M+H⁺] 487/489; Rt=1.13.

¹H NMR (400 MHz, CHLOROFORM-d) δ ppm 1.36 (t, J=7.52 Hz, 3H) 3.38 (q, J=7.34 Hz, 2H) 4.13 (s, 3H) 7.49 (d, J=8.44 Hz, 2H) 7.61 (d, J=8.44 Hz, 2H) 7.75 (s, 1H) 8.20 (s, 1H).

Example H-13: Preparation of 4-ethylsulfonyl-5-[3-methyl-6-(trifluoromethyl)imidazo[4,5-c]pyridin-2-yl]-2-[3-(trifluoromethyl)pyrazol-1-yl]thiazole (Compound 20.017, Example P-10, Table P)

(Compound 20.017, example P-10 table P)

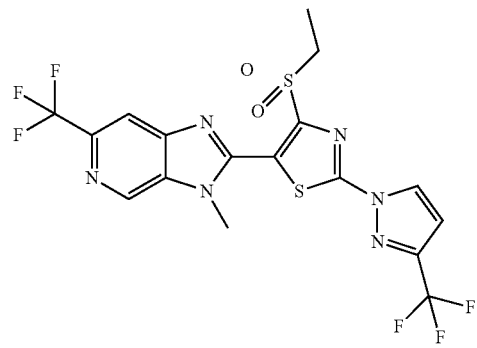

Step A: Preparation of 2-bromo-4-ethylsulfanyl-5-[3-methyl-6-(trifluoromethyl)imidazo[4,5-c]pyridin-2-yl]thiazole (Compound I-5, Table I)

(Compound I-5, table I)

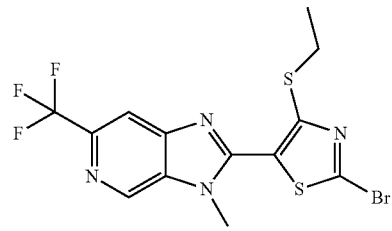

Oxalyl chloride (380 mg, 3 mmol) was added to a mixture of 2-bromo-4-ethylsulfanyl-thiazole-5-carboxylic acid (267 mg, 1 mmol) in 10 mL of dichloromethane and stirred at room temperature for 16 h. Then, the excess of oxalyl chloride and dichloromethane was removed under reduced pressure. The crude 2-bromo-4-ethylsulfanyl-thiazole-5-carbonyl chloride was directly used for the next step without further purification. The crude obtained 2-bromo-4-ethylsulfanyl-thiazole-5-carbonyl chloride was added to a mixture of N3-methyl-6-(trifluoro methyl)pyridine-3,4-diamine (191 mg, 1 mmol) in 20 mL of toluene and the mixture was reflux for 72 h. Then, the mixture was poured into water and extracted with ethyl acetate three times. The combined organic layers were dried over sodium sulfate, filtered and concentrated in vacuo. The crude product was purified by column chromatography on silica gel to give the title compound.

Mpt: 130-132° C.

LCMS (method 1): retention time: 1.11 min; 423/425 (M+H).

¹H NMR (400 MHz, DMSO-d6) δ 1.19 (t, 3H), 3.09 (q, 2H), 3.95 (s, 3H), 8.18 (s, 1H), 9.16 (s, 1H); ¹⁹F-NMR (400 Mz, DMSO-d₆) δ: −64.32 (s, 3F).

Step B: Preparation of 2-bromo-4-ethylsulfonyl-5-[3-methyl-6-(trifluoromethyl)imidazo[4,5-c]pyridin-2-yl]thiazole (Compound I-4, Table I)

(Compound I-4, table I)

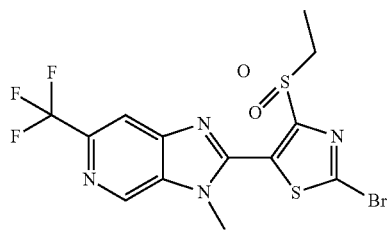

A sample of 2-bromo-4-ethylsulfanyl-5-[3-methyl-6-(trifluoromethyl)imidazo[4,5-c]pyridin-2-yl]thiazole (423 mg, 1 mmol) and m-CPBA (518 mg, 3 mmol) in 20 ml of dichloromethane was stirred at room temperature for 4 h. Then the mixture was poured into a saturated solution of NaHCO$_3$ and Na$_2$SO$_3$ in water, and extracted with ethyl acetate three times. The combined organic layers were dried over sodium sulfate, filtered and concentrated in vacuo. The crude product was purified by column chromatography on silica gel to give the title compound.

Mpt:248-250° C.

LCMS (method 1): retention time: 0.94 min; 457 (M+H).
$^1$H NMR (400 MHz, DMSO-d6) δ 1.16 (t, 3H), 3.47 (q, 2H), 3.88 (s, 3H), 8.26 (s, 1H), 9.25 (s, 1H); $^{19}$F-NMR (400 Mz, DMSO-d$_6$) δ: −62.17 (s, 3F)

Step C: Preparation of 4-ethylsulfonyl-5-[3-methyl-6-(trifluoromethyl)imidazo[4,5-c]pyridin-2-yl]-2-[3-(trifluoromethyl)pyrazol-1-yl]thiazole (Compound 20.017, Example P-10, Table P)

(Compound 20.017, example P-10 table P)

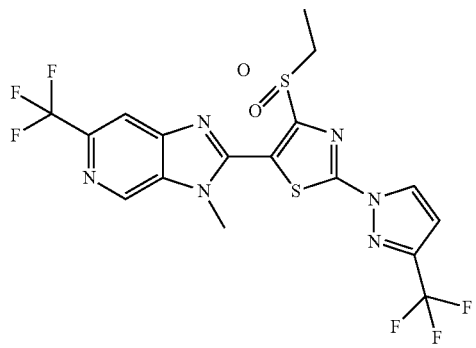

Under the protection of nitrogen, 2-bromo-4-ethylsulfonyl-5-[3-methyl-6-(trifluoromethyl)imidazo[4,5-c]pyridin-2-yl]thiazole (100 mg, 0.22 mmol) was added to a mixture of 3-(trifluoromethyl)-1H-pyrazole (90 mg, 0.66 mmol), salicylaldoxime (7 mg, 0.05 mmol), Cu$_2$O (7 mg, 0.05 mmol) and K$_2$CO$_3$ (69 mg, 0.5 mmol) in 10 ml of MeCN. After the addition, the mixture was refluxed for 16 h. Then, the mixture was poured into water and extracted with ethyl acetate three times. The combined organic layers were dried over sodium sulfate, filtered and concentrated in vacuo. The crude product was purified by column chromatography on silica gel to give the title compound.

Mpt: 185-187° C.

LCMS (method 1): retention time: 1.07 min; 511 (M+H).
$^1$H NMR (400 MHz, DMSO-d6) δ 1.19 (t, 3H), 3.52 (q, 2H), 3.91 (s, 3H), 7.27 (d, 1H), 8.28 (s, 1H), 8.95 (d, 1H), 9.26 (s, 1H); $^{19}$F NMR (400 MHz, DMSO-d6) δ: −62.39 (s, 3F), −59.34 (s, 3F);

Example H-14: Preparation of 4-ethylsulfonyl-5-[3-methyl-6-(trifluoromethyl)imidazo[4,5-c]pyridin-2-yl]-2-pyrimidin-2-yl-thiazole (Compound 20.016, Example P-9, Table P)

(Compound 20.016, example P-9, table P)

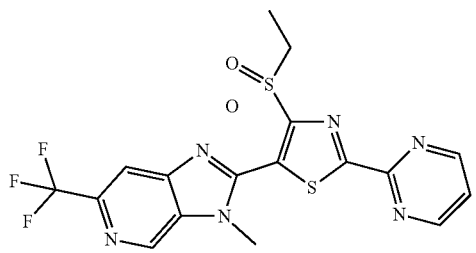

A sample 2-bromo-4-ethylsulfonyl-5-[3-methyl-6-(trifluoromethyl)imidazo[4,5-c]pyridin-2-yl]thiazole (227 mg, 0.5 mmol) was added to a mixture of tributyl(pyrimidin-2-yl)stannane (370 mg, 1 mmol), CuI (19 mg, 0.1 mmol), PdCl$_2$(PPh$_3$)$_2$ (70 mg, 0.1 mmol) in 20 ml of 1,4-dioxane. Then, the mixture was refluxed for 6 h and concentrated in vacuo. The crude product was purified by column chromatography on silica gel to give the title compound.

LCMS (method 1): retention time: 0.87 min; 455 (M+H).
$^1$H-NMR (400 Mz, CDCl$_3$) δ: 1.33 (t, 3H), 3.52 (q, 2H), 4.01 (s, 3H), 7.49 (t, 1H), 8.14 (s, 1H), 8.95 (d, 2H), 8.99 (s, 1H).
$^{19}$F NMR (400 MHz, CDCl$_3$) δ: −64.69 (s, 3F).
ESI-MS(−): 453 (M−H).

Example H-15: Preparation of 2-cyclopropyl-4-ethylsulfonyl-5-[3-methyl-6-(trifluoromethyl)imidazo[4,5-c]pyridin-2-yl]thiazole (Compound 20.021, Example P-13, Table P)

(Compound 20.021, example P-13, table P)

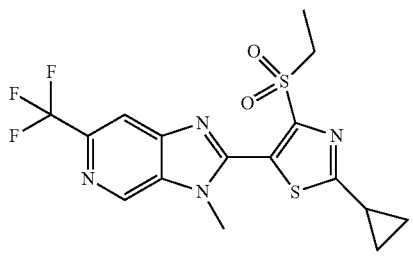

Step A: Preparation of methyl 4-bromo-2-cyclopropyl-thiazole-5-carboxylate

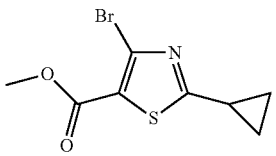

Under the protection of nitrogen, methyl 2,4-dibromothiazole-5-carboxylate (3 g, 10 mmol), Pd(PPh$_3$)$_4$ (1.16 g, 1 mmol), K$_2$CO$_3$ (2.76 g, 20 mmol) and cyclopropylboronic acid (1.03 g, 12 mmol) were dissolved in 50 ml of 1,4-dioxane. After the addition, the mixture was refluxed for 16 h. Then, the mixture was poured into water and extracted with ethyl acetate three times. The combined organic layers were dried over sodium sulfate, filtered and concentrated in vacuo. The crude product was purified by column chromatography on silica gel to give the title compound.

$^1$H NMR (400 MHz, DMSO-d6) δ 1.06-1.08 (m, 2H), 1.22-1.25 (m, 2H), 2.50-2.52 (m, 1H), 3.80 (s, 3H).

Step B: Preparation of 4-bromo-2-cyclopropyl-thiazole-5-carboxylic acid

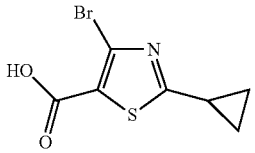 [SMILES: O=C(O)c1sc(C2CC2)nc1Br]

A mixture of methyl 4-bromo-2-cyclopropyl-thiazole-5-carboxylate (261 mg, 1 mmol) and LiOH (96 mg, 4 mmol) in 10 ml of water and 10 ml of THF was stirred at room temperature for 4 h. Then, the reaction mixture was poured into diluted hydrochloric acid and extracted with ethyl acetate three times. The combined organic layers were dried over sodium sulfate, filtered and concentrated in vacuo. The crude product was purified by column chromatography on silica gel to provide the title compound.

$^1$H NMR (400 MHz, DMSO-d6) δ 1.03-1.07 (m, 2H), 1.17-1.22 (m, 2H), 2.46-2.50 (m, 1H), 13.60 (br s, 1H).

Step C: Preparation of compound 4-bromo-2-cyclopropyl-5-[3-methyl-6-(trifluoromethyl)imidazo[4,5-c]pyridin-2-yl]thiazole

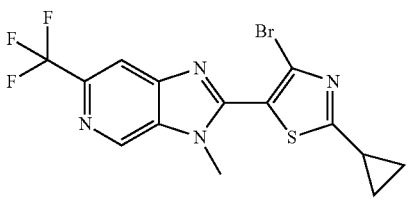 [SMILES: Cn1c(-c2sc(C3CC3)nc2Br)nc2cc(C(F)(F)F)ncc21]

DMF (5 mg) was added to a mixture of oxalyl chloride (190 mg, 1.5 mmol) and 4-bromo-2-cyclopropyl-thiazole-5-carboxylic acid (123 mg, 0.5 mmol) in 10 mL of dichloromethane and stirred at room temperature for 2 h. Then, the excess oxalyl chloride and dichloromethane was removed under reduced pressure to give 4-bromo-2-cyclopropyl-thiazole-5-carbonyl chloride. The crude obtained was added to a mixture of N$^3$-methyl-6-(trifluoromethyl)pyridine-3,4-diamine (105 mg, 0.55 mmol) in 20 mL of PhMe and the mixture was reflux for 72 h. Then, the mixture was poured into water and extracted with ethyl acetate three times. The combined organic layers were dried over sodium sulfate, filtered and concentrated in vacuo. The crude product was purified by column chromatography on silica gel to give the title compound.

$^1$H NMR (400 MHz, DMSO-d6) δ 1.09-1.11 (m, 2H), 1.22-1.25 (m, 2H), 2.62-2.65 (m, 1H), 3.94 (s, 3H), 8.22 (s, 1H), 9.21 (s, 1H).

$^{19}$F NMR (400 MHz, DMSO-d$_6$) δ −62.79 (s, 3F).

Step D: Preparation of Compound 2-cyclopropyl-4-ethylsulfanyl-5-[3-methyl-6-(trifluoromethyl)imidazo[4,5-c]pyridin-2-yl]thiazole (Compound 19.021, Example P-14, Table P)

(Compound 19.021, example P-14, table P)

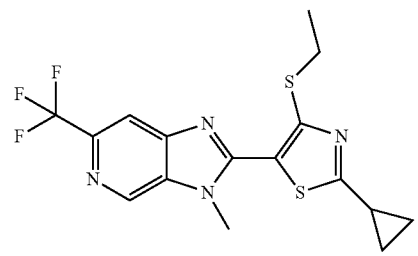

A sample of 4-bromo-2-cyclopropyl-5-[3-methyl-6-(trifluoromethyl)imidazo[4,5-c]pyridin-2-yl]thiazole (402 mg, 1 mmol) and EtSNa (100 mg, 1.2 mmol) in 5 ml of NMP was stirred at room temperature for 10 h. Then, the mixture was poured into dilute hydrochloric acid and extracted with ethyl acetate three times. The combined organic layers were dried over sodium sulfate, filtered and concentrated in vacuo. The crude product was purified by column chromatography on silica gel to give the title compound.

Mpt.97-99° C.

LCMS (method 1): retention time: 1.14 min; 385 (M+H).

$^1$H NMR (400 MHz, DMSO-d6) δ 1.08-1.10 (m, 2H), 1.20-1.24 (m, 5H), 2.53-2.55 (m, 1H), 3.09 (q, 2H), 3.97 (s, 3H), 8.15 (s, 1H), 9.14 (s, 1H);

$^{19}$F NMR (400 MHz, DMSO-d$_6$) δ−62.08 (s, 3F);

ESI-MS(+): 385 (M+H)$^+$.

Step E: Preparation of 2-cyclopropyl-4-ethylsulfonyl-5-[3-methyl-6-(trifluoromethyl)imidazo[4,5-c]pyridin-2-yl]thiazole (Compound 20.021, example P-13, table P)

(Compound 20.021, example P-13, table P)

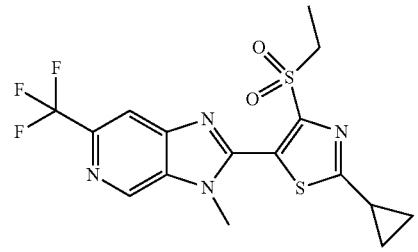

2-cyclopropyl-4-ethylsulfanyl-5-[3-methyl-6-(trifluoromethyl)imidazo[4,5-c]pyridin-2-yl]thiazole (192 mg, 0.5 mmol) and m-CPBA (285 mg, 1.5 mmol) in 10 ml of dichloromethane was stirred at room temperature for 6 h. Then the mixture was poured into a saturated solution of NaHCO₃ and Na₂SO₃ in water, and extracted with ethyl acetate three times. The combined organic layers were dried over sodium sulfate, filtered and concentrated in vacuo. The crude product was purified by column chromatography on silica gel to give the title compound.

Mpt. 166-168° C.

LCMS (method 1): retention time: 0.94 min; 417 (M+H).

$^1$H NMR (400 MHz, DMSO-d6) δ 1.09-1.15 (m, 5H), 1.27-1.29 (m, 2H), 2.62-2.55 (m, 1H), 3.40 (q, 2H), 3.84 (s, 3H), 8.22 (s, 1H), 9.21 (s, 1H);

$^{19}$F NMR (400 MHz, DMSO-d₆) δ −62.76 (s, 3F);

Example H-16: Preparation of 6-[3-ethylsulfonyl-5-[3-(trifluoromethyl)pyrazol-1-yl]-2-thienyl]-7-methyl-3-(trifluoromethyl)imidazo[4,5-c]pyridazine (Compound 26.017, example P-12, table P)

(Compound 26.017, example P-12, table P)

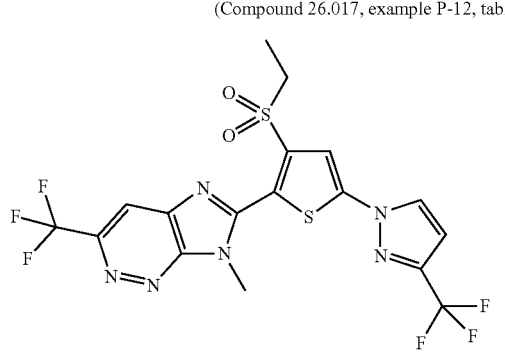

Step A: Preparation of 6-(3-ethylsulfanyl-5-iodo-2-thienyl)-7-methyl-3-(trifluoromethyl)imidazo[4,5-c]pyridazine

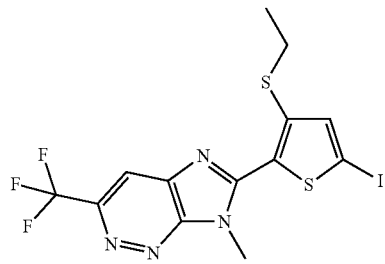 [SMILES: CCSc1cc(I)sc1-c1nc2cc(C(F)(F)F)nnc2n1C]

A sample of 3-ethylsulfanyl-5-iodo-thiophene-2-carbonyl chloride (332 mg, 1 mmol) was added to a mixture of N³-methyl-6-(trifluoromethyl)pyridazine-3,4-diamine (210 mg, 1.1 mmol) in 20 mL of THF and the mixture was reflux for 72 h. Then, the mixture was poured into water and extracted with ethyl acetate three times. The combined organic layers were dried over sodium sulfate, filtered and concentrated in vacuo. The crude product was purified by column chromatography on silica gel to give the title compound.

$^1$H NMR (400 MHz, DMSO-d6) δ 1.22 (t, 3H), 3.07 (q, 2H), 4.11 (s, 3H), 7.67 (s, 1H), 8.58 (s, 1H);

$^{19}$F NMR (400 MHz, DMSO-d6) δ −62.74 (s, 3F);

ESI-MS(+): 471 (M+H)⁺.

Step B: Preparation of 6-(3-ethylsulfonyl-5-iodo-2-thienyl)-7-methyl-3-(trifluoromethyl)imidazo[4,5-c]pyridazine (Compound 1-6, table I)

(Compound I-6, table I)

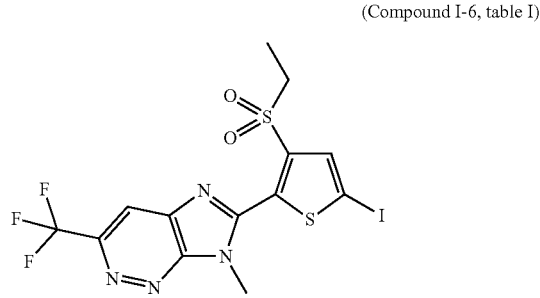 [SMILES: CCS(=O)(=O)c1cc(I)sc1-c1nc2cc(C(F)(F)F)nnc2n1C]

6-(3-ethylsulfanyl-5-iodo-2-thienyl)-7-methyl-3-(trifluoromethyl)imidazo[4,5-c]pyridazine (235 mg, 0.5 mmol) and m-CPBA (288 mg, 1.5 mmol) in 10 ml of dichloromethane was stirred at room temperature for 4 h. Then the mixture was poured into a saturated solution of NaHCO₃ and Na₂SO₃ in water, and extracted with ethyl acetate three times. The combined organic layers were dried over sodium sulfate, filtered and concentrated in vacuo. The crude product was purified by column chromatography on silica gel to give the title compound.

Mpt.238-240° C.

LCMS (method 1): retention time: 1.01 min; 503 (M+H).

$^1$H NMR (400 MHz, DMSO-d6) δ1.13 (t, 3H), 3.46 (q, 2H), 3.91 (s, 3H), 7.97 (s, 1H), 8.73 (s, 1H); $^{19}$F-NMR (400 Mz, DMSO-d₆) δ: −62.28 (s, 3F); ESI-MS(+): 503 (M+H)⁺, 425 (M+Na)⁺.

Step C: Preparation of 6-[3-ethylsulfonyl-5-[3-(trifluoromethyl)pyrazol-1-yl]-2-thienyl]-7-methyl-3-(trifluoromethyl)imidazo[4,5-c]pyridazine (Compound 26.017, Example P-12, Table P)

(Compound 26.017, example P-12, table P)

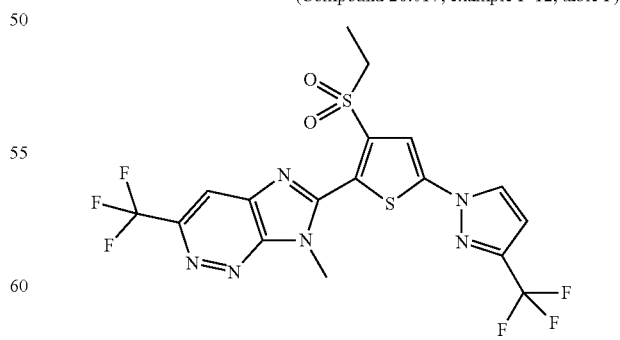

Under the protection of nitrogen, 6-(3-ethylsulfonyl-5-iodo-2-thienyl)-7-methyl-3-(trifluoromethyl)imidazo[4,5-c]pyridazine (251 mg, 0.5 mmol) was added to a mixture of 3-(trifluoromethyl)-1H-pyrazole (204 mg, 1.5 mmol), potassium carbonate (207 mg, 1.5 mmol), CuI (10 mg, 0.05 mmol) and DMEDA (4.5 mg, 0.05 mmol) in 10 ml of 1,4-dioxane. After the addition, the mixture was refluxed for 16 h. Then, the mixture was poured into water and extracted with ethyl acetate three times. The combined organic layers were dried over sodium sulfate, filtered and concentrated in vacuo. The crude product was purified by column chromatography on silica gel to give the title compound.

Mpt: 162-164° C.

LCMS (method 1): retention time: 1.10 min; 512 (M+H).

$^1$H NMR (400 MHz, CDCl$_3$) δ 1.38 (t, 3H), 3.41 (q, 2H), 4.13 (s, 3H), 6.84 (d, 1H), 7.58 (s, 1H), 8.03 (d, 1H), 8.21 (s, 1H); $^{19}$F-NMR (400 Mz, CDCl$_3$) δ: −71.11 (s, 3F), −68.80 (s, 3F);

Example 17

Preparation of 5-ethylsulfonyl-4-[3-methyl-6-(trifluoromethyl)imidazo[4,5-c]pyridin-2-yl]-2-pyrimidin-2-yl-thiazole (Compound 32.016, Example P-23, Table P)

(Compound 32.016, example P-23, table P)

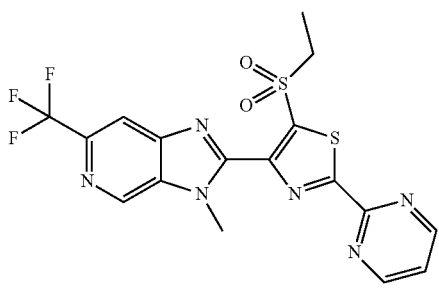

Step A: Preparation of ethyl 5-ethylsulfanylthiazole-4-carboxylate

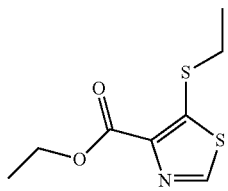

A solution of ethyl isocyanoacetate (5.6 g, 0.05 mol) in 100 ml of THF was added dropwise to a suspension of potassium tert-butoxide (6.1 g, 0.055 mol) in 20 ml of THF at −40° C. The mixture was cooled to −60° C., and a solution of carbon disulfide (3.8 g, 0.05 mol) was added dropwise while keeping the temperature below −50° C. The mixture was warmed to 10° C. and ethyl bromide (5.4 g, 0.05 mol) was added. The mixture was allowed to stir for 2 h and was concentrated in vacuum. The product was purified by column chromatography on silica gel to get the title compound.

$^1$H NMR (400 MHz, DMSO-d$_6$) δ 1.27-1.37 (m, 6H), 3.03-3.10 (q, 2H), 4.25-4.32 (q, 2H), 8.92 (s, 1H).

ESI-MS: 240 (M+Na$^+$).

Step B: Preparation of ethyl 2-bromo-5-ethylsulfanyl-thiazole-4-carboxylate

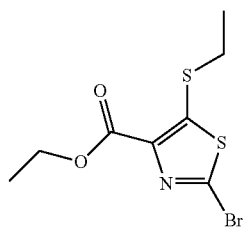

Bromine (0.48 g, 3 mmol) was added to the solution of ethyl 5-ethylsulfanylthiazole-4-carboxylate (219 mg, 1 mmol) in 10 ml of CCl$_4$ at 0° C. The mixture was stirred overnight at rt, the mixture was poured into water, and extracted with dichloromethane three times. The combined organic layers were dried over sodium sulfate, filtered and concentrated in vacuo. The crude product was purified by column chromatography on silica gel to give the title compound.

$^1$H-NMR (400 Mz, DMSO-d$_6$) δ: δ 1.32-1.24 (m, 6H), 3.03-3.00 (q, 2H), 4.27-4.21 (q, 2H).

ESI-MS: 219 (M+Na$^+$).

Step C: Preparation of 2-bromo-5-ethylsulfanyl-thiazole-4-carboxylic acid

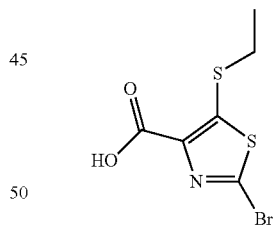

A mixture of ethyl 2-bromo-5-ethylsulfanyl-thiazole-4-carboxylate (2.92 g, 9.8 mol) and NaOH (780 mg, 19.6 mol) in 20 ml of water and 40 ml of THF was stirred at room temperature overnight. The reaction mixture was poured into diluted hydrochloric acid and concentrated in vacuo. Then, the deposited precipitate was filtrated, washed with water three times, and concentrated in vacuo, to obtain the title compound.

$^1$H NMR (400 MHz, DMSO-d$_6$) δ 1.31-1.18 (t, 3H), 3.03-2.97 (q, 2H), 13.32 (s, 1H);

ESI-MS: 291 (M+Na$^+$).

Step D: Preparation of 2-bromo-5-ethylsulfanyl-thiazole-4-carbonyl chloride

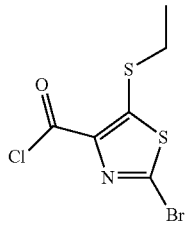

Oxalyl chloride (1.5 g, 12 mmol) and DMF(one drop) was added to the solution of 2-bromo-5-ethylsulfanyl-thiazole-4-carboxylic acid (540 mg, 2 mmol) in 10 ml of dichloromethane at r.t. The mixture was stirred overnight at r.t. Then the mixture was concentrated in vacuo to get the title compound.

Step E: Preparation of 2-bromo-5-ethylsulfanyl-4-[3-methyl-6-(trifluoromethyl)imidazo[4,5-c]pyridin-2-yl]thiazole

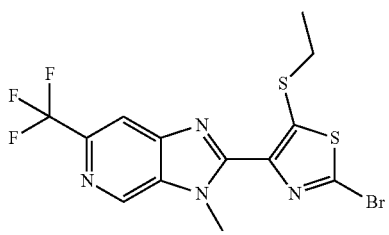 [SMILES: CCSc1sc(Br)nc1-c1nc2cc(C(F)(F)F)ncc2n1C]

A sample of 2-bromo-5-ethylsulfanyl-thiazole-4-carbonyl chloride (310 mg, 1.08 mol) and N3-methyl-6-(trifluoromethyl)pyridine-3,4-diamine (216 mg, 1.03 mol) in 10 ml of toluene was refluxed for 24 h, and the mixture then concentrated in vacuo. The crude product was refluxed for 16 h in 10 ml of AcOH, the mixture was concentrated in vacuo and purified by column chromatography on silica gel to give the title compound.

$^1$H-NMR (400 MHz, DMSO-d$_6$) δ 1.30-1.31 (t, 3H), 3.07-3.09 (q, 2H), 4.16 (s, 3H), 8.17 (s, 1H), 9.15 (s, 1H);
$^{19}$F-NMR (300 MHz, DMSO-d$_6$) δ −65.75 (s, 3F);
ESI-MS: 424 (M+H$^+$).

Step F: Preparation of 2-bromo-5-ethylsulfonyl-4-[3-methyl-6-(trifluoromethyl)imidazo[4,5-c]pyridin-2-yl]thiazole (Compound I-9, Table I)

(Compound I-9, table I)

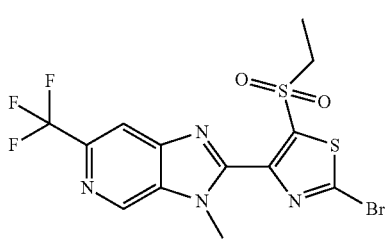

A sample of 2-bromo-5-ethylsulfanyl-4-[3-methyl-6-(trifluoromethyl)imidazo[4,5-c]pyridin-2-yl]thiazole (212 mg, 0.5 mmol) and m-CPBA (431 mg, 2.5 mmol) in 10 ml of dichloromethane was stirred at room temperature for 2 h. Then the mixture was poured into a saturated solution of Na$_2$CO$_3$ and Na$_2$SO$_3$ in water, and extracted with ethyl acetate three times. The combined organic layers were dried over sodium sulfate, filtered and concentrated in vacuo. The crude product was purified by column chromatography on silica gel to give the title compound.

Mpt:177-179° C.

LCMS (method 1): retention time: 1.05 min; 455/457 (M+H).

$^1$H-NMR (400 MHz, DMSO-d$_6$) δ 1.28-1.31 (t, 3H), 4.05-4.08 (m, 5H), 830 (s, 1H), 9.25 (s, 1H);
$^{19}$F-NMR (300 MHz, DMSO-d$_6$) δ −65.78 (s, 3F)

Step G: Preparation of 5-ethylsulfonyl-4-[3-methyl-6-(trifluoromethyl)imidazo[4,5-c]pyridin-2-yl]-2-pyrimidin-2-yl-thiazole (Compound 32.016, Example P-23, Table P)

(Compound 32.016, example P-23, table P)

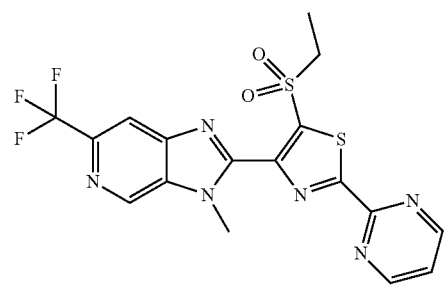

Under the protection of nitrogen, 2-bromo-5-ethylsulfonyl-4-[3-methyl-6-(trifluoromethyl)imidazo[4,5-c]pyridin-2-yl]thiazole (228 mg, 0.5 mmol), PdCl$_2$(PPh)$_2$ (35 mg, 0.05 mmol), CuI (19 mg, 0.1 mmol) and tributyl(pyrimidin-2-yl)stannane (369 mg, 1 mmol) were dissolved in 20 ml of 1,4-dioxane. After the addition, the mixture was refluxed for 2 h. Then, the mixture was poured into water and extracted with ethyl acetate three times. The combined organic layers were dried over sodium sulfate, filtered and concentrated in vacuo. The crude product was purified by column chromatography on silica gel to give the title compound.

Mpt:258-260° C.

LCMS (method 1): retention time: 0.97 min; 455 (M+H).

$^1$H-NMR (400 MHz, CDCl$_3$) δ 1.47-1.50 (t, 3H), 4.03-4.05 (q, 2H), 4.13 (s, 3H), 7.46 (s, 1H), 8.10 (s, 1H), 8.91 (s, 2H), 8.96 (s, 1H).

$^{19}$F-NMR (300 MHz, CDCl$_3$) δ −69.58 (s, 3F)

Example H-18: Preparation of 2-cyclopropyl-5-ethylsulfonyl-4-[3-methyl-6-(trifluoromethyl)imidazo[4,5-c]pyridin-2-yl]thiazole (Compound 32.021, Example P-22, Table P)

(Compound 32.021, example P-22, table P)

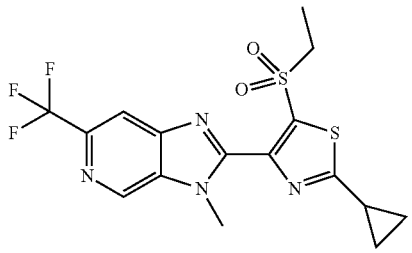

Under the protection of nitrogen, 2-bromo-5-ethylsulfonyl-4-[3-methyl-6-(trifluoromethyl)imidazo[4,5-c]pyridin-2-yl]thiazole (273 mg, 0.6 mmol), Pd(PPh$_3$)$_4$ (9 mg, 0.06 mmol), K$_2$CO$_3$ (249 mg, 1.8 mmol) and cyclopropylboronic acid (103 mg, 1.2 mmol) were dissolved in 20 ml of 1,4-dioxane. After the addition, the mixture was refluxed for 20 h. Then, the mixture was poured into water and extracted with ethyl acetate three times. The combined organic layers were dried over sodium sulfate, filtered and concentrated in vacuo. The crude product was purified by column chromatography on silica gel to give the title compound.

Mpt: 167-168° C.

LCMS (method 1): retention time: 1.05 min; 417 (M+H).

$^1$H-NMR (400 MHz, CDCl$_3$) δ 1.23-1.25 (m, 2H), 1.29-1.33 (m, 2H), 1.41-1.45 (t, 3H), 2.36-2.40 (m, 1H), 3.93-3.99 (q, 2H), 4.03 (s, 3H), 8.08 (s, 1H), 8.92 (s, 1H); $^{19}$F-NMR (300 MHz, CDCl$_3$) δ −71.34 (s, 3F)

Example H-19: Preparation of 2-(4-chlorophenyl)-5-ethylsulfonyl-4-[3-methyl-6-(trifluoromethyl)imidazo[4,5-c]pyridin-2-yl]thiazole (Compound 32.004, Example P-19, Table P)

(Compound 32.004, example P-19, table P)

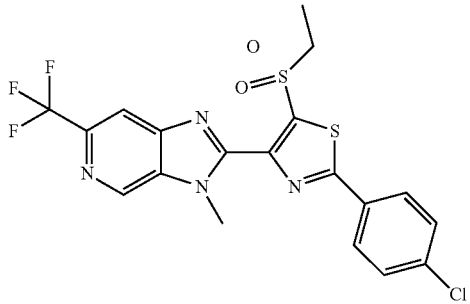

Step A: Preparation of ethyl 2-(4-chlorophenyl)-5-ethylsulfanyl-thiazole-4-carboxylate

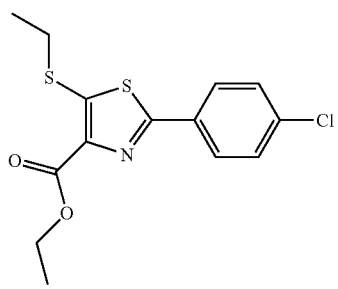 [SMILES: CCOC(=O)c1nc(-c2ccc(Cl)cc2)sc1SCC]

Under the protection of nitrogen, ethyl 2-bromo-5-ethylsulfanyl-thiazole-4-carboxylate (296 mg, 1 mmol), Pd(PPh$_3$)$_4$ (116 mg, 0.1 mmol), K$_2$CO$_3$ (415 mg, 3 mmol) and (4-chlorophenyl)boronic acid (235 mg, 1.5 mmol) were dissolved in 20 ml of 1,4-dioxane. After the addition, the mixture was refluxed for 16 h. Then, the mixture was poured into water and extracted with ethyl acetate three times. The combined organic layers were dried over sodium sulfate, filtered and concentrated in vacuo. The crude product was purified by column chromatography on silica gel to give the title compound.

$^1$H-NMR (400 MHz, DMSO-d$_6$) δ 1.25-1.37 m, 6H), 3.09-3.12 (q, 2H), 4.26-4.31 (q, 2H), 7.53-7.55 (dd, 2H), 7.85-7.88 (dd, 2H); ESI-MS: 328 (M+H$^+$).

Step B: Preparation of 2-(4-chlorophenyl)-5-ethylsulfanyl-thiazole-4-carboxylic acid

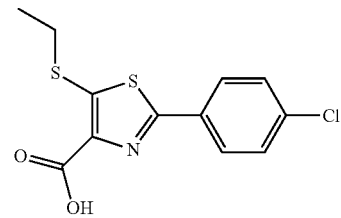 [SMILES: CCSc1sc(-c2ccc(Cl)cc2)nc1C(=O)O]

A mixture of ethyl 2-(4-chlorophenyl)-5-ethylsulfanyl-thiazole-4-carboxylate (721 mg, 2.2 mmol) and NaOH (440 mg, 11 mmol) in 20 ml of water and 40 ml of THF was stirred at room temperature overnight. Then, the reaction mixture was poured into diluted hydrochloric acid and concentrated in vacuo. Then, the deposited precipitate was filtrated, washed with water three times, dried under reduced pressure to obtain the title compound.

$^1$H NMR (400 MHz, DMSO-d$_6$) δ 1.32-1.36 (t, 3H), 3.04-3.07 (q, 2H), 7.52-7.55 (dd, 2H), 7.85-7.87 (dd, 2H). ESI-MS: 299 (M+Na$^+$).

Step C: Preparation of Compound 2-(4-chlorophenyl)-5-ethylsulfanyl-thiazole-4-carbonyl chloride

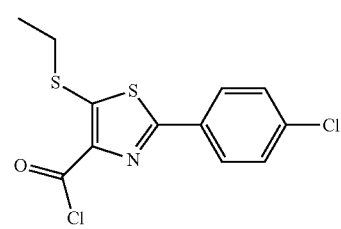 [SMILES: CCSc1sc(-c2ccc(Cl)cc2)nc1C(=O)Cl]

A sample of Oxalyl chloride (1.14 g, 9 mmol) and DMF(one drop) was added to the solution of 2-(4-chlorophenyl)-5-ethylsulfanyl-thiazole-4-carboxylic acid (450 mg, 1.5 mmol) in 10 ml of dichloromethane at r.t. The mixture was stirred overnight at r.t. Then the mixture was concentrated in vacuo to get the title compound.

Step D: Preparation of 2-(4-chlorophenyl)-5-ethyl-sulfanyl-4-[3-methyl-6-(trifluoromethyl)imidazo[4,5-c]pyridin-2-yl]thiazole (Compound 31.004, Example P-27, Table P)

(Compound 31.004, example P-27, table P)

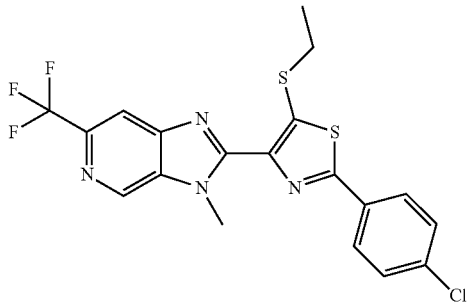

A sample of 2-(4-chlorophenyl)-5-ethylsulfanyl-thiazole-4-carbonyl chloride (541 mg, 1.7 mol) and N3-methyl-6-(trifluoromethyl)pyridine-3,4-diamine (325 mg, 1.7 mol) in 10 ml of toluene was refluxed for 48 h, then the mixture was concentrated in vacuo. The residue obtained was refluxed for 16 h in 10 ml of AcOH, concentrated in vacuo and purified by column chromatography on silica gel to give the title compound.

$^1$H-NMR (400 MHz, DMSO-d$^6$) δ 1.27-1.32 (t, 3H), 4.03-4.07 (q, 2H), 4.09 (s, 3H), 7.49 (d, 2H), 7.86 (d, 2H), 8.31 (s, 1H), 9.12 (s, 1H).
$^{19}$F-NMR (300 MHz, CDCl$_3$) δ −68.3 (s, 3F).
ESI-MS: 509 (M+Na$^+$).

Step E: Preparation of 2-(4-chlorophenyl)-5-ethyl-sulfonyl-4-[3-methyl-6-(trifluoromethyl)imidazo[4,5-c]pyridin-2-yl]thiazole (Compound 32.004, Example P-19, Table P)

(Compound 32.004, example P-19, table P)

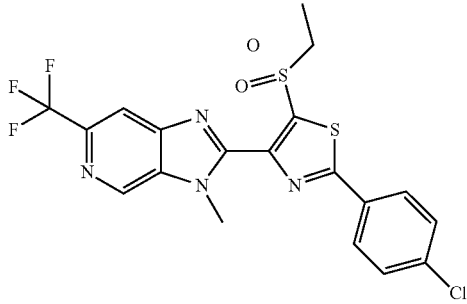

A sample of 2-(4-chlorophenyl)-5-ethylsulfanyl-4-[3-methyl-6-(trifluoromethyl)imidazo[4,5-c]pyridin-2-yl]thiazole (168 mg, 0.37 mmol) and m-CPBA (323 mg, 1.87 mmol) in 10 ml of dichloromethane was stirred at room temperature for 2 h. Then the mixture was poured into a saturated solution of Na$_2$CO$_3$ and Na$_2$SO$_3$ in water, and extracted with ethyl acetate three times. The combined organic layers were dried over sodium sulfate, filtered and concentrated in vacuo. The crude product was purified by column chromatography on silica gel to give the title compound.

Mpt. 215-216° C.
LCMS (method 1): retention time: 1.22 min; 487 (M+H).
$^1$H-NMR (400 MHz, CDCl$_3$) δ 1.47-1.50 (t, 3H), 4.06-4.08 (q, 2H), 4.14 (s, 3H), 7.50 (d, 2H), 7.94 (d, 2H), 8.12 (s, 1H), 8.97 (s, 1H).
$^{19}$F-NMR (300 MHz, CDCl$_3$) δ −70.69 (s, 3F);

Example H-20: Preparation of 5-ethylsulfonyl-4-[3-methyl-6-(trifluoromethyl)imidazo[4,5-c]pyridin-2-yl]-2-[3-(trifluoromethyl)pyrazol-1-yl]thiazole (Compound 32.017, Example P-20, Table P)

(Compound 32.017, example P-20, table P)

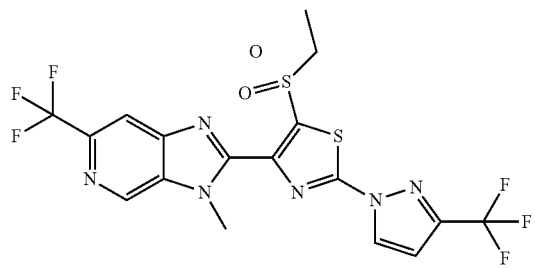

Step A: Preparation of ethyl 5-ethylsulfanyl-2-[3-(trifluoromethyl)pyrazol-1-yl]thiazole-4-carboxylate

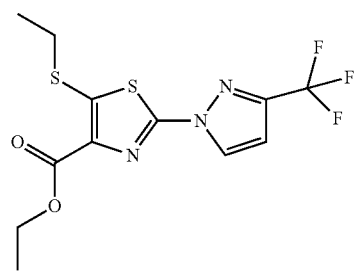 [SMILES: CCOC(=O)c1nc(-n2ccc(C(F)(F)F)n2)sc1SCC]

Under the protection of nitrogen, ethyl 2-bromo-5-ethyl-sulfanyl-thiazole-4-carboxylate (296 mg, 1 mmol), CuI (19 mg, 0.1 mmol), DMEDA (9 mg, 0.1 mmol), K$_2$CO$_3$ (553 mg, 4 mmol) and 3-(trifluoromethyl)-1H-pyrazole (544 mg, 4 mmol) were dissolved in 20 ml of 1,4-dioxane. After the addition, the mixture was refluxed for 3 h. Then, the mixture was poured into water and extracted with ethyl acetate three times. The combined organic layers were dried over sodium sulfate, filtered and concentrated in vacuo. The crude product was purified by column chromatography on silica gel to give the title compound.

$^1$H-NMR (400 MHz, DMSO-d$_6$) δ 1.26-1.36 (t, 3H), 3.09-3.15 (q, 2H), 4.26-4.31 (q, 2H), 7.13 (s, 1H), 8.71 (s, 1H).
$^{19}$F-NMR (300 MHz, DMSO-d$_6$) δ −66.14 (s, 3F).
ESI-MS: 352 (M+H$^+$).

Step B: Preparation of 5-ethylsulfanyl-2-[3-(trifluoromethyl)pyrazol-1-yl]thiazole-4-carboxylic acid

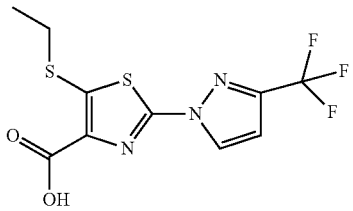 [SMILES: CCSc1sc(-n2ccc(C(F)(F)F)n2)nc1C(=O)O]

A mixture of ethyl 5-ethylsulfanyl-2-[3-(trifluoromethyl)pyrazol-1-yl]thiazole-4-carboxylate (500 mg, 1.42 mol) and NaOH (284 mg, 7.1 mol) in 20 ml of water and 40 ml of THF was stirred at room temperature overnight. Then, the reaction mixture was poured into diluted hydrochloric acid and concentrated in vacuo. Then, the deposited precipitate was filtrated, washed with water three times, dried under reduced pressure to obtain the title compound.

$^1$H NMR (400 MHz, DMSO-$d_6$) δ 1.32-1.35 (t, 3H), 3.07-3.13 (q, 2H), 7.13 (s, 1H), 8.68 (s, 1H), 13.28 (s, 1H)
$^{19}$F-NMR (300 MHz, DMSO-$d_6$) δ −66.80 (s, 3F); ESI-MS: 322 (M−1).

Step C: Preparation of 5-ethylsulfanyl-2-[3-(trifluoromethyl)pyrazol-1-yl]thiazole-4-carbonyl chloride

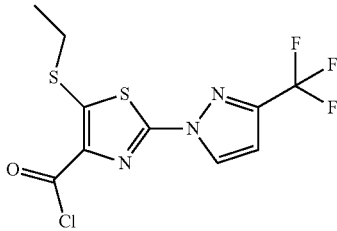 [SMILES: CCSc1sc(-n2ccc(C(F)(F)F)n2)nc1C(=O)Cl]

A sample of Oxalyl chloride (1.14 g, 9 mmol) and DMF(one drop) was added to a solution of 5-ethylsulfanyl-2-[3-(trifluoromethyl)pyrazol-1-yl]thiazole-4-carboxylic acid (485 mg, 1.5 mmol) in 10 ml of dichloromethane at r.t. The mixture was stirred overnight at r.t. Then the mixture was concentrated in vacuo to give the title compound.

Step D: Preparation of 5-ethylsulfanyl-4-[3-methyl-6-(trifluoromethyl)imidazo[4,5-c]pyridin-2-yl]-2-[3-(trifluoromethyl)pyrazol-1-yl]thiazole (Compound 31.017, Example P-21, Table P)

(Compound 31.017, example P-21, table P)

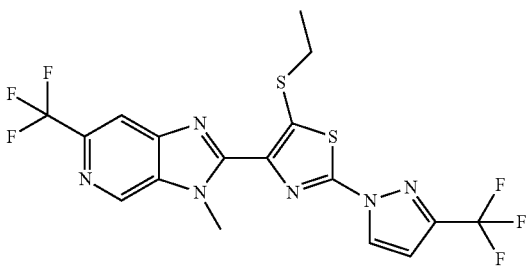

A sample of 5-ethylsulfanyl-2-[3-(trifluoromethyl)pyrazol-1-yl]thiazole-4-carbonyl chloride (574 mg, 1.68 mol) and N3-methyl-6-(trifluoromethyl)pyridine-3,4-diamine (325 mg, 1.7 mol) in 10 ml of toluene was refluxed for 48 h, and then the mixture was concentrated in vacuo. The crude product was purified by column chromatography on silica gel to give the title compound.

Mpt. 194-196° C.

LCMS (method 1): retention time: 1.28 min; 479 (M+H).

$^1$H-NMR (400 MHz, DMSO-$d_6$) δ 1.30-1.34 (t, 3H), 3.13-3.15 (q, 2H), 4.24 (s, 3H), 7.20 (s, 1H), 8.44 (s, 1H), 8.91 (s, 1H), 9.17 (s, 1H)
$^{19}$F-NMR (300 MHz, DMSO-$d_6$) δ −67.37 (s, 3F), −70.59 (s, 3F)

Step E: Preparation of 5-ethylsulfonyl-4-[3-methyl-6-(trifluoromethyl)imidazo[4,5-c]pyridin-2-yl]-2-[3-(trifluoromethyl)pyrazol-1-yl]thiazole (Compound 32.017, Example P-20, Table P)

(Compound 32.017, example P-20, table P)

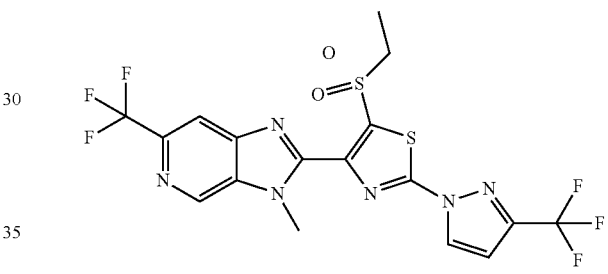

5-ethylsulfanyl-4-[3-methyl-6-(trifluoromethyl)imidazo[4,5-c]pyridin-2-yl]-2-[3-(trifluoromethyl)pyrazol-1-yl]thiazole (200 mg, 0.42 mmol) and m-CPBA (361 mg, 2.09 mmol) in 10 ml of dichloromethane was stirred at room temperature for 2 h. Then the mixture was poured into a saturated solution of $Na_2CO_3$ and $Na_2SO_3$ in water, and extracted with ethyl acetate three times. The combined organic layers were dried over sodium sulfate, filtered and concentrated in vacuo. The crude product was purified by column chromatography on silica gel to give the title compound.

Mpt: 100-101° C.

LCMS (method 1): retention time: 1.19 min; 512 (M+H).

$^1$H-NMR (400 MHz, CDCl$_3$) δ 1.47-1.51 (t, 3H), 4.00-4.04 (q, 2H), 4.11 (s, 3H), 6.83 (s, 1H), 8.12 (s, 1H), 8.40 (s, 1H), 8.98 (s, 1H)
$^{19}$F-NMR (300 MHz, CDCl$_3$) δ−62.87 (s, 3F), −66.19 (s, 3F)

Compounds in tables 1-38 can be prepared analogously to the methods described above.

TABLE P

Examples of compounds of formula (I)

| Entry | STRUCTURE | RT (min) | [M + H] (measured) | Method | Mpt. ° C. |
|---|---|---|---|---|---|
| P-1 | 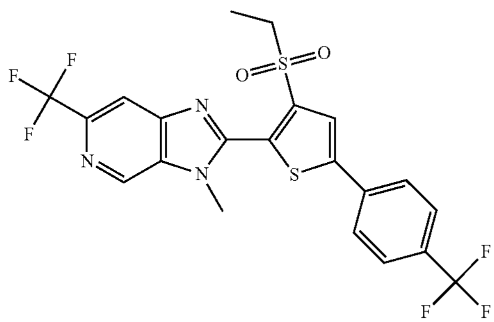 [SMILES: CCS(=O)(=O)c1cc(-c2ccc(C(F)(F)F)cc2)sc1-c1nc2cc(C(F)(F)F)ncc2n1C] | 1.13 | 520 | 1 | 181-183 |
| P-2 | 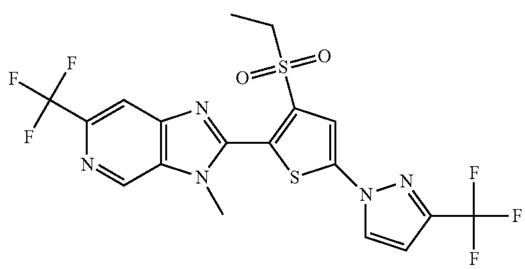 [SMILES: CCS(=O)(=O)c1cc(-n2ccc(C(F)(F)F)n2)sc1-c1nc2cc(C(F)(F)F)ncc2n1C] | 1.06 | 510 | 1 | 173-175 |
| P-3 | 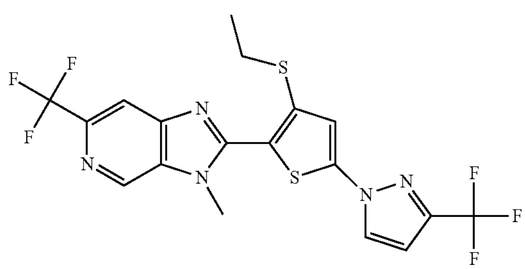 [SMILES: CCSc1cc(-n2ccc(C(F)(F)F)n2)sc1-c1nc2cc(C(F)(F)F)ncc2n1C] | 1.16 | 478 | 1 | 162-164 |
| P-4 | 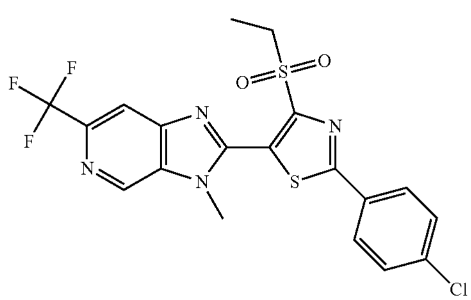 [SMILES: CCS(=O)(=O)c1nc(-c2ccc(Cl)cc2)sc1-c1nc2cc(C(F)(F)F)ncc2n1C] | 1.03 | 487 | 1 | 230-232 |
| P-5 | 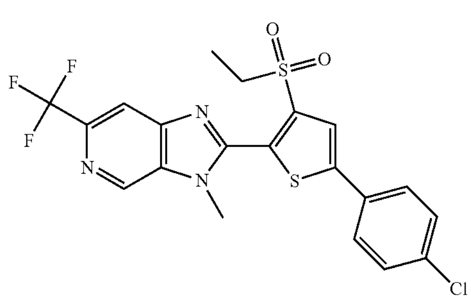 [SMILES: CCS(=O)(=O)c1cc(-c2ccc(Cl)cc2)sc1-c1nc2cc(C(F)(F)F)ncc2n1C] | 1.08 | 486 | 1 | 170-172 |

TABLE P-continued

Examples of compounds of formula (I)

| Entry | STRUCTURE | RT (min) | [M + H] (measured) | Method | Mpt. ° C. |
|---|---|---|---|---|---|
| P-6 | 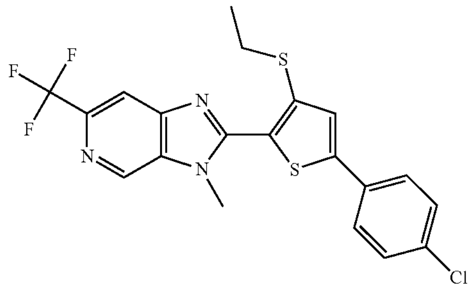 [SMILES: CCSc1cc(-c2ccc(Cl)cc2)sc1-c1nc2cc(C(F)(F)F)ncc2n1C] | 1.21 | 454 | 1 | 146-148 |
| P-7 | 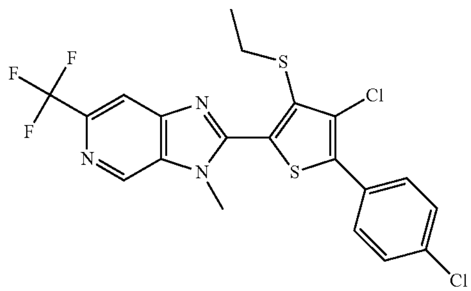 [SMILES: CCSc1c(-c2nc3cc(C(F)(F)F)ncc3n2C)sc(-c2ccc(Cl)cc2)c1Cl] | 1.29 | 488 | 1 | 116-118 |
| P-8 | 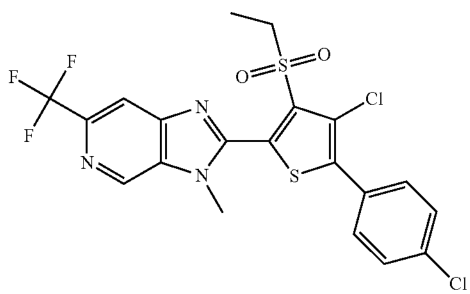 [SMILES: CCS(=O)(=O)c1c(-c2nc3cc(C(F)(F)F)ncc3n2C)sc(-c2ccc(Cl)cc2)c1Cl] | 1.14 | 520 | 1 | 212-214 |
| P-9 | 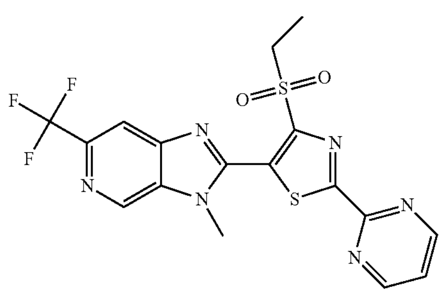 [SMILES: CCS(=O)(=O)c1nc(-c2ncccn2)sc1-c1nc2cc(C(F)(F)F)ncc2n1C] | 0.87 | 455 | 1 | — |
| P-10 | 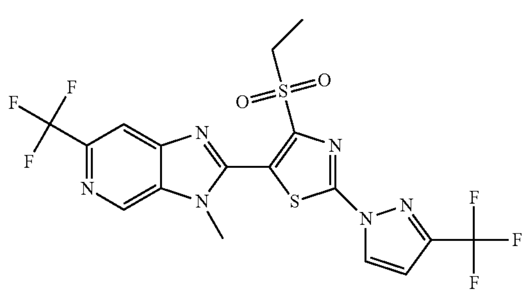 [SMILES: CCS(=O)(=O)c1nc(-n2ccc(C(F)(F)F)n2)sc1-c1nc2cc(C(F)(F)F)ncc2n1C] | 1.07 | 511 | 1 | 185-187 |

TABLE P-continued

Examples of compounds of formula (I)

| Entry | STRUCTURE | RT (min) | [M + H] (measured) | Method | Mpt. ° C. |
|---|---|---|---|---|---|
| P-11 | 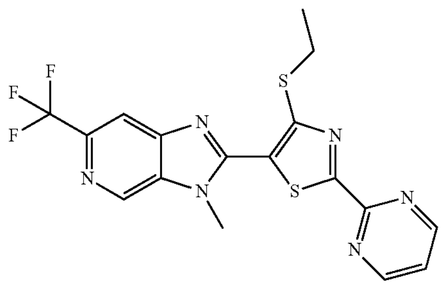 [SMILES: CCSc1nc(-c2ncccn2)sc1-c1nc2cc(C(F)(F)F)ncc2n1C] | 0.96 | 423 | 1 | 230-232 |
| P-12 | 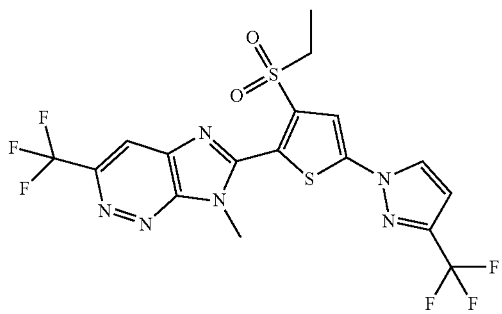 [SMILES: CCS(=O)(=O)c1cc(-n2ccc(C(F)(F)F)n2)sc1-c1nc2cc(C(F)(F)F)nnc2n1C] | 1.10 | 512 | 1 | 162-164 |
| P-13 | 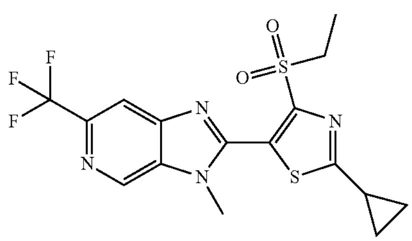 [SMILES: CCS(=O)(=O)c1nc(C2CC2)sc1-c1nc2cc(C(F)(F)F)ncc2n1C] | 0.94 | 417 | 1 | 166-168 |
| P-14 | 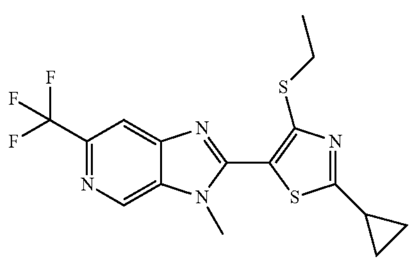 [SMILES: CCSc1nc(C2CC2)sc1-c1nc2cc(C(F)(F)F)ncc2n1C] | 1.14 | 385 | 1 | 97-99 |
| P-15 | 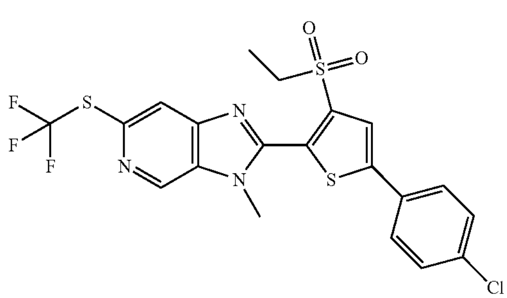 [SMILES: CCS(=O)(=O)c1cc(-c2ccc(Cl)cc2)sc1-c1nc2cc(SC(F)(F)F)ncc2n1C] | 1.20 | 519 | 1 | 148-150 |

TABLE P-continued

Examples of compounds of formula (I)

| Entry | STRUCTURE | RT (min) | [M + H] (measured) | Method | Mpt. ° C. |
|---|---|---|---|---|---|
| P-16 | 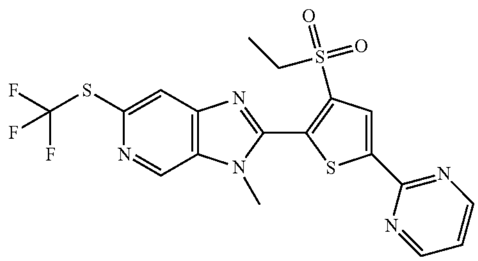 [SMILES: CCS(=O)(=O)c1cc(-c2ncccn2)sc1-c1nc2cc(SC(F)(F)F)ncc2n1C] | 1.01 | 487 | 1 | 261-262 |
| P-17 | 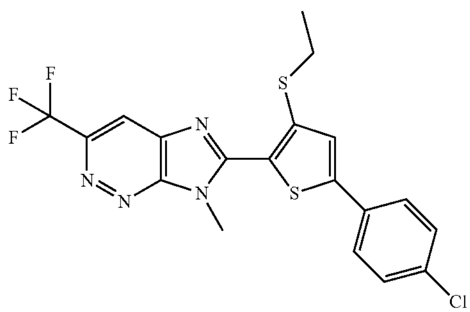 [SMILES: CCSc1cc(-c2ccc(Cl)cc2)sc1-c1nc2cc(C(F)(F)F)nnc2n1C] | 1.27 | 455/457 | 1 | 205-207 |
| P-18 | 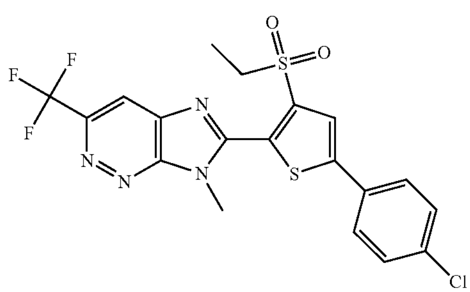 [SMILES: CCS(=O)(=O)c1cc(-c2ccc(Cl)cc2)sc1-c1nc2cc(C(F)(F)F)nnc2n1C] | 1.13 | 487/489 | 1 | 166-168 |
| P-19 | 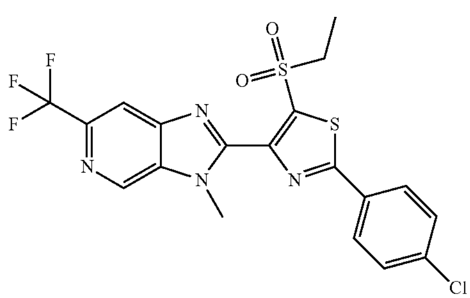 [SMILES: CCS(=O)(=O)c1sc(-c2ccc(Cl)cc2)nc1-c1nc2cc(C(F)(F)F)ncc2n1C] | 1.22 | 597/489 | 1 | 215-216 |
| P-20 | 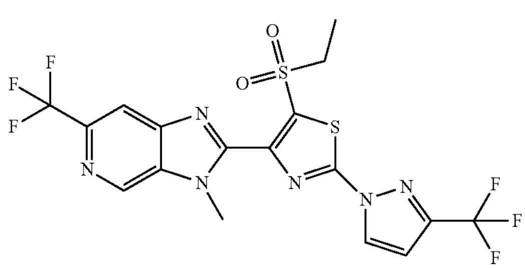 [SMILES: CCS(=O)(=O)c1sc(-n2ccc(C(F)(F)F)n2)nc1-c1nc2cc(C(F)(F)F)ncc2n1C] | 1.19 | 512 | 1 | 100-101 |

TABLE P-continued

Examples of compounds of formula (I)

| Entry | STRUCTURE | RT (min) | [M + H] (measured) | Method | Mpt. ° C. |
|---|---|---|---|---|---|
| P-21 | 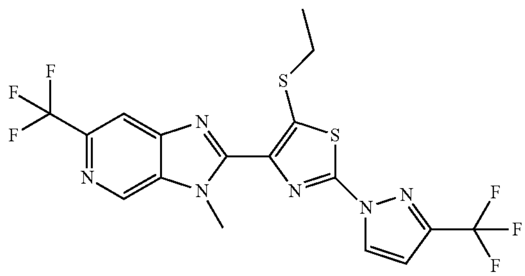 [SMILES: CCSc1sc(-n2ccc(C(F)(F)F)n2)nc1-c1nc2cc(C(F)(F)F)ncc2n1C] | 1.29 | 480 | 1 | 194-196 |
| P-22 | 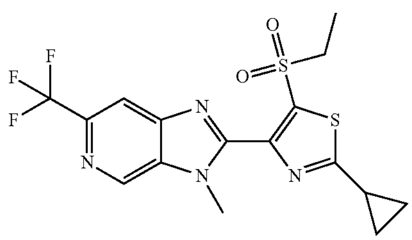 [SMILES: CCS(=O)(=O)c1sc(C2CC2)nc1-c1nc2cc(C(F)(F)F)ncc2n1C] | 1.05 | 417 | 1 | 167-168 |
| P-23 | 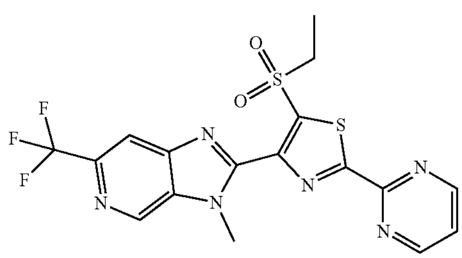 [SMILES: CCS(=O)(=O)c1sc(-c2ncccn2)nc1-c1nc2cc(C(F)(F)F)ncc2n1C] | 0.97 | 455 | 1 | 258-260 |
| P-24 | 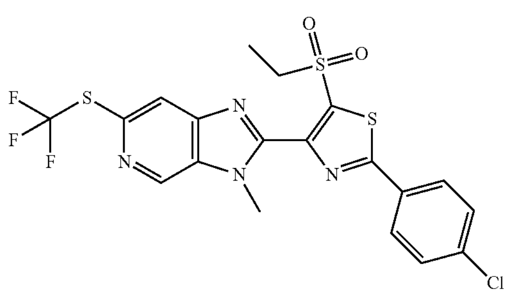 [SMILES: CCS(=O)(=O)c1sc(-c2ccc(Cl)cc2)nc1-c1nc2cc(SC(F)(F)F)ncc2n1C] | 1.24 | 520 | 1 | 223-224 |
| P-25 | 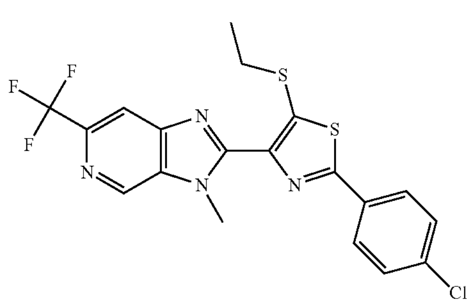 [SMILES: CCSc1sc(-c2ccc(Cl)cc2)nc1-c1nc2cc(C(F)(F)F)ncc2n1C] | — | — | — | $^1$H NMR (400 Mz, DMSO-d$_6$): δ 1.30 (t, 3H), 3.31 (q, 2H), 4.09 (s, 3H), 7.65 (d, 2H), 8.08 (d, 2H), 8.24 (s, 1H), 9.22 (s, 1H); |

TABLE P-continued

Examples of compounds of formula (I)

| Entry | STRUCTURE | RT (min) | [M + H] (measured) | Method | Mpt. ° C. |
|---|---|---|---|---|---|
| P26 | ![structure] | 1.20 | 521 | 1 | 203-204 |
| P27 | ![structure] | — | — | — | ¹H-NMR (400 MHz, DMSO-d⁶) δ 1.27-1.32 (t, 3H), 4.03-4.07 (q, 2H), 4.09 (s, 3H), 7.49 (d, 2H), 7.86(d, 2H), 8.31(s, 1H), 9.12 (s, 1H); ¹⁹F-NMR (300 MHz, CDCl₃) δ −68.3(s, 3F); ESI-MS: 477(M + Na⁺). |

Compounds of Formula IIa and IIb;

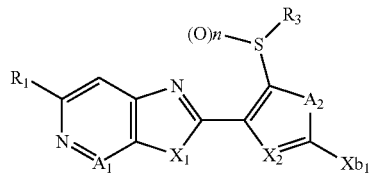

(IIa)

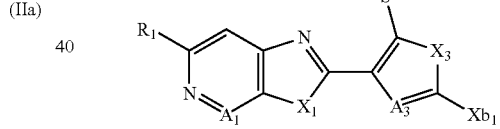

(IIb)

used as intermediates in the preparation of compounds of formula I, where $R_1$, $A_1$, $X_1$, $X_2$, $A_2$, $A_3$, $X_3$, and $R_3$ are a described in formula I, and Xb1 is halogen, with the proviso that IIb is not 2-bromo-5-ethylsulfonyl-4-[3-methyl-6-(trifluoromethyl)imidazo[4,5-c]pyridin-2-yl]thiazole, are novel and as such also form part of this invention. Said compounds of formula IIa and IIb also show pesticidal activity. Examples of such compounds are shown in Table I.

TABLE I

Table of intermediates used to prepare compounds of formula I.

| Entry | STRUCTURE | RT (min) | [M + H] (measured) | Method | Mpt. ° C. |
|---|---|---|---|---|---|
| I-1 | 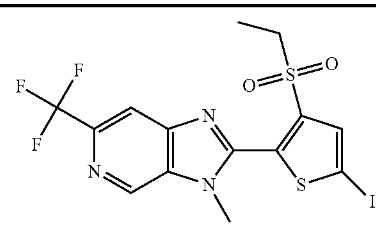 | 0.93 | 502 | 1 | 255-257 |

TABLE I-continued

Table of intermediates used to prepare compounds of formula I.

| Entry | STRUCTURE | RT (min) | [M + H] (measured) | Method | Mpt. ° C. |
|---|---|---|---|---|---|
| I-2 | 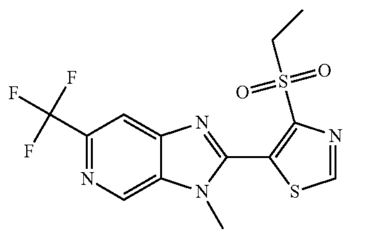 [SMILES: CCS(=O)(=O)c1ncsc1-c1nc2cc(C(F)(F)F)ncc2n1C] | 0.8 | 377 | | 169-171 |
| I-3 | 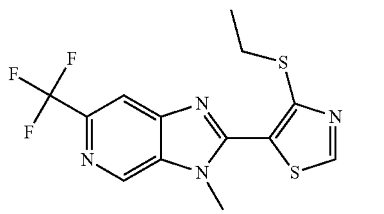 [SMILES: CCSc1ncsc1-c1nc2cc(C(F)(F)F)ncc2n1C] | 0.98 | 355 | 1 | 142-144 |
| I-4 | 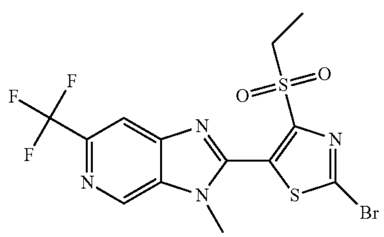 [SMILES: CCS(=O)(=O)c1nc(Br)sc1-c1nc2cc(C(F)(F)F)ncc2n1C] | 0.94 | 455/457 | 1 | 248-250 |
| I-5 | 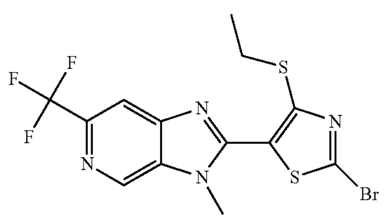 [SMILES: CCSc1nc(Br)sc1-c1nc2cc(C(F)(F)F)ncc2n1C] | 1.11 | 423/425 | 1 | 130-132 |
| I-6 | 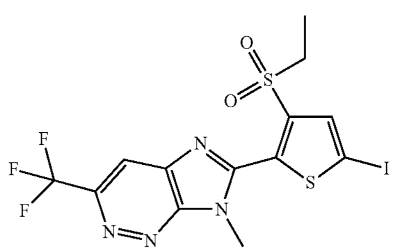 [SMILES: CCS(=O)(=O)c1cc(I)sc1-c1nc2cc(C(F)(F)F)nnc2n1C] | 1.01 | 503 | 1 | 238-240 |
| I-7 | 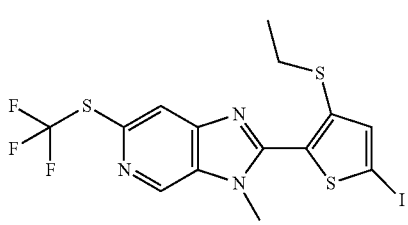 [SMILES: CCSc1cc(I)sc1-c1nc2cc(SC(F)(F)F)ncc2n1C] | 1.20 | 502 | 1 | — |

TABLE I-continued

Table of intermediates used to prepare compounds of formula I.

| Entry | STRUCTURE | RT (min) | [M + H] (measured) | Method | Mpt. ° C. |
|---|---|---|---|---|---|
| I-8 | 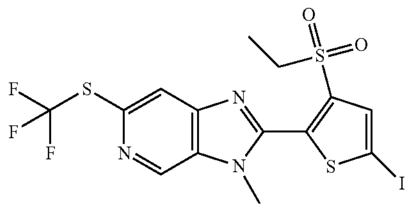 [SMILES: CCS(=O)(=O)c1cc(I)sc1-c1nc2cc(SC(F)(F)F)ncc2n1C] | 1.03 | 534 | 1 | 219-220 |
| I-9 | 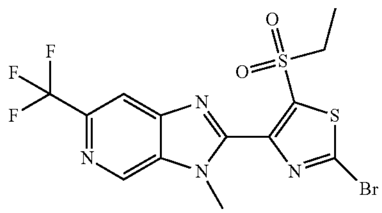 [SMILES: CCS(=O)(=O)c1sc(Br)nc1-c1nc2cc(C(F)(F)F)ncc2n1C] | 1.05 | 455/457 | 1 | 177-179 |
| I-10 | 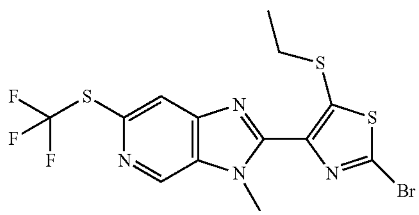 [SMILES: CCSc1sc(Br)nc1-c1nc2cc(SC(F)(F)F)ncc2n1C] | 1.22 | 455/457 | 1 | — |
| I-11 | 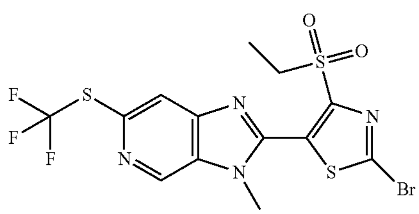 [SMILES: CCS(=O)(=O)c1nc(Br)sc1-c1nc2cc(SC(F)(F)F)ncc2n1C] | 1.08 | 487/489 | 1 | — |
| I-12 | 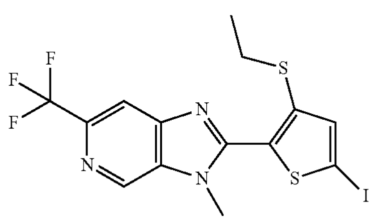 [SMILES: CCSc1cc(I)sc1-c1nc2cc(C(F)(F)F)ncc2n1C] | — | — | — | 61-63 |

Formulation Examples (%=Percent by Weight)

Example F1

Emulsion Concentrates

|  | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2

Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3

Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4

Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5

Wettable Powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8

Suspension Concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

Example F9

Powders for Dry Seed Treatment

|  | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

Example F10

Emulsifiable Concentrate

| active ingredient | 10% |
|---|---|
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Example F11

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 38 and P of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxath ion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin II (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis (dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4- ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure $B_1$ (839)+TX, trimedlure $B_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, Bacillus thuringiensis delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+

TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+

TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosphacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0)+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imiben-conazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L 190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a, 5,6,6a, 12,12a, 12b-decahydro-6,12-dihydroxy-4,6a, 12b-trimethyl-11-oxo-9-(3-pyridinyl)-2H, 11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX, microbials including: *Acinetobacter Iwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (AflaguarD®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuarD®)+TX, Green ReleaF®)+TX, *Bacillus circulans*+TX, *Bacillus firmus* (BioSafE®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield ShielD®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, SerenadE®+TX, RhapsodY®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (AgreE®)+TX, *Bacillus thuringiensis israelensis* (BMP123®+TX, AquabaC®+TX, VectoBaC®)+TX, *Bacillus thuringiensis kurstaki* (Javelin®+TX, Deliver®+TX, CryMax®+TX, BonidE®+TX, Scutella WP®+TX, Turilav WP®+TX, Astuto®+TX, Dipel WP®+TX, Biobit®+TX, ForaY®)+TX, *Bacillus thuringiensis kurstaki* BMP 123 (BaritonE®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTarI®+TX, DiPel®)+TX, bacteria spp. (GROWMEND®+TX, GROWSWEET®+TX, ShootuP®)+TX, bacteriophage of *Clavipacter michiganensis* (AgriPhagE®)+TX, Bakflor®+TX, *Beauveria bassiana* (BeaugeniC®+TX, Brocaril WP®)+TX, *Beauveria bassiana* GHA (Mycotrol ES®+TX, Mycotrol O®+TX, BotaniGuarD®)+TX, *Beauveria brongniartii* (Engerlingspilz®+TX, Schweizer *Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (DenY®+TX, Intercept®+TX, Blue CirclE®)+TX, *Burkholderia gladii*+TX, *Burkholderia gladioli*+TX, *Burkholderia* spp.+TX, Canadian thistle fungus (CBH Canadian BioherbicidE®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, BiocurE®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-CidE®)+TX, *Chaetomium globosum* (Nova-CidE®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFinE®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/CarpovirusinE®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (PrimastoP®+TX, PrestoP®)+TX, *Gliocladium roseum*+TX, *Gliocladium* spp. (SoilGarD®)+TX, *Gliocladium virens* (SoilgarD®)+TX, Granulovirus (GranupoM®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (MyconatE®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigfi*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomy-* ces linacinus (Biostat WP®)+TX, Paecilomyces lilacinus strain 251 (MeloCon WG®)+TX, Paenibacillus polymyxa+TX, Pantoea agglomerans (BlightBan C9-1®)+TX, Pantoea spp.+TX, Pasteuria spp. (EconeM®)+TX, Pasteuria nishizawae+TX, Penicillium aurantiogriseum+TX, Penicillium billai (Jumpstart®+TX, TagTeaM®)+TX, Penicillium brevicompactum+TX, Penicillium frequentans+TX, Penicillium griseofulvum+TX, Penicillium purpurogenum+TX, Penicillium spp.+TX, Penicillium viridicatum+TX, Phlebiopsis gigantean (RotstoP®)+TX, phosphate solubilizing bacteria (Phosphomeal®)+TX, Phytophthora cryptogea+TX, Phytophthora palmivora (DevinE®)+TX, Pichia anomala+TX, Pichia guilermondii+TX, Pichia membranaefaciens+TX, Pichia onychis+TX, Pichia stipites+TX, Pseudomonas aeruginosa+TX, Pseudomonas aureofasciens (Spot-Less BiofungicidE®)+TX, Pseudomonas cepacia+TX, Pseudomonas chlororaphis (AtEzE®)+TX, Pseudomonas corrugate+TX, Pseudomonas fluorescens strain A506 (BlightBan A506®)+TX, Pseudomonas putida+TX, Pseudomonas reactans+TX, Pseudomonas spp.+TX, Pseudomonas syringae (Bio-SavE®)+TX, Pseudomonas viridiflava+TX, Pseudomons fluorescens (Zequanox®)+TX, Pseudozyma flocculosa strain PF-A22 UL (Sporodex L®)+TX, Puccinia canaliculata+TX, Puccinia thlaspeos (Wood Warrior®)+TX, Pythium paroecandrum+TX, Pythium oligandrum (Polygandron®+TX, PolyversuM®)+TX, Pythium periplocum+TX, Rhanella aquatilis+TX, Rhanella spp.+TX, Rhizobia (Dormal®+TX, Vault®)+TX, Rhizoctonia+TX, Rhodococcus globerulus strain AQ719+TX, Rhodosporidium diobovatum+TX, Rhodosporidium toruloides+TX, Rhodotorula spp.+TX, Rhodotorula glutinis+TX, Rhodotorula graminis+TX, Rhodotorula mucilagnosa+TX, Rhodotorula rubra+TX, Saccharomyces cerevisiae+TX, Salinococcus roseus+TX, Sclerotinia minor+TX, Sclerotinia minor (SARRITOR®)+TX, Scytalidium spp.+TX, Scytalidium uredinicola+TX, Spodoptera exigua nuclear polyhedrosis virus (Spod-X®+TX, Spexit®)+TX, Serratia marcescens+TX, Serratia plymuthica+TX, Serratia spp.+TX, Sordaria fimicola+TX, Spodoptera littoralis nucleopolyhedrovirus (Littovir®)+TX, Sporobolomyces roseus+TX, Stenotrophomonas maltophilia+TX, Streptomyces ahygroscopicus+TX, Streptomyces albaduncus+TX, Streptomyces exfoliates+TX, Streptomyces galbus+TX, Streptomyces griseoplanus+TX, Streptomyces griseoviridis (MycostoP®)+TX, Streptomyces lydicus (ActinovatE®)+TX, Streptomyces lydicus WYEC-108 (ActinoGrow®)+TX, Streptomyces violaceus+TX, Tilletiopsis minor+TX, Tilletiopsis spp.+TX, Trichoderma asperellum (T34 Biocontrol®)+TX, Trichoderma gamsii (Tenet®)+TX, Trichoderma atroviride (PlantmatE®)+TX, Trichoderma hamatum TH 382+TX, Trichoderma harzianum rifai (Mycostar®)+TX, Trichoderma harzianum T-22 (Trianum-P®+TX, PlantShield HC®+TX, RootShielD®+TX, Trianum-G®)+TX, Trichoderma harzianum T-39 (Trichodex®)+TX, Trichoderma inhamatum+TX, Trichoderma koningii+TX, Trichoderma spp. LC 52 (Sentinel®)+TX, Trichoderma lignorum+TX, Trichoderma longibrachiatum+TX, Trichoderma polysporum (Binab T®)+TX, Trichoderma taxi+TX, Trichoderma virens+TX, Trichoderma virens (formerly Gliocladium virens GL-21) (SoilGuarD®)+TX, Trichoderma viride+TX, Trichoderma viride strain ICC 080 (Remedier®)+TX, Trichosporon pullulans+TX, Trichosporon spp.+TX, Trichothecium spp.+TX, Trichothecium roseum+TX, Typhula phacorrhiza strain 94670+TX, Typhula phacorrhiza strain 94671+TX, Ulocladium atrum+TX, Ulocladium oudemansii (Botry-Zen®)+TX, Ustilago maydis+TX, various bacteria and supplementary micronutrients (Natural II®)+TX, various fungi (Millennium Microbes®)+TX, Verticillium chlamydosporium+TX, Verticillium lecanii (Mycotal®+TX, VertaleC®)+TX, Vip3Aa20 (VIPtera®)+TX, Virgibacillus marismortui+TX, Xanthomonas campestris pv. Poae (Camperico®)+TX, Xenorhabdus bovienii+TX, Xenorhabdus nematophilus; and Plant extracts including: pine oil (Retenol®)+TX, azadirachtin (Plasma Neem Oil®+TX, AzaGuarD®+TX, MeemAzal®+TX, Molt-X®+TX, Botanical IGR (NeemazaD®+TX, Neemix®)+TX, canola oil (Lilly Miller Vegol®)+TX, Chenopodium ambrosioides near ambrosioides (RequieM®)+TX, Chrysanthemum extract (Crisant®)+TX, extract of neem oil (TrilogY®)+TX, essentials oils of Labiatae (Botania®)+TX, extracts of clove rosemary peppermint and thyme oil (Garden insect Killer®)+TX, Glycinebetaine (GreenstiM®)+TX, garlic+TX, lemongrass oil (GreenMatch®)+TX, neem oil+TX, Nepeta cataria (Catnip oil)+TX, Nepeta catarina+TX, nicotine+TX, oregano oil (MossBuster®)+TX, Pedaliaceae oil (Nematon®)+TX, pyrethrum+TX, Quillaja saponaria (NemaQ®)+TX, Reynoutria sachalinensis (Regalia®+TX, Sakalia®)+TX, rotenone (Eco Roten®)+TX, Rutaceae plant extract (Soleo®)+TX, soybean oil (Ortho EcosensE®)+TX, tea tree oil (Timorex GolD®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm PheromonE®)+TX, Codling Moth Pheromone (Paramount dispenser-(CM)/Isomate C-Plus®)+TX, Grape Berry Moth Pheromone (3M MEC-GBM Sprayable PheromonE®)+TX, Leafroller pheromone (3M MEC-LR Sprayable PheromonE®)+TX, Muscamone (Snip7 Fly Bait®+TX, Starbar Premium Fly Bait®)+TX, Oriental Fruit Moth Pheromone (3M oriental fruit moth sprayable PheromonE®)+TX, Peachtree Borer Pheromone (Isomate-P®)+TX, Tomato Pinworm Pheromone (3M Sprayable PheromonE®)+TX, Entostat powder (extract from palm tree) (Exosex CM®)+TX, (E+TX,Z+TX, Z)-3+TX, 8+TX, 11 Tetradecatrienyl acetate+TX, (Z+TX, Z+TX,E)-7+TX, 11+TX, 13-Hexadecatrienal+TX, (E+TX, Z)-7+TX, 9-Dodecadien-1-yl acetate+TX, 2-Methyl-1-butanol+TX, Calcium acetate+TX, Scenturion®+TX, BiolurE®+TX, Check-MatE®+TX, Lavandulyl senecioate; and Macrobials including: Aphelinus abdominalis+TX, Aphidius ervi (Aphelinus-SysteM®)+TX, Acerophagus papaya+TX, Adalia bipunctata (Adalia-SysteM®)+TX, Adalia bipunctata (AdalinE®)+TX, Adalia bipunctata (Aphidalia®)+TX, Ageniaspis citricola+TX, Ageniaspis fuscicollis+TX, Amblyseius andersoni (AnderlinE®+TX, Andersoni-SysteM®)+TX, Amblyseius califomicus (AmblylinE®+TX, Spical®)+TX, Amblyseius cucumeris (Thripex®+TX, Bugline Cucumeris®)+TX, Amblyseius fallacis (Fallacis®)+TX, Amblyseius swirskii (Bugline SwirskiI®+TX, Swirskii-MitE®)+TX, Amblyseius womersleyi (WomerMitE®)+TX, Amitus hesperidum+TX, Anagrus atomus+TX, Anagyrus fusciventris+TX, Anagyrus kamali+TX, Anagyrus loecki+TX, Anagyrus pseudococci (Citripar®)+TX, Anicetus benefices+TX, Anisopteromalus calandrae+TX, Anthocoris nemoralis (Anthocoris-SysteM®)+TX, Aphelinus abdominalis (AphelinE®+TX, AphilinE®)+TX, Aphelinus asychis+TX, Aphidius colemani (Aphipar®)+TX, Aphidius ervi (Ervipar®)+TX, Aphidius gifuensis+TX, Aphidius matricariae (Aphipar-M®)+TX, Aphidoletes aphidimyza (AphidenD®)+TX, *Aphidoletes aphidimyza* (AphidolinE®)+TX, *Aphytis lingnanensis*+TX, *Aphytis melinus*+TX, *Aprostocetus hagenowii*+TX, *Atheta coriaria* (StaphylinE®)+TX, *Bombus* spp.+TX, *Bombus terrestris* (Natupol BeehivE®)+TX, *Bombus terrestris* (BeelinE®+TX, Tripol®)+TX, *Cephalonomia stephanoderis*+TX, *Chilocorus nigritus*+TX, *Chrysoperla camea* (ChrysolinE®)+TX, *Chrysoperla camea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, CryptolinE®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, DiglinE®)+TX, *Dacnusa sibirica* (DacDiglinE®+TX, Minex®)+TX, *Diversinervus* spp.+TX, *Encarsia citrina*+TX, *Encarsia formosa* (*Encarsia* Max®+TX, EncarlinE®+TX, En-StriP®)+TX, *Eretmocerus eremicus* (Enermix®)+TX, *Encarsia guadeloupae*+TX, *Encarsia haitiensis*+TX, *Episyrphus balteatus* (SyrphidenD®)+TX, *Eretmoceris siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (SpidenD®)+TX, *Feltiella acarisuga* (FeltilinE®)+TX, *Fopius arisanus*+TX, *Fopius ceratitivorus*+TX, Formononetin (Wirless BeehomE®)+TX, *Franklinothrips vespiformis* (VespoP®)+TX, *Galendromus occidentalis*+TX, *Goniozus legneri*+TX, *Habrobracon hebetor*+TX, *Harmonia axyridis* (HarmoBeetlE®)+TX, *Heterorhabditis* spp. (Lawn Patrol®)+TX, *Heterorhabditis bacteriophora* (NemaShield HB®+TX, Nemaseek®+TX, Terranem-NaM®+TX, TerraneM®+TX, LarvaneM®+TX, B-Green®+TX, NemAttack+TX, NematoP®)+TX, *Heterorhabditis megidis* (Nemasys H®+TX, BioNem H®+TX, Exhibitline hM®+TX, Larvanem-M®)+TX, *Hippodamia convergens*+TX, *Hypoaspis aculeifer* (Aculeifer-SysteM®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (NatuflY®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (BioflY®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffee*+TX, *Phytoseiulus macropilus*+TX, *Phytoseiulus persimilis* (Spidex®+TX, Phytoline P®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, MilleniuM®+TX, BioNem C®+TX, NemAttack®+TX, Nemastar®+TX, CapsaneM®)+TX, *Steinernema feltiae* (NemaShielD®+TX, Nemasys F®+TX, BioNem F®+TX, *Steinernema*-SysteM®+TX, NemAttack®+TX, Nemaplus®+TX, Exhibitline SF®+TX, SciaRiD®+TX, EntoneM®)+TX, *Steinernema kraussei* (Nemasys L®+TX, BioNem L®+TX, Exhibitline SrB®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (TrichoStriP®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol PastE®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, *Microctonus hyperodae*+TX, *Mycoleptodiscus terrestris* (Des-X®)+TX, BioGain®+TX, AminomitE®+TX, Zenox®+TX, Pheromone trap (Thripline Ams®)+TX, potassium bicarbonate (MilStoP®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®)+TX, Rebell Amarillo®)+TX and Traps (Takitrapline y+B®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1 to 38 and P with active ingredients described above comprises a compound selected from Tables 1 to 38 and P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 38 and P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 38 and P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1: *Bemisia tabaci* (Cotton White Fly): Feeding/Contact Activity

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation. The following compounds resulted in at least 80% mortality at an application rate of 200 ppm:
P-4, P-5, P-10, P-14, P-15 and P-18.

Example B2: *Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation. The following compounds gave an effect of at least 80% in at least one of the two categories (mortality or growth inhibition) at an application rate of 200 ppm:
P-1, P-2, P-3, P-4, P-5, P-6, P-7, P-8, P-10, P-12, P-13, P-14, P-15, P-16, P-18, P-19, P-20, P-21, P-22, P-23, P-26, I-1, I-3, I-6, I-7, I-8, I-9 and I-11.

Example B3: *Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation. The following compounds gave an effect of at least 80% in at least one of the two categories (mortality or growth inhibition) at an application rate of 200 ppm:
P-1, P-2, P-4, P-5, P-6, P-7, P-10, P-12, P-15, P-16, P-18, P-20, P-22, I-7 and I-8.

Example B4: *Frankliniella occidentalis* (Western Flower *thrips*): Feeding/Contact Activity Sunflower leaf discs were placed on agar in 24-well microtiter plates and sprayed with aqueous test solutions prepared from 10,000 DMSO stock solutions. After drying the leaf discs were infested with a *Frankliniella* population of mixed ages. The samples were assessed for mortality 7 days after infestation. The following compounds resulted in at least 80% mortality at an application rate of 200 ppm:
P-4, P-5, P-6, P-10, P-15 and P-18.

Example B5: *Myzus persicae* (Green Peach Aphid): Feeding/Contact Activity

Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation. The following compounds resulted in at least 80% mortality at an application rate of 200 ppm:
P-1, P-2, P-4, P-5, P-10, P-12, P-13, P-14, P-15, P-18, P-22, I-1, I-5, I-7 and I-8.

Example B6: *Myzus persicae* (Green Peach Aphid). Systemic Activity

Roots of pea seedlings infested with an aphid population of mixed ages were placed directly into aqueous test solutions prepared from 10,000 DMSO stock solutions. The samples were assessed for mortality 6 days after placing seedlings into test solutions. The following compounds resulted in at least 80% mortality at a test rate of 24 ppm:
P-9 and P-13.

Example B7: *Myzus persicae* (Green Peach Aphid). Intrinsic Activity

Test compounds prepared from 10,000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation. The following compounds resulted in at least 80% mortality at a test rate of 12 ppm:
P-14 and I-7.

Example B8: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation. The following compounds gave an effect of at least 80% in at least one of the two categories (mortality or growth inhibition) at an application rate of 200 ppm:
P-1, P-2, P-3, P-4, P-5, P-6, P-7, P-8, P-12, P-13, P-14, P-15, P-16, P-18, P-20, P-22, P-23, P-24, P-26, I-1, I-6, I-7, I-8 and I-10.

Example B9: *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample. The following compounds resulted in at least 80% control at an application rate of 200 ppm:
P-1, P-2, P-4, P-5, P-6, P-7,P-8, P-10, P-12, P-13, P-14, P-15, P-16, P-18, P-19, P-20, P-22, P-23, P-24, P-26, I-1, I-6 and I-8.

Example B10: *Spodoptera littoralis* (Egyptian Cotton Leaf Worm) Systemic Activity Test compounds were applied by pipette from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation. The following compounds gave an effect of at least 80% in at least one of the three categories (mortality, anti-feeding, or growth inhibition) at a test rate of 12.5 ppm:
P-1, P-4, P-5, P-10, P-13, P-15, P-18, I-1, I-6 and I-7.

Example B11: *Tetranychus urticae* (Two-Spotted Spider Mite): Feeding/Contact Activity Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation. The following compounds resulted in at least 80% mortality at an application rate of 200 ppm:
P-6 and I-1.

Example B12: *Thrips tabaci* (Onion *thrips*) Feeding/Contact Activity

Sunflower leaf discs were placed on agar in 24-well microtiter plates and sprayed with aqueous test solutions prepared from 10,000 ppm DMSO stock solutions. After drying the leaf discs were infested with a *thrips* population of mixed ages. The samples were assessed for mortality 6 days after infestation. The following compounds resulted in at least 80% mortality at an application rate of 200 ppm:
P-5, P-10, P-15 and P-18.

Example B13: *Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction. The following compounds gave at least 80% control of *Aedes aegypti* after 48 h and/or 24 h:
P-1, P-4, P-5, P-6 and P-15.

Example B14: *Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction. The following compounds gave at least 80% control of *Anopheles stephensi* after 48 h and/or 24 h:
P-1, P-4, P-5, P-6 and P-15.

Comparative Example

Prior art compound: Compound V14.01 described on page 198 of WO 2015/000715:

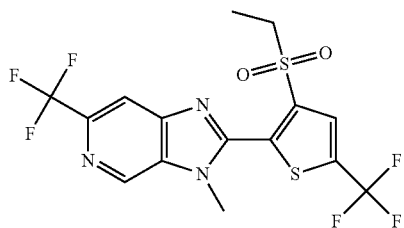

(V14.01)

Compound of this invention:

(compound 2.007, example P1, table 1)

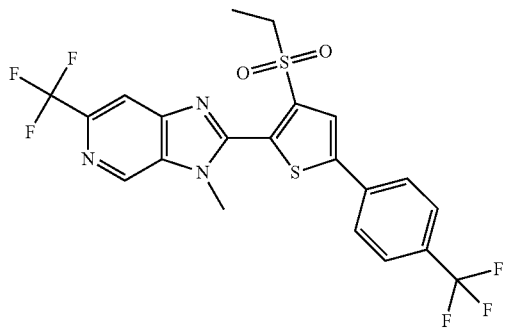 [SMILES: CCS(=O)(=O)c1cc(-c2ccc(C(F)(F)F)cc2)sc1-c1nc2cc(C(F)(F)F)ncc2n1C]

The compounds V14.01, and P1 are structurally identical except for the insertion of a phenyl group between the thiophene ring and the CF3 substiuent.

Example B13

Insecticidal action against *Diabrotica balteata* (Corn root worm), *Plutella xylostella* (Diamond black moth), and *Spodoptera littoralis* (Egyptian cotton leaf worm). The tests were carried out as described in biological examples B2, B8 and B9, respectively, with the larval feeding/contact activity (mortality only) being reported as Breakpoint ($BP_{80}$) values in parts per million (i.e. the lowest concentration which gives 80% larval mortality).

TABLE B13

Insecticidal action against *Diabrotica balteata* (Corn root worm), *Plutella xylostella* (Diamond black moth), and *Spodoptera littoralis* (Egyptian cotton leaf worm).

| | | $BP_{80}$ Values in ppm | | |
|---|---|---|---|---|
| Compound No. | Compound | *Diabrotica balteata* | *Plutella xylostella* | *Spodoptera littoralis* |
| V14.01 | | 50 | 50 | 50 |

TABLE B13-continued

Insecticidal action against *Diabrotica balteata* (Corn root worm), *Plutella xylostella* (Diamond black moth), and *Spodoptera littoralis* (Egyptian cotton leaf worm).

| Compound No. | Compound | $BP_{80}$ Values in ppm | | |
|---|---|---|---|---|
| | | *Diabrotica balteata* | *Plutella xylostella* | *Spodoptera littoralis* |
| 2.007, example P1, table 1 | 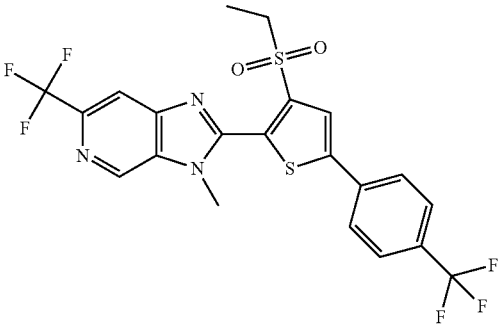 | 0.8 | 0.8 | 0.8 |

As is evident from Table B13, the compound 2.007 (example P1 from table P) according to this invention shows a superior insecticidal action against *Diabrotica balteata* (Corn root worm), *Plutella xylostella* (Diamond black moth), and *Spodoptera littoralis* (Egyptian cotton leaf worm) compared to compound V14.01 of the prior art.

This surprising enhancement of insecticidal activity was not to be expected in view of the close structural similarity of these compounds.

The invention claimed is:

1. A compound of formula I

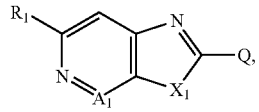
(I)

wherein
$A_1$ is methine;
$R_1$ is hydrogen, halogen, cyano, $C_1$-$C_6$haloalkyl, or $C_1$-$C_6$haloalkyl substituted by one or two substituents selected from the group consisting of hydroxyl, methoxy and cyano; or
$R_1$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl; or
$R_1$ is $C_3$-$C_6$cycloalkyl which can be mono- or polysubstituted by substituents selected from the group consisting of halogen, cyano and $C_1$-$C_4$alkyl;
$X_1$ is nitrogen substituted with $R_2$, wherein $R_2$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl; or
$X_1$ is oxygen or sulfur;
Q is a group Qa or Qb;

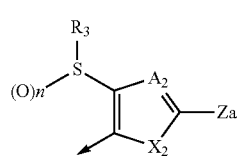
Qa

-continued

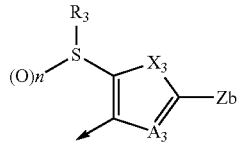
Qb wherein the arrow represents the point of attachment to formula I, and wherein Za and Zb, independently from each other, are phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Za and Zb, independently from each other, are a five- to ten-membered monocyclic or fused bicyclic ring system linked via a carbon atom to the ring which contains the 5-membered heterocycle, said ring system can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Za and Zb are, independently from each other, a five- to six-membered, aromatic, partially saturated or fully saturated ring system linked via a nitrogen atom to the ring which contains the 5-membered heterocycle, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkyl sulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulfur, with the proviso that said ring system cannot contain more than one oxygen atom and more than one sulfur atom; or Za and Zb, independently from each other, are $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Za and Zb, independently from each other, are $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Za and Zb, independently from each other, are $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl; or Za and Zb, independently from each other, are $C_1$-$C_6$alkyl, or $C_1$-$C_6$alkyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl;

$A_2$ is $CR_4$ or nitrogen;
$A_3$ is $CR_5$ or nitrogen;
$R_3$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_3$ is $C_3$-$C_6$cycloalkyl-$C_1$-$C_4$alkyl mono- or polysubstituted by substituents selected from the group consisting of halogen, cyano and $C_1$-$C_4$alkyl; or
$R_3$ is $C_2$-$C_6$alkenyl, $C_2$-$C_6$haloalkenyl or $C_2$-$C_6$alkynyl;
$R_4$ is hydrogen, halogen, or $C_1$-$C_4$alkyl;
$R_5$ is hydrogen, halogen, or $C_1$-$C_4$alkyl;
$X_2$ is oxygen or sulfur;
$X_3$ is oxygen or sulfur;
n is 0, 1 or 2;
or an agrochemically acceptable salt, stereoisomer, enantiomer thereof.

2. A compound of formula I according to claim 1, wherein Za and Zb, independently from each other, are selected from the group consisting of J-0 to J-50:

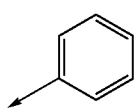

J-0

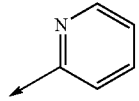

J-1

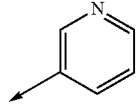

J-2

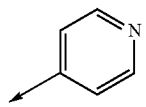

J-3

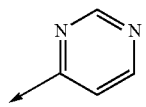

J-4

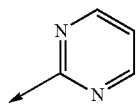

J-5

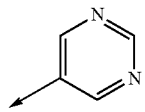

J-6

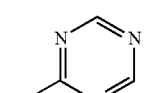

J-7

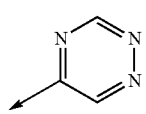

J-8

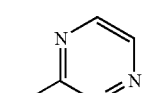

J-9

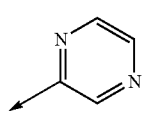

J-10

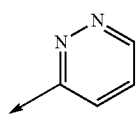

J-11

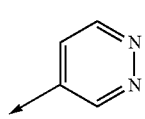

J-12

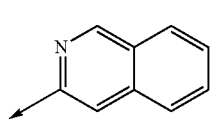

J-13

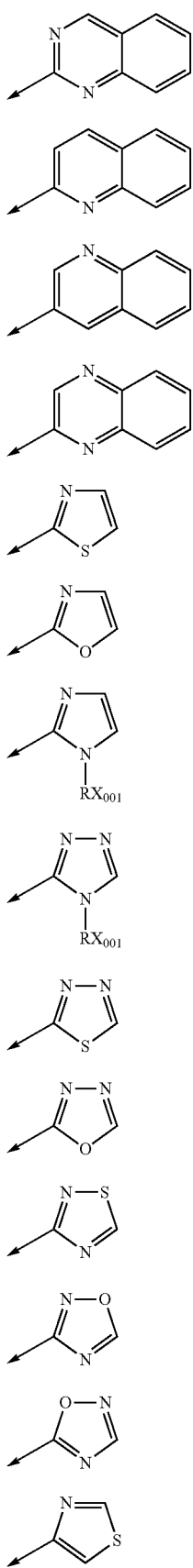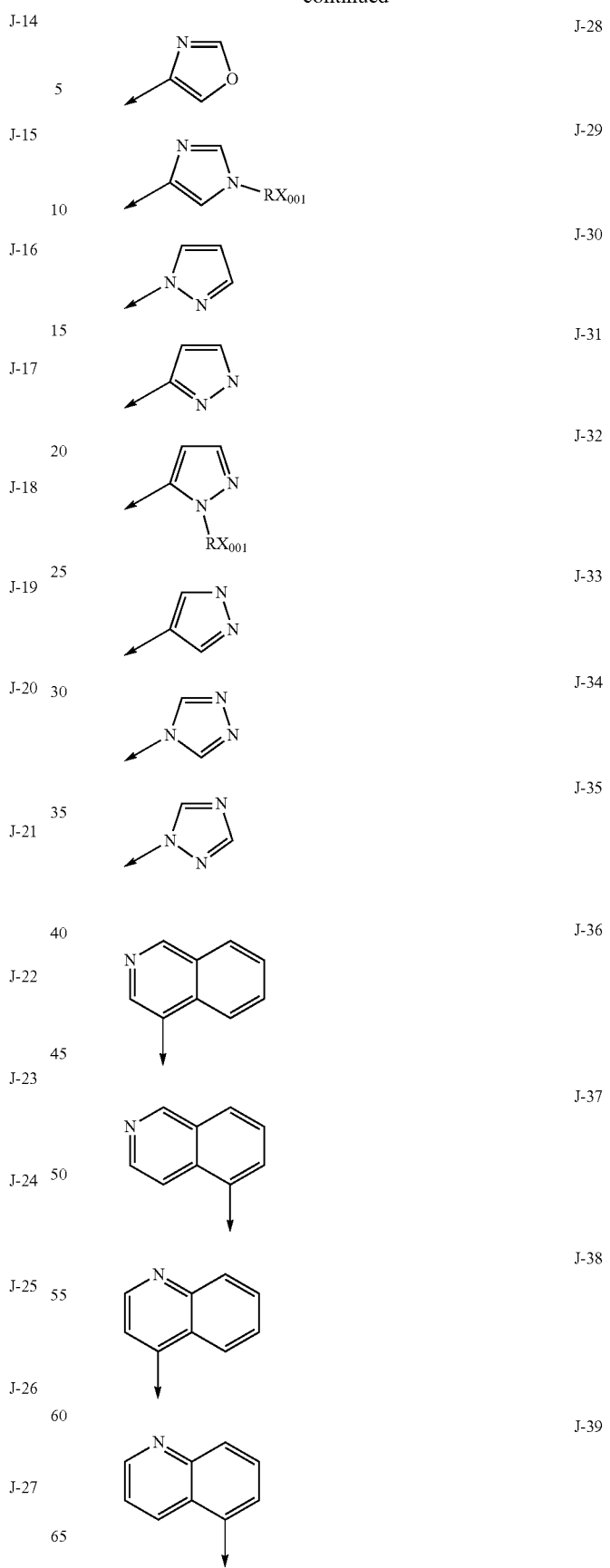

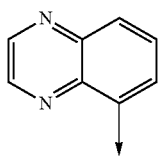
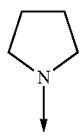
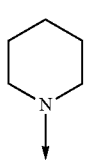
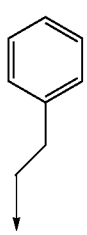

J-40

J-41

J-42

J-43

J-44

J-45

J-46

J-47

J-48

J-49

J-50

wherein each group J-0 to J-50 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C(O)C_1$-$C_4$alkyl, $C_1$-$C_4$haloalkylsulfanyl, $C_1$-$C_4$haloalkylsulfinyl, $C_1$-$C_4$haloalkylsulfonyl and $C(O)C_1$-$C_4$haloalkyl; and wherein $R_{x001}$ hydrogen or $C_1$-$C_4$alkyl.

3. A compound of formula I according to claim 1, represented by the compounds of formula I-1

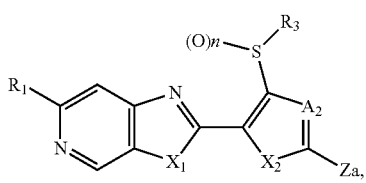

(I-1)

wherein $R_1$, $A_2$, $X_1$, $X_2$, n, and Za are as defined under formula I in claim 1; $R_3$ is methyl, ethyl, n-propyl, i-propyl or cyclopropylmethyl; and $X_1$ is N-methyl, oxygen or sulfur.

4. A compound of formula I according to claim 1, represented by the compounds of formula I-1a

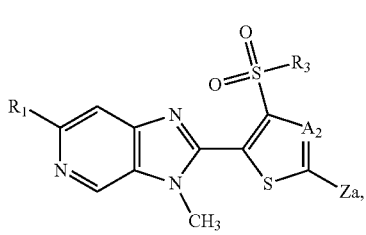

(I-1a)

wherein
$A_2$ is nitrogen, methine, or C—Cl;
$R_3$ is $C_1$-$C_4$alkyl;
$R_1$ is $C_1$-$C_4$haloalkyl, or $C_1$-$C_4$haloalkoxy, $C_1$-$C_4$haloalkylsulfanyl, $C_1$-$C_4$haloalkylsulfinyl or $C_1$-$C_4$haloalkylsulfonyl; and Za is selected from the group consisting of

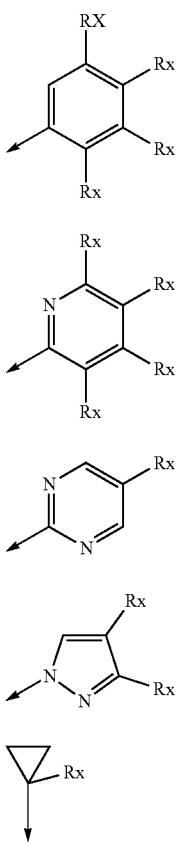

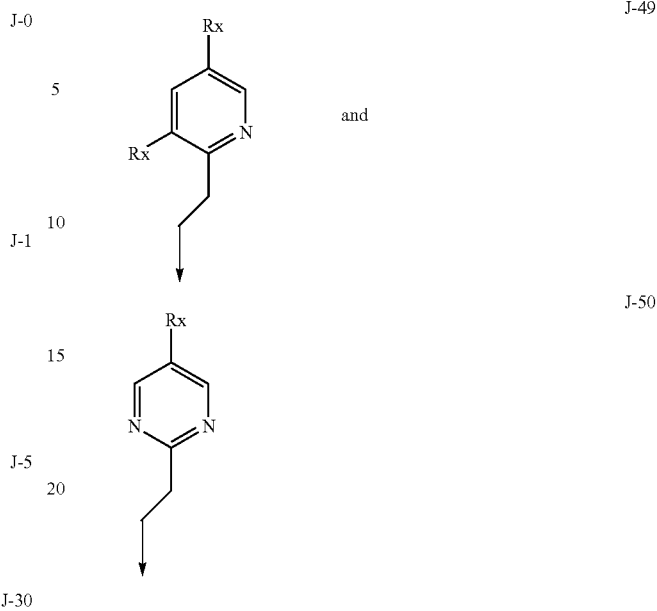

wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

5. A compound of formula I according to claim 1, represented by the compounds of formula I-2

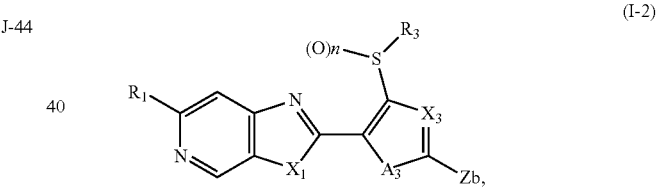

wherein $R_1$, $A_3$, $X_1$, $X_3$, n, and Zb are as defined under formula I in claim 1; $R_3$ is methyl, ethyl, n-propyl, i-propyl or cyclopropylmethyl; and $X_1$ is N-methyl, oxygen or sulfur.

6. A compound of formula I according to claim 1, represented by the compounds of formula I-2a

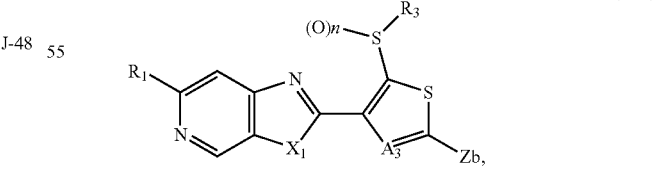

wherein
$A_3$ is nitrogen or methine;
$R_3$ is $C_1$-$C_4$alkyl;
$R_1$ is $C_1$-$C_4$haloalkyl, or $C_1$-$C_4$haloalkoxy, $C_1$-$C_4$haloalkylsulfanyl, $C_1$-$C_4$haloalkylsulfinyl or $C_1$-$C_1$haloalkylsulfonyl; and Zb is selected from the group consisting of J-0
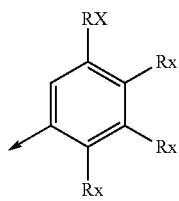

J-1
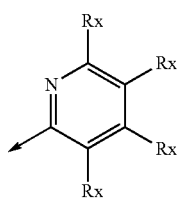

J-5
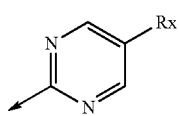

J-30
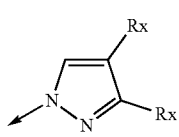

J-43

J-44
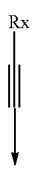

J-46

J-48
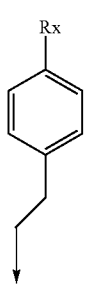

-continued

J-49
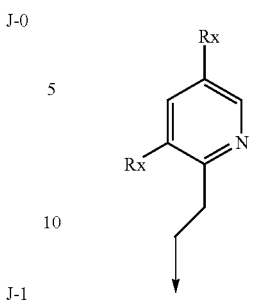

and

J-50
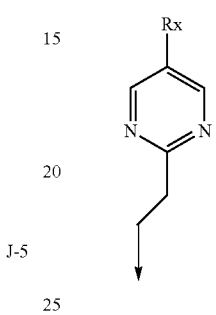

wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkyl sulfonyl, —C(O)$C_1$-$C_4$alkyl, $C_1$-$C_4$haloalkylsulfanyl, $C_1$-$C_4$haloalkylsulfinyl, $C_1$-$C_4$haloalkyl sulfonyl and —C(O)$C_1$-$C_4$haloalkyl.

7. A compound of formula I-3a

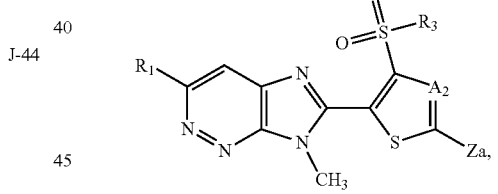
(I-3a)

wherein $A_2$ is nitrogen or methine;

$R_3$ is $C_1$-$C_4$alkyl;

$R_1$ is $C_1$-$C_4$haloalkyl, or $C_1$-$C_4$haloalkoxy, $C_1$-$C_4$haloalkylsulfanyl, $C_1$-$C_4$haloalkylsulfinyl or $C_1$-$C_4$haloalkylsulfonyl; Za is selected from the group consisting of the substituents J-0
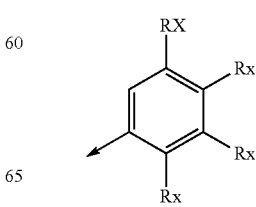

-continued

J-1 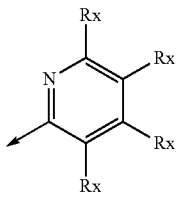

J-5 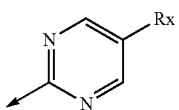

J-30 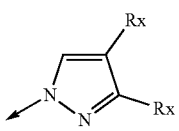

J-43 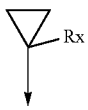

J-44 

J-46 

J-48 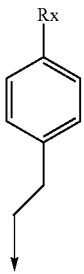

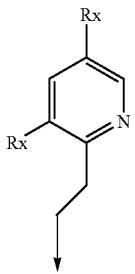 and

-continued

J-50 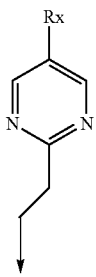

wherein each Rx is, independently from each other, selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

8. A compound of formula I according to claim 1, represented by the compounds of formula I-4a

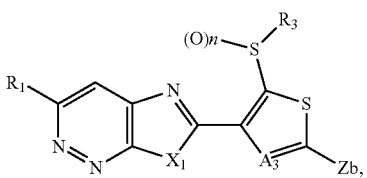

(I-4a)

wherein $A_3$ is nitrogen or methine;

$R_3$ is $C_1$-$C_4$alkyl;

$R_1$ is $C_1$-$C_4$haloalkyl, or $C_1$-$C_4$haloalkoxy, $C_1$-$C_4$haloalkylsulfanyl, $C_1$-$C_4$haloalkylsulfinyl or $C_1$-$C_4$haloalkylsulfonyl; and Zb is selected from the group consisting of J-0 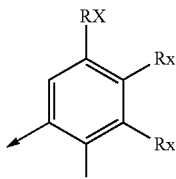

J-1 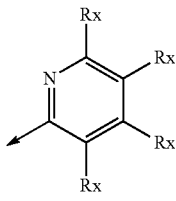

J-5

-continued

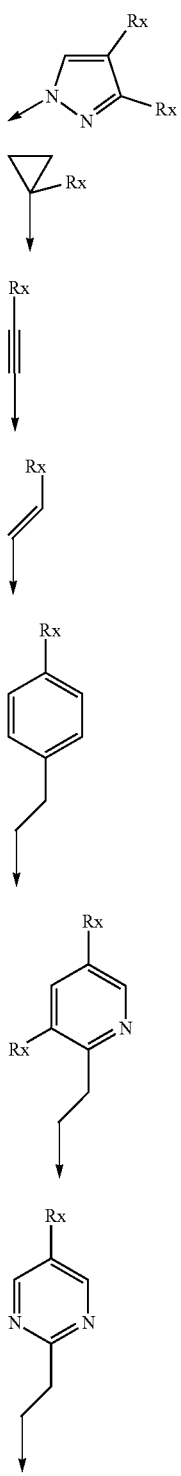

wherein each Rx is, independently from each other, selected from the group consisting of hydrogen, halogen, cyano, C$_1$-C$_4$alkyl, C$_1$-C$_4$haloalkyl, C$_1$-C$_4$haloalkoxy, C$_1$-C$_4$alkoxy, C$_1$-C$_4$alkylsulfanyl, C$_1$-C$_4$alkylsulfinyl, C$_1$-C$_4$alkylsulfonyl, —C(O)C$_1$-C$_4$alkyl, C$_1$-C$_4$haloalkylsulfanyl, C$_1$-C$_4$haloalkylsulfinyl, C$_1$-C$_4$haloalkylsulfonyl, or —C(O)C$_1$-C$_4$haloalkyl.

9. A pesticidal composition, which comprises at least one compound of formula I according to claim 1 or, where appropriate, a tautomer thereof, in each case in free form or in agrochemically utilizable salt form, as active ingredient and at least one auxiliary.

10. A method for controlling pests, which comprises applying a composition according to claim 9 to the pests or their environment with the exception of a method for treatment of the human or animal body by surgery or therapy and diagnostic methods practiced on the human or animal body.

11. A method for the protection of seeds from the attack by pests, which comprises treating the seeds or the site, where the seeds are planted, with a composition according to claim 9.

12. A compound of Formula IIa or IIb;

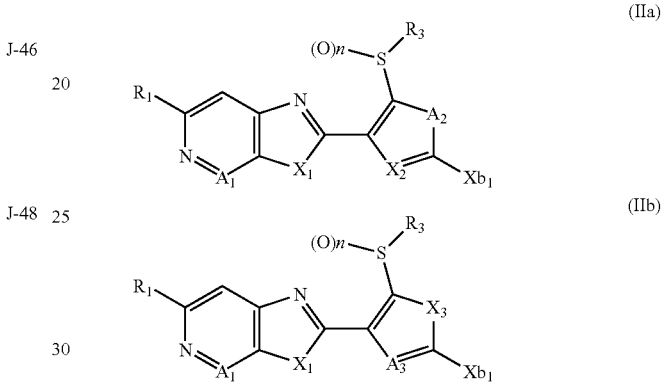

R$_1$ is hydrogen, halogen, cyano, C$_1$-C$_6$haloalkyl, or C$_1$-C$_6$haloalkyl substituted by one or two substituents selected from the group consisting of hydroxyl, methoxy and cyano; or R$_1$ is C$_1$-C$_4$haloalkylsulfanyl, C$_1$-C$_4$haloalkylsulfinyl, C$_1$-C$_4$haloalkylsulfonyl, O(C$_1$-C$_4$haloalkyl), or —C(O)C$_1$-C$_4$haloalkyl; or R$_1$ is C$_3$-C$_6$cycloalkyl which can be mono- or polysubstituted by substituents selected from the group consisting of halogen, cyano and C$_1$-C$_4$alkyl;

A$_1$ is methine, nitrogen or the N-oxide;

X$_1$ is nitrogen substituted with R$_2$, wherein R$_2$ is hydrogen, C$_1$-C$_4$alkyl, C$_2$-C$_6$alkenyl, C$_2$-C$_6$alkynyl, C$_1$-C$_4$alkoxy-C$_1$-C$_4$alkyl or C$_3$-C$_6$cycloalkyl; or X$_1$ is oxygen or sulfur;

X$_2$ is oxygen or sulfur;

A$_2$ is CR$_4$ or nitrogen;

A$_3$ is CR$_5$ or nitrogen;

R$_4$ is hydrogen, halogen, or C$_1$-C$_4$alkyl;

R$_5$ is hydrogen, halogen, or C$_1$-C$_4$alkyl;

X$_3$ is oxygen or sulfur;

R$_3$ is C$_1$-C$_4$alkyl, C$_1$-C$_4$haloalkyl, C$_3$-C$_6$cycloalkyl, C$_3$-C$_6$cycloalkyl-C$_1$-C$_4$alkyl; or R$_3$ is C$_3$-C$_6$cycloalkyl-C$_1$-C$_4$alkyl mono- or polysubstituted by substituents selected from the group consisting of halogen, cyano and C$_1$-C$_4$alkyl; or R$_3$ is C$_2$-C$_6$alkenyl, C$_2$-C$_6$haloalkenyl or C$_2$-C$_6$alkynyl;

n is 0, 1 or 2; and

Xb1 is halogen, with the proviso that IIb is not 2-bromo-5-ethylsulfonyl-4-[3-methyl-6-(trifluoromethyl)imidazo[4,5-c]pyridin-2-yl]thiazole, and wherein when R$_3$ is ethyl, n is 0-2, R$_1$ is trifluoromethyl, A$_1$ is nitrogen, X$_2$ is sulfur, A$_2$ is nitrogen, and X$_1$ is nitrogen substituted with methyl then Xb$_1$ is not iodine.

13. The compounds of claim 12, wherein A1 is methine.

* * * * *